(12) United States Patent
Zindel et al.

(10) Patent No.: US 6,645,916 B1
(45) Date of Patent: Nov. 11, 2003

(54) 2,4-DIAMINO-1,3,5-TRIAZINES, THEIR PREPARATION AND THEIR USE AS HERBICIDES AND PLANT GROWTH REGULATORS

(75) Inventors: Jürgen Zindel, Bad Sooden-Allendorf (DE); Jens Hollander, Schmitten (DE); Klemens Minn, Hattersheim (DE); Lothar Willms, Hofheim (DE); Hermann Bieringer, Eppstein (DE); Christopher Rosinger, Hofheim (DE)

(73) Assignee: Hoechst Schering AgrEvo GmbH, Frankfurt am Main (DE)

( * ) Notice: Subject to any disclaimer, the term of this patent is extended or adjusted under 35 U.S.C. 154(b) by 0 days.

(21) Appl. No.: 10/350,738

(22) Filed: Jan. 24, 2003

Related U.S. Application Data

(63) Continuation of application No. 09/020,292, filed on Feb. 6, 1998, now abandoned.

(30) Foreign Application Priority Data

Feb. 10, 1997 (DE) .......................... 197 04 922

(51) Int. Cl.$^7$ .................. C07D 251/18; A01N 43/68
(52) U.S. Cl. .................. 504/234; 544/206; 544/207; 544/113
(58) Field of Search ............... 544/206, 207, 544/113; 504/234

(56) References Cited

U.S. PATENT DOCUMENTS

| | | | |
|---|---|---|---|
| 5,095,113 A | 3/1992 | Chiang | 544/194 |
| 5,290,754 A | 3/1994 | Nishii et al. | 504/232 |
| 5,403,815 A | 4/1995 | Nishii et al. | 504/230 |
| 5,527,954 A | 6/1996 | Adachi et al. | 560/227 |

FOREIGN PATENT DOCUMENTS

| | | |
|---|---|---|
| CA | 2197091 | 2/1996 |
| EP | 0130939 A1 | 1/1985 |
| EP | 0492615 A1 | 7/1992 |
| EP | 0506059 A2 | 9/1992 |
| EP | 0509544 A2 | 10/1992 |
| EP | 0810219 A1 | 12/1997 |
| WO | WO 90/09378 | 8/1990 |
| WO | WO 94/24086 | 10/1994 |
| WO | WO 96/25404 | 8/1996 |
| WO | WO 97/35481 | 10/1997 |

OTHER PUBLICATIONS

Chem. Ber., Vol. 100, p. 1874 (1967).

J. Heterocyclic Chem., Vol. 23, p. 1706 (1986).

Tetrehedron, Vol. 31, p. 1879 (1975).

Kamimura, et al., Chemical Abstracts 122:133222, abstract of JP 06–298,745.

Adachi, et al., Chemical Abstracts 118:169120, abstract of EP 509,544.

*Primary Examiner*—John M. Ford
(74) *Attorney, Agent, or Firm*—Frommer Lawrence & Haug LLP

(57) ABSTRACT

This invention provides for 2,4-diamino-1,3,5-triazines, their preparation and their use as herbicides or plant growth regulators.

13 Claims, No Drawings

2,4-DIAMINO-1,3,5-TRIAZINES, THEIR PREPARATION AND THEIR USE AS HERBICIDES AND PLANT GROWTH REGULATORS

RELATED APPLICATIONS

This application is a continuation of parent application, U.S. Ser. No. 09/020,292, filed on Feb. 6, 1998, now abn, herein incorporated by reference, which claims priority of German application No. 197 04 922.2, filed on Feb. 10, 1997.

It is known that some 2-amino4-(phenoxyethylamino)-1, 3,5-triazines substituted in position 6 have herbicidal and plant growth-regulating properties; cf. WO 90/09378 (U.S. Pat. No. 5,290,754 and U.S. Pat. No. 5,403,815), WO 94/24086 (U.S. Pat. No. 5,527,954), WO 96/25404.

Some of the known compounds have disadvantages when being used, be it insufficient herbicidal activity against harmful plants, too small a spectrum of harmful plants which can be controlled by one active compound, or inadequate selectivity in crops of useful plants.

It is an object of the present invention to provide alternative or improved active compounds of the type of the 2,4-diamino-1,3,5-triazines which can be used as herbicides or plant growth regulators.

The resent invention provides compounds of the formula (I) and salts thereof

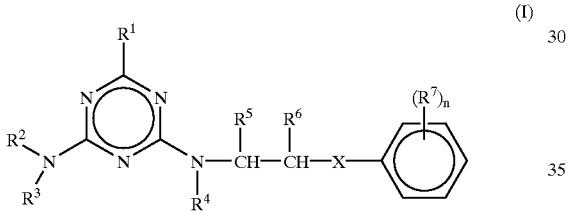

(I)

in which
$R^1$ is $(C_1-C_6)$alkyl,
which is unsubstituted or substituted by one or more radicals from the group consisting of halogen, hydroxyl, cyano, nitro, thiocyanato, $(C_1-C_4)$alkoxy, $(C_1-C_4)$alkylthio, $(C_1-C_4)$alkylsulfinyl, $(C_1-C_4)$alkylsulfonyl, $(C_2-C_4)$alkenyl, $(C_2-C_4)$alkynyl and phenyl which is unsubstituted or substituted, or
is phenyl which is unsubstituted or substituted,
$R^2$ and $R^3$ in each case independently of one another are hydrogen,
amino, $(C_1-C_6)$alkyl-amino or di-$[(C_1-C_6)$alkyl] amino, a hydrocarbon radical or hydrocarbonoxy radical having in each case 1 to 10 carbon atoms, preferably having 1 to 6 carbon atoms, or a heterocyclyl radical, heterocyclyloxy radical or heterocyclylamino radical having in each case 3 to 9 ring atoms and 1 to 3 hetero-ring atoms from the group consisting of N, O and S, each of the five last-mentioned radicals being unsubstituted or substituted, or are an acyl radical, or
$R^2$ and $R^3$, together with the nitrogen atom of the group $NR^2R^3$, are a heterocyclic radical having 3 to 6 ring atoms and 1 to 4 hetero-ring atoms, any further hetero-ring atoms in addition to the nitrogen atom being selected from the group consisting of N, O and S, and the radical being unsubstituted or substituted,
$R^4$ is hydrogen, amino, $(C_1-C_6)$alkylamino, di-$[(C_1-C_6)$alkyl]amino, a hydrocarbon radical or hydrocarbonoxy radical having in each case 1 to 10 carbon atoms, preferably having 1 to 6 carbon atoms, or a heterocyclyl radical, heterocyclyloxy radical or heterocyclylamino radical having in each case 3 to 9 ring atoms and 1 to 3 hetero-ring atoms from the group consisting of N, O and S, each of the five last-mentioned radicals being unsubstituted or substituted, or an acyl radical,
$R^5$ and $R^6$ in each case independently of one another are halogen, nitro, cyano, thiocyanato or a radical of the formula $—X^1—A^1$
in which $X^1$ is a direct bond or a bivalent group of the formula $—O—$, $—S(O)_p—O—$, $—O—S(O)_p—$, $—CO—$, $—O—CO—$, $—CO—O—$, $—NR'—$, $—O—NR'—$, $—NR'—O—$, $—NR'—CO—$ or $—CO—NR'—$, p in the formulae being 0, 1 or 2 and R' being hydrogen, alkyl having 1 to 6 carbon atoms, phenyl, benzyl, cycloalkyl having 3 to 6 carbon atoms or alkanoyl having 1 to 6 carbon atoms, and
in which $A^1$ is hydrogen or a hydrocarbon radical or a heterocyclic radical, each of the two last-mentioned radicals being unsubstituted or substituted, or
$R^5$ and $R^6$ together are an alkylene chain having 2 to 4 carbon atoms which is unsubstituted or substituted by one or more radicals from the group consisting of halogen, $(C_1-C_4)$alkyl and oxo,
$R^7$ independently of other radicals $R^7$ is in each case halogen, nitro, cyano, thiocyanato or a radical of the formula $—X^2—A^2$,
in which $X^2$ is a direct bond or a bivalent group of the formula $—O—$, $—S(O)_q—$, $—S(O)_q—O—$, $—O—S(O)_q—$, $—CO—$, $—O—CO—$, $—CO—O—$, $—NR''—$, $—O—N—R''—$, $—NR''—O—$, $—NR''—CO—$ or $—CO—NR''—$, q in the formulae being 0, 1 or 2 and R' being hydrogen, $(C_1-C_6)$-alkyl, phenyl, $(C_3-C_6)$-cycloalkyl, and $A^2$ is hydrogen or a hydrocarbon radical or a heterocyclic radical, each of the two last-mentioned radicals being unsubstituted or substituted,
or two adjacent radicals $R^7$ together are a fused-on cycle having 4 to 6 ring atoms, which is carbocyclic or contains hetero-ring atoms from the group consisting of O, S and N, and which is unsubstituted or substituted by one or more radicals from the group consisting of halogen, $(C_1-C_4)$alkyl and oxo,
X is a group of the formula $—O—$, $—S(O)_r—$, $—NR*—$ or $—N(O)—$, in which r is 0, 1 or 2 and $R^*$ is hydrogen or alkyl having 1 to 4 carbon atoms, and
n is 0, 1, 2, 3, 4 or 5,
except for compounds of the formula (I) or salt thereof
a) in which
$R^1$ is 1-haloethyl, 1-halo-1-methyl-ethyl or 1-halo-1-methyl-propyl,
$R^2$, $R^3$, $R^4$, $R^6$ are each hydrogen,
$R^5$ is methyl,
$R^7$ is $(C_1-C_4)$alkyl, $CF_3$, $OCH_3$ or fluorine, where in the case of n=2 both radicals $R^7$ are defined the same,
n is the number 0, 1 or 2 and
X is an oxygen atom, and
b) in which
$R^1$ is $(C_1-C_{10})$alkyl, which is unsubstituted or substituted by 1 to 4 substituents from the group consisting of $(C_1-C_4)$alkoxy and hydroxyl,
$R^2$, $R^3$, $R^4$, $R^6$ are each hydrogen,
$R^5$ is methyl,
$R^7$ independently of other radicals $R^7$ is in each case $(C_1-C_4)$alkyl or halogen
n is the, number 0, 1, 2, 3 or 4 and
X is an oxygen atom., The compounds of formula (I) can form salts by adding on an appropriate inorganic or organic acid, for example HCl, HBr, $H_2SO_4$ or $HNO_3$, or else oxalic acid or sulfonic acids, to a basic group, for example amino or alkylamino. Suitable substituents, which may be in deprotonated form, such as, for example, sulfonic acids or carboxylic acids, may form inner salts with groups which are in turn protonateable, such as amino groups. Salts can likewise be formed by replacing the hydrogen in appropriate substituents, for example sulfonic acids or carboxylic acids, by an agriculturally useful cation. Examples of these salts are metal salts, in particular alkali metal salts, or alkaline earth metal salts, in particular sodium salts and potassium salts, or else ammonium salts or salts with organic amines.

In formula (I) and all subsequent formulae, the radicals alkyl, alkoxy, haloalkyl, haloalkoxy, alkylamino and alkylthio and the corresponding unsaturated and/or substituted radicals can in each case be straight-chain or branched in the carbon skeleton. Unless indicated specifically, the lower carbon skeletons, for example those having 1 to 6 carbon atoms or, in the case of unsaturated groups, having 2 to 6 carbon atoms, are preferred for these radicals.

$(C_1-C_6)$alkyl is the short notation for alkyl having 1 to 6 carbon atoms. Halo-$(C_1-C_6)$alkyl and $(C_1-C_6)$haloalkyl are both haloalkyl having 1 to 6 carbon atoms in the alkyl moiety; this applies correspondingly to other (substituted) radicals. Alkyl radicals, also in the composite meanings such as alkoxy, haloalkyl, etc., are, for example, methyl, ethyl, n- or i-propyl, n-, i-, t- or 2-butyl, pentyls, hexyls, such as n-hexyl, i-hexyl and 1,3-dimethylbutyl, heptyls, such as n-heptyl, 1-methylhexyl and 1,4-dimethylpentyl; alkenyl and alkynyl radicals have the meaning of the possible unsaturated radicals corresponding to the alkyl radicals; alkenyl is, for example, ethenyl, allyl, 1-methylprop-2-en-1-yl, 2-methyl-prop-2-en-1-yl, but-2-en-1-yl, but-3-en-1-yl, 1-methyl-but-3-en-1-yl and 1-methyl-but-2-en-1-yl; alkynyl is, for example, ethynyl, propargyl, but-2-in-1-yl, but-3-in-1-yl, 1-methyl-but-3-in-1-yl. Cycloalkyl is a carbocyclic saturated ring system preferably having 3–6 carbon atoms, for example cyclopropyl, cyclopentyl or cyclohexyl.

Halogen is, for example, fluorine, chlorine, bromine, or iodine. Haloalkyl, haloalkenyl and haloalkynyl are alkyl, alkenyl and alkynyl, respectively, which are fully or partially substituted by halogen, preferably by fluorine, chlorine and/or bromine, in particular by fluorine or chlorine, for example monohaloalkyl (=monohalogenoalkyl), perhaloalkyl, $CF_3$, $CHF_2$, $CH_2F$, $CF_3CF_2$, $CHF_2CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $CHF_2CF_2O$, $OCH_2CF_3$ and $OCH_2CH_2Cl$; this applies correspondingly to haloalkenyl and other halogen-substituted radicals and, less preferred, also to alkyl radicals having substituents other than halogen.

A hydrocarbon radical is a straight-chain, branched or cyclic and saturated or unsaturated aliphatic or aromatic hydrocarbon radical, for example alkyl, alkenyl, alkynyl, cycloalkyl, cycloalkenyl or aryl; aryl in this case is a mono-, bi or polycyclic aromatic system, for example phenyl, naphthyl, tetrahydronaphthyl, indenyl, indanyl, pentalenyl, fluorenyl and the like, preferably phenyl; a hydrocarbon radical is preferably alkyl, alkenyl or alkynyl having up to 12 carbon atoms or cycloalkyl having 3, 4, 5 or 6 ring atoms or phenyl; this applies correspondingly to a hydrocarbon radical in a hydrocarbonoxy radical.

A heterocyclic radical or ring (heterocyclyl) can be saturated, unsaturated or heteroaromatic; it preferably contains one or more hetero atoms in the ring, preferably from the group consisting of N, O and S; it is preferably an aliphatic heterocycyl radical having 3 to 7 ring atoms or a heteroaromatic radical having having 5 or 6 ring atoms and contains 1, 2 or 3 hetero-ring atoms. The heterocyclic radical can, for example, be a heteroaromatic radical or ring (heteroaryl), for example a mono-, bi or polycyclic aromatic system in which at least one ring contains one or more hetero atoms, for example pyridyl, pyrimidinyl, pyridazinyl, pirazinyl, thienyl, thiazolyl, oxazolyl, furyl, pyrrolyl, pyrazolyl and imidazolyl, or is a partially or fully hydrogenated radical such as oxiranyl, pyrrolidyl, piperidyl, piperazinyl, dioxolanyl, morpholinyl, tetrahydrofuryl. Suitable substituents for a substituted heterocyclic radical are the substituents mentioned further below, and additionally also oxo. The oxo group can also occur at the hetero-ring atoms, which may exist in various oxidation stages, for example in the case of N and S.

Substituted radicals, such as substituted hydrocarbon radicals, for example substituted alkyl, alkenyl, alkynyl, aryl, phenyl and benzyl, or substituted heterocyclyl or heteroaryl, are, for example, a substituted radical derived from the unsubstituted skeleton, the substituents being, for example, one or more, preferably 1, 2 or 3, radicals from the group consisting of halogen, alkoxy, haloalkoxy, alkylthio, hydroxyl, amino, nitro, carboxyl, cyano, azido, alkoxycarbonyl, alkylcarbonyl, formyl, carbamoyl, mono- and dialkylaminocarbonyl, substituted amino, such as acylamino, mono- and dialkylamino, alkylsulfinyl, haloalkylsulfinyl, alkylsulfonyl, haloalkylsulfonyl and, in the case of cyclic radicals, also alkyl and haloalkyl; the term "one or more substituents from the group consisting of halogen, alkoxy, . . . and haloalkyl" means that, in the case of a plurality of substituents, these are identical or different. In the term "substituted radicals" such as substituted alkyl etc., substituents include not only the abovementioned saturated hydrocarbon-containing radicals but also the corresponding unsaturated aliphatic and aromatic radicals, such as substituted or unsubstituted alkenyl, alkynyl, alkenyloxy, alkynyloxy, phenyl, phenoxy, etc. In the case of radicals having carbon atoms, preference is given to those having 1 to 4 carbon atoms, in particular 1 or 2 carbon atoms. Generally preferred substituents are those from the group consisting of halogen, for example fluorine and chlorine, $(C_1-C_4)$alkyl, preferably methyl or ethyl, $(C_1-C_4)$haloalkyl, preferably $CF_3$, $(C_1-C_4)$alkoxy, preferably $OCH_3$ or $OC_2H_5$, $(C_1-C_4)$haloalkoxy, nitro and cyano.

Particularly preferred in this context are the substituents methyl, methoxy and chlorine.

Unsubstituted or substituted phenyl is preferably phenyl which is unsubstituted or mono- or polysubstituted, preferably substituted up to three times by identical or different radicals from the group consisting of halogen, $(C_1-C_4)$alkyl, $(C_1-C_4)$alkoxy, $(C_1-C_4)$haloalkyl, $(C_1-C_4)$haloalkoxy and nitro, for example o-, m- and p-tolyl, dimethylphenyls, 2-, 3- and 4-chlorophenyl, 2-, 3- and 4-trifluoro and -trichlorophenyl, 2,4-, 3,5-, 2,5- and 2,3-dichlorophenyl, o-, m- and p-methoxyphenyl. Mono- or disubstituted amino is a chemically stable radical where the amino group is N-substituted for example by one or two identical or different radicals from the group consisting of (substituted) alkyl, (substituted) alkoxy, acyl and (substituted) aryl, preferably monoalkylamino, dialkylamino, acylamino, arylamino, N-alkyl-N-arylamino and N-heterocycles; preferred in this context are alkyl radicals having 1 to 4 carbon atoms; aryl in this context is preferably phenyl; acyl is subject to the definition given further below, and is preferably $(C_1-C_4)$ alkanoyl.

This applies correspondingly to substituted hydroxylamino or hydrazino.

An acyl radical is the radical of an organic acid, for example the radical of a carboxylic acid and radicals of acids derived therefrom, such as of thiocarboxylic acid, unsubstituted or N-substituted iminocarboxylic acids or the radical of carbonic monoesters, unsubstituted or N-substituted carbamic acid, sulfonic acids, sulfinic acids, phosphonic acids and phosphinic acids. Acyl is, for example, formyl, alkylcarbonyl such as $[(C_1-C_4)alkyl]$-carbonyl, phenylcarbonyl, alkyloxycarbonyl, phenyloxycarbonyl, benzyloxycarbonyl, alkylsulfonyl, alkylsulfinyl, N-alkyl-1-iminoalkyl and other radicals of organic acids. These radicals can in each case be substituted further in the alkyl or phenyl moiety, for example in the alkyl moiety by one or more radicals from the group consisting of halogen, alkoxy, phenyl and phenoxy; examples of substituents in the phenyl moiety are the substituents already mentioned further above in general for substituted phenyl.

The invention also provides all stereoisomers covered by formula (I), and mixtures thereof. Such compounds of the formula (I) contain one or more asymmetric carbon atoms or else double bonds, which are not indicated separately in the general formula (I). The possible stereoisomers defined by their specific spatial form, such as enantiomers, diastereomers, Z and E isomers, are all covered by the formula (I) and can be obtained by customary methods from mixtures of the stereoisomers or else by stereoselective reactions in combination with the use of stereochemically pure starting materials.

Also covered are tautomers which are formed by moving one or more double bonds in the triazine ring to the amino substituents to give imine-like structures, if the amino substituent in formula (I) contained an N—H bond ($R^2$, $R^3$ and/or $R^4$=H).

For reasons in particular of greater herbicidal action, better selectivity and/or greater ease of preparation, particular interest attaches to novel compounds of the abovementioned formula (I) or salts thereof in which $R^1$ is $(C_1-C_4)$alkyl,
which is unsubstituted or substituted by one or more radicals from the group consisting of halogen, hydroxyl, $(C_1-C_4)$alkoxy, $(C_1-C_4)$alkylthio, $(C_1-C_4)$alkylsulfonyl and phenyl, or
phenyl which is unsubstituted or substituted, $R^2$ and $R^3$ in each case independently of one another are
hydrogen,
amino or $(C_1-C_4)$alkylamino, di-$[(C_1-C_4)alkyl]$-amino, a hydrocarbon radical or hydrocarbonoxy radical having in each case 1 to 6 carbon atoms or a heterocylyl radical, heterocyclyloxy radical or heterocyclylamino radical, each of the five last-mentioned radicals being unsubstituted or substituted by one or more radicals from the group consisting of halogen, $(C_1-C_4)$alkoxy, $(C_1-C_4)$haloalkoxy, $(C_1-C_4)$alkylthio, $(C_2-C_4)$alkenyl, $(C_2-C_4)$alkynyl, $(C_2-C_4)$alkenyloxy, $(C_2-C_4)$alkynyloxy, hydroxyl, amino, acylamino, mono- and di-$[(C_1-C_4)alkyl]$amino, nitro, carboxyl, cyano, azido, $[(C_1-C_4)alkoxy]$-carbonyl, $[(C_1-C_4)alkyl]$-carbonyl, formyl, carbamoyl, mono- and di-$[(C_1-C_4)alkyl]$-aminocarbonyl, $(C_1-C_4)$alkylsulfinyl, $(C_1-C_4)$haloalkylsulfinyl, $(C_1-C_4)$alkylsulfonyl, $(C_1-C_4)$haloalkylsulfonyl and, in the case of cyclic radicals, also of $(C_1-C_4)$alkyl and $(C_1-C_4)$haloalkyl, or an acyl radical or $R^2$ and $R^3$ together with the nitrogen atom of the group $NR^2R^3$, are a heterocyclic radical having 3 to 6 ring atoms and 1 to 2 hetero-ring atoms, any further hetero-ring atoms in addition to the nitrogen atom being selected from the group consisting of N, O and S, and the radical being unsubstituted or substituted by one or more radicals from the group consisting of halogen, $(C_1-C_4)$alkyl and oxo, $R^4$ is hydrogen, amino, mono- or di-$[(C_1-C_6)alkyl]$-amino, a hydrocarbon radical or hydrocarbonoxy radical having in each case 1 to 6 carbon atoms or a heterocyclyl radical, heterocyclyloxy radical or heterocyclylamino radical, each of the five last-mentioned radicals being unsubstituted or substituted by one or more radicals from the group consisting of halogen, $(C_1-C_4)$alkoxy, $(C_1-C_4)$haloalkoxy, $(C_1-C_4)$alkylthio, $(C_2-C_4)$alkenyl, $(C_2-C_4)$alkynyl, $(C_2-C_4)$alkenyloxy, $(C_2-C_4)$alkynyloxy, hydroxyl, amino, acylamino, mono- and di-$[(C_1-C_4)alkyl]$-amino, nitro, carboxyl, cyano, azido, $[(C_1-C_4)alkoxy]$-carbonyl, $[(C_1-C_4)alkyl]$-carbonyl, formyl, carbamoyl, mono- and di-$[(C_1-C_4)alkyl]$-aminocarbonyl, $(C_1-C_4)$alkylsulfinyl, $(C_1-C_4)$haloalkylsulfinyl, $(C_1-C_4)$alkylsulfonyl, $(C_1-C_4)$haloalkylsulfonyl, phenyl which is unsubstituted or substituted, phenoxy which is unsubstituted or substituted and, in the case of cyclic radicals, also of $(C_1-C_4)$alkyl and $(C_1-C_4)$haloalkyl, or an acyl radical, $R^5$ and $R^6$ in each case independently of one another are halogen, $NO_2$, CN, SCN or a radical of the formula $X^1-A^1$, $X^1$ being a direct bond or a bivalent group of the formula —O—, —S—, —CO—, —O—CO—, —CO—O—, —NR'—, —NR'—CO— or —CO—NR'—, R' being H or $(C_1-C_4)$-alkyl, and $A^1$ being H or an acyclic hydrocarbon radical having 1 to 6 carbon atoms, a cyclic hydrocarbon radical having 3 to 6 carbon atoms or a heterocyclic radical having 3 to 6 ring atoms and 1 to 3 hetero-ring atoms from the group consisting of N, O and S, each of the three last-mentioned radicals being unsubstituted or substituted by one or more radicals from the group consisting of halogen, $(C_1-C_4)$alkoxy, $(C_1-C_4)$haloalkoxy, $(C_1-C_4)$alkylthio, $(C_2-C_4)$alkenyl, $(C_2-C_4)$-alkynyl, $(C_2-C_4)$alkenyloxy, $(C_2-C_4)$alkynyloxy, hydroxyl, amino, acylamino, mono- and di-$[(C_1-C_4)alkyl]$amino, $(C_3-C_6)$cycloalkylamino, nitro, carboxyl, cyano, azido, heterocyclyl which is unsubstituted or substituted, $[(C_1-C_4)$-alkoxy]-carbonyl, $[(C_1-C_4)alkyl]$-carbonyl, formyl, carbamoyl, mono- and di-$[(C_1-C_4)alkyl]$-aminocarbonyl, phenyl which is unsubstituted or substituted, phenoxy which is unsubstituted or substituted, phenylcarbonyl which is unsubstituted or substituted, $(C_1-C_4)$alkylsulfinyl, $(C_1-C_4)$haloalkylsulfinyl, $(C_1-C_4)$alkylsulfonyl, $(C_1-C_4)$haloalkylsulfonyl and, in the case of cyclic radicals, also of $(C_1-C_4)$alkyl and $(C_1-C_4)$haloalkyl, or $R^5$ and $R^6$ together are an alkylene chain having 2 to 4 carbon atoms which is unsubstituted or substituted by one or more radicals from the group consisting of halogen, $(C_1-C_4)$-alkyl and oxo, $(R^7)_n$ are n radicals $R^7$, which, in the case of n=2, 3, 4 or 5, are identical or different, $R^7$ in each case being halogen, nitro, cyano, thiocyanato or a radical of the formula —$X^2$—$A^2$, in which $X^2$ is a direct bond or a bivalent group of the formula —O—, —S(O)$_q$—, S(O)$_q$—O—, —O—S(O)$_q$—, —CO—, —O—CO—, —CO—O—, —NR"—, —O—NR"—, —NR"—O—, —NR"—CO or —CO—NR"—, q being 0, 1 or 2 and R" being hydrogen, $(C_1-C_6)$alkyl, phenyl or $(C_3-C_6)$-cycloalkyl, and in which $A^2$ is hydrogen or $(C_1-C_6)$alkyl, $(C_2-C_6)$alkenyl, $(C_2-C_6)$alkynyl, $(C_3-C_6)$cycloalkyl, $(C_3-C_6)$ cycloalkenyl, phenyl or heteroaryl, each of the 7 last-mentioned radicals being unsubstituted or substituted by one or more radicals from the group consisting of halogen, hydroxyl, nitro, cyano, amino, acylamino, aminocarbonyl, mono- and di-[($C_1$–$C_4$)alkyl]-amino, mono- and di-[($C_1$–$C_4$)alkyl]-aminocarbonyl, ($C_3$–$C_6$) cycloalkyl, ($C_3$–$C_6$)cycloalkoxy, ($C_1$–$C_6$)alkoxy, ($C_1$–$C_6$)alkylthio, ($C_1$–$C_6$)alkylsulfonyl, ($C_1$–$C_6$) alkyl-carbonyl, ($C_1$–$C_6$)alkoxy-carbonyl, ($C_1$–$C_6$) alkylcarbonyloxy, ($C_3$–$C_6$)cycloalkyl-carbonyl, phenyl, phenoxy, phenylcarbonyl, phenoxycarbonyl, phenylcarbonyloxy, heterocyclyl-($C_1$–$C_6$)alkyl and, in the case of cyclic radicals, also of ($C_1$–$C_6$)alkyl, each of the 20 last-mentioned radicals being unsubstituted or substituted by one or more radicals from the group consisting of halogen, hydroxyl, amino, mono- and di-[($C_1$–$C_4$)alkyl]-amino, nitro, cyano, ($C_1$–$C_4$)alkoxy, ($C_1$–$C_4$)alkylthio, ($C_1$–$C_4$) alkylsulfonyl, ($C_1$–$C_4$)haloalkoxy and, in the case of cyclic radicals, also of ($C_1$–$C_4$)alkyl and ($C_1$–$C_4$)haloalkyl, or two adjacent radicals $R^7$ together are a fused-on cycle having 4 to 6 ring atoms which is carbocyclic or contains 1 to 3 hetero-ring atoms from the group consisting of O, S and N, and which is unsubstituted or substituted by one or more radicals from the group consisting of halogen, ($C_1$–$C_4$)alkyl and oxo, X is a group of the formula —O—, —S(O)$_r$— or —NR*—, r being 0, 1 or 2 and R* being hydrogen or alkyl having 1 to 4 carbon atoms, and n is 0, 1, 2, 3, 4 or 5, heterocyclyl in the radicals in each case containing 3 to 9 ring atoms, preferably 3 to 6 ring atoms, in particular 5 or 6 ring atoms, and 1 to 3 hetero-ring atoms from the group consisting of N, O and S, except for the compounds defined above under a) and b).

Of particular interest are furthermore the novel compounds of the formula (I) and salts thereof, in which $R^1$ is ($C_1$–$C_4$)alkyl
which is unsubstituted or substituted by one or more radicals from the group consisting of halogen, hydroxyl, ($C_1$–$C_4$)alkoxy, ($C_1$–$C_4$)alkylthio and phenyl, or phenyl which is unsubstituted or substituted by one or more radicals from the group consisting of halogen, ($C_1$–$C_4$)alkyl, ($C_1$–$C_4$)haloalkyl, ($C_1$–$C_4$)alkoxy, ($C_1$–$C_4$)haloalkoxy, ($C_1$–$C_4$)alkylthio, nitro, cyano, [($C_1$–$C_2$)alkyl]carbonyl, formyl, carbamoyl, mono- and di-[($C_1$–$C_2$)alkyl]aminocarbonyl and ($C_1$–$C_4$) alkylsulfonyl, $R^2$ and $R^3$ independently of one another are hydrogen, amino, formyl, aminocarbonyl, ($C_1$–$C_4$)alkyl, cyano-($C_1$–$C_4$)alkyl, ($C_1$–$C_4$)alkylamino, di-[($C_1$–$C_4$)alkyl]-amino, halo-($C_1$–$C_4$)alkyl, hydroxy-($C_1$–$C_4$)alkyl, ($C_1$–$C_4$)alkoxy-($C_1$–$C_4$)alkyl, halo($C_1$–$C_4$)alkoxy-($C_1$–$C_4$)alkyl, ($C_2$–$C_6$)alkeny halo-($C_2$–$C_6$)alkenyl, ($C_2$–$C_6$)alkynyl, halo-($C_2$–$C_6$)alkynyl, ($C_1$–$C_4$) alkylamino-($C_1$–$C_4$)alkyl, di-[($C_1$–$C_4$)alkyl]-amino-($C_1$–$C_4$)alkyl, ($C_3$–$C_6$)cycloalkylamino-($C_1$–$C_4$)alkyl, ($C_3$–$C_6$)cycloalkyl, ($C_3$–$C_6$)heterocyclyl-($C_1$–$C_4$)alkyl, the cyclic groups in the 3 last-mentioned radicals being unsubstituted or substituted by one or more radicals from the group consistng of ($C_1$–$C_4$)alkyl, halogen and cyano, or ($C_1$–$C_6$)alkanoylamino, N-[($C_1$–$C_6$) alkanoyl]-N-[($C_1$–$C_4$)alkyl]-amino, ($C_1$–$C_6$) alkanoylamino-($C_1$–$C_4$)alkyl, N-[($C_1$–$C_6$)alkanoyl]-N-[($C_1$–$C_4$)alkyl]-amino-($C_1$–$C_4$)alkyl, phenyl, phenoxy, phenylcarbonyl, phenoxycarbonyl, phenyl-carbonyl-($C_1$–$C_4$)alkyl, ($C_1$–$C_4$)alkoxy-carbonyl-($C_1$–$C_4$)alkyl, ($C_1$–$C_4$)alkylamino-carbonyl-($C_1$–$C_4$)alkyl, ($C_1$–$C_4$) alkyl-carbonyl, ($C_1$–$C_4$)alkoxy-carbonyl, ($C_1$–$C_4$) alkylamino-carbonyl, di-[($C_1$–$C_4$)alkyl]-aminocarbonyl, phenoxy-($C_1$–$C_4$)alkyl, phenyl-($C_1$–$C_4$)alkyl, heterocyclyl, heterocyclylamino, heterocyclyloxy, heterocyclylthio or one of the 21 last-mentioned radicals which is substituted in the acyclic moiety or in the cyclic moiety by one or more radicals from the group consisting of halogen, nitro, cyano, ($C_1$–$C_4$)alkoxy, ($C_1$–$C_4$)alkylthio, ($C_1$–$C_4$) haloalkoxy, formyl, ($C_1$–$C_4$)alkyl-carbonyl, ($C_1$–$C_4$) alkoxy-carbonyl and, in the case of cyclic radicals, also of ($C_1$–$C_4$)alkyl and ($C_1$–$C_4$)haloalkyl, or $R^2$ and $R^3$, together with the nitrogen atom of the group NR$^2$R$^3$, are a heterocyclic radical having 3 to 6 ring atoms and 1 to 2 hetero-ring atoms, any further hetero-ring atoms in addition to the nitrogen atom being selected from the group consisting of N, O and S, and the radical being unsubstituted or substituted by one or more radicals from the group consisting of halogen, ($C_1$–$C_4$)alkyl and oxo, $R^4$ is hydrogen, amino, formyl, aminocarbonyl, ($C_1$–$C_4$) alkyl, cyano-($C_1$–$C_4$)alkyl, ($C_1$–$C_4$)alkylamino, di-[($C_1$–$C_4$)alkyl]-amino, halo-($C_1$–$C_4$)alkyl, hydroxy-($C_1$–$C_4$)alkyl, ($C_1$–$C_4$)alkoxy-($C_1$–$C_4$)alkyl, halo ($C_1$–$C_4$)alkoxy-($C_1$–$C_4$)alkyl, ($C_2$–$C_6$)alkenyl, halo-($C_2$–$C_6$)alkenyl, ($C_2$–$C_6$)alkynyl, halo-($C_2$–$C_6$)alkynyl, ($C_1$–$C_4$)alkylamino-($C_1$–$C_4$)alkyl, di-[($C_1$–$C_4$)alkyl]-amino-($C_1$–$C_4$)alkyl, ($C_3$–$C_9$)cycloalkylamino-($C_1$–$C_4$)alkyl, ($C_3$–$C_9$)cycloalkyl, ($C_3$–$C_9$) heterocyclyl-($C_1$–$C_4$)alkyl, the cyclic groups in the 3 last-mentioned radicals being unsubstituted or substituted by one or more radicals from the group consisting of ($C_1$–$C_4$)alkyl, halogen and cyano or ($C_1$–$C_6$) alkanoylamino, N-[($C_1$–$C_6$)alkanoyl]-N-[($C_1$–$C_4$) alkyl]-amino, ($C_1$–$C_6$)alkanoylamino-($C_1$–$C_4$)alkyl, N-[($C_1$–$C_6$)Alkanoyl]-N-[($C_1$–$C_4$)alkyl]-amino-($C_1$–$C_4$)alkyl, phenyl, phenoxy, phenylcarbonyl, phenoxycarbonyl, phenyl-carbonyl-($C_1$–$C_4$)alkyl, ($C_1$–$C_4$)alkoxy-carbonyl-($C_1$–$C_4$)alkyl, ($C_1$–$C_4$) alkylamino-carbonyl-($C_1$–$C_4$)alkyl, ($C_1$–$C_4$)alkyl-carbonyl, ($C_1$–$C_4$)alkoxy-carbonyl, ($C_1$–$C_4$) alkylamino-carbonyl, di-[($C_1$–$C_4$)alkyl]-aminocarbonyl, phenoxy-($C_1$–$C_4$)alkyl, phenyl-($C_1$–$C_4$)alkyl, heterocyclyl, heterocyclylamino, heterocyclyloxy, heterocyclylthio, or one of the 21 last-mentioned radicals which is substituted in the acyclic moiety or, preferably, in the cyclic moiety by one or more radicals from the group consisting of halogen, nitro, cyano, ($C_1$–$C_4$)alkyl, ($C_1$–$C_4$)alkoxy, ($C_1$–$C_4$)alkylthio, ($C_1$–$C_4$)haloalkyl, ($C_1$–$C_4$) haloalkoxy, formyl, ($C_1$–$C_4$)alkyl-carbonyl, ($C_1$–$C_4$) alkoxy-carbonyl and, in the case of cyclic radicals, also of ($C_1$–$C_4$)alkyl and ($C_1$–$C_4$)haloalkyl, $R^5$ and $R^6$ independently of one another are hydrogen, halogen, hydroxyl, amino, nitro, formyl, aminocarbonyl, carboxyl, cyano, thiocyanato, ($C_1$–$C_4$) alkyl, cyano-($C_1$–$C_4$)alkyl, ($C_1$–$C_4$)alkoxy, ($C_1$–$C_4$) alkylamino, di-[($C_1$–$C_4$)alkyl]-amino, halo-($C_1$–$C_4$) alkyl, hydroxy-($C_1$–$C_4$)alkyl, ($C_1$–$C_4$)alkoxy-($C_1$–$C_4$) alkyl, halo($C_1$–$C_4$)alkyl, halo($C_1$–$C_4$)alkoxy-($C_1$–$C_4$) alkyl, ($C_1$–$C_4$)alkylthio, halo-($C_1$–$C_4$)alkylthio, ($C_2$–$C_6$)alkenyl, halo-($C_2$–$C_6$)alkenyl, ($C_2$–$C_6$)alkynyl, halo-($C_2$–$C_6$)alkynyl, ($C_1$–$C_4$)alkylamino-($C_1$–$C_4$)

alkyl, di-[($C_1$–$C_4$)-amino]-($C_1$–$C_4$)alkyl, ($C_3$–$C_6$) cycloalkylamino-($C_1$–$C_4$)alkyl, ($C_3$–$C_6$)cycloalkyl, heterocyclyl-($C_1$–$C_4$)alkyl having 3 to 6 ring members, the cyclic groups in the 3 last-mentioned radicals being unsubstituted or substituted by one or more radicals from the group consisting of ($C_1$–$C_4$)alkyl, halogen and cyano, or ($C_1$–$C_6$)alkanoylamino, N-[($C_1$–$C_6$) alkanoyl]-N-[($C_1$–$C_4$)alkyl]-amino, ($C_1$–$C_6$) alkanoylamino-($C_1$–$C_4$)alkyl, N-[($C_1$–$C_6$)alkanoyl]-N-[($C_1$–$C_4$)alkyl]-amino-($C_1$–$C_4$)alkyl, phenyl, phenoxy, phenylcarbonyl, phenoxycarbonyl, phenylcarbonyl-($C_1$–$C_4$)alkyl, ($C_1$–$C_4$)alkoxy-carbonyl-($C_1$–$C_4$)alkyl, ($C_1$–$C_4$)alkylamino-carbonyl-($C_1$–$C_4$)alkyl, ($C_1$–$C_4$) alkyl-carbonyl, ($C_1$–$C_4$)alkoxy-carbonyl, ($C_1$–$C_4$) alkylamino-carbonyl, di-[($C_1$–$C_4$)alkyl]-aminocarbonyl, phenoxy-($C_1$–$C_4$)alkyl, phenyl-($C_1$–$C_4$)alkyl, heterocyclyl, heterocyclylamino, heterocyclyloxy, heterocyclthio, or one of the 21 last-mentioned radicals which is substituted in the acyclic moiety or in the cyclic moiety by one or more radicals from the group consisting of halogen, nitro, cyano, ($C_1$–$C_4$)alkoxy, ($C_1$–$C_4$)alkylthio, ($C_1$–$C_4$) haloalkoxy, formyl, ($C_1$–$C_4$)alkyl-carbonyl, ($C_1$–$C_4$) alkoxycarbonyl and, in the case of cyclic radicals, also of ($C_1$–$C_4$)alkyl and ($C_1$–$C_4$)haloalkyl, or $R^5$ and R6 together are an alkylene chain having 2 to 4 carbon atoms which is unsubstituted or substituted by one or more radicals from the group consisting of halogen, ($C_1$–$C_4$)alkyl and oxo, ($R^7$)$_n$ are n radicals $R^7$ which, in the case n=2, 3, 4 and 5, are identical or different, $R^7$ being in each case halogen, hydroxyl, amino, nitro, formyl, aminocarbonyl, aminocarbonyl-($C_1$–$C_4$)alkyl, carboxyl, cyano, thiocyanato or ($C_1$–$C_6$)alkyl, ($C_1$–$C_6$)alkoxy, ($C_1$–$C_6$) alkylthio, ($C_1$–$C_4$)alkylsulfonyl, ($C_1$–$C_6$)cycloalkyl, ($C_2$–$C_6$)alkenyl, ($C_2$–$C_6$)alkynyl, ($C_3$–$C_6$)-cycloalkyl-($C_1$–$C_4$)alkyl, ($C_3$–$C_6$)-cycloalkyl-($C_1$–$C_4$)alkenyl, ($C_3$–$C_6$)cycloalkyl-($C_1$–$C_4$)alkynyl, ($C_1$–$C_6$) alkylcarbonyl, ($C_3$–$C_6$)cycloalkoxy, ($C_3$–$C_6$) cycloalkyl-($C_1$–$C_6$)-alkoxy-carbonyl, ($C_1$–$C_6$)alkyl-carbonyloxy, ($C_1$–$C_6$)alkylcarbonyl-($C_1$–$C_6$)alkyl, ($C_1$–$C_6$)alkoxycarbonyl-($C_1$–$C_6$)alkyl, ($C_1$–$C_6$)alkylcarbonyloxy-($C_1$–$C_6$)-alkyl, ($C_1$–$C_6$) cycloalkoxy-($C_1$–$C_4$)alkyl, ($C_3$–$C_6$) cycloalkylcarbonyl-($C_1$–$C_4$)alkyl, mono-($C_1$–$C_6$) alkylamino, di-[($C_1$–$C_4$)alkyl]amino, ($C_1$–$C_6$) alkanoylamino, N-[($C_1$–$C_6$)alkanoyl]-N-[($C_1$–$C_4$) alkyl]-amino, ($C_1$–$C_6$)alkanoylamino-($C_1$–$C_4$)alkyl or N-[($C_1$–$C_6$)alkanoyl]-N-[($C_1$–$C_4$)alkyl]-amino-($C_1$–$C_4$)alkyl, each of the 26 last-mentioned radicals being substituted in the acyclic moiety or in the cyclic moiety by one or more radicals from the group consisting of halogen, nitro, amino, amino-($C_1$–$C_4$)alkyl, mono- and di-[($C_1$–$C_4$)alkyl]-amino-($C_1$–$C_4$)alkyl, hydroxyl, cyano, ($C_1$–$C_4$)alkoxy, ($C_1$–$C_4$)alkylthio, ($C_1$–$C_4$)haloalkoxy, ($C_1$–$C_4$)alkyl-carbonyl, ($C_1$–$C_4$) alkoxy-carbonyl and, in the case of cyclic radicals, also of ($C_1$–$C_4$)alkyl and ($C_1$–$C_4$)haloalkyl, or phenyl, phenoxy, phenylthio, phenylcarbonyl, phenoxycarbonyl, phenylcarbonyloxy, phenylsulfonyl, phenoxy-($C_1$–$C_6$)-alkyl, phenylcarbonyl-($C_1$–$C_6$)alkyl, phenyloxycarbonyl-($C_1$–$C_6$)alkyl, phenylcarbonyloxy-($C_1$–$C_4$)-alkyl, phenyl-($C_1$–$C_6$)alkyl, phenyl-($C_1$–$C_6$)alkenyl, phenyl-($C_1$–$C_6$)alkynyl, heterocyclyl, heterocyclyloxy, heterocyclylthio, heterocyclylsulfonyl, heterocyclylamino, heterocyclyl-($C_1$–$C_6$)alkyl or one of the 20 last-mentioned radicals which is substituted by one or more radicals from the group consisting of halogen, hydroxyl, nitro, cyano, ($C_1$–$C_6$)alkyl, ($C_1$–$C_6$) alkoxy, ($C_1$–$C_6$)alkylthio, ($C_1$–$C_4$)alkylsulfonyl, ($C_1$–$C_6$)haloalkyl and ($C_1$–$C_6$)haloalkoxy, or two adjacent radicals $R^7$ together are a fused-on cycle having 4 to 6 ring atoms, which is carbocyclic or contains hetero-ring atoms from the group consisting of O, S and N, and which is unsubstituted or substituted by one or more radicals from the group consisting of halogen, ($C_1$–$C_4$)alkyl and oxo, X is a group of the formula —O—, —S— or —NR*—, R* being hydrogen or alkyl having 1 to 4 carbon atoms, and n is 0, 1, 2, 3, 4 or 5, heterocyclyl in the radicals in each case containing 3 to 6 ring atoms and 1 to 3 hetero-ring atoms from the group consisting of N, O and S, except for the compounds defined further above under a) and b).

Preference is given to the novel compounds of the formula (I) and salts thereof, in which $R^1$ is ($C_1$–$C_4$)alkyl, ($C_1$–$C_4$)haloalkyl, ($C_1$–$C_4$) hydroxyalkyl, ($C_1$–$C_4$)alkoxy-($C_1$–$C_4$)-alkyl or benzyl, $R^2$ and $R^3$ independently of one another are hydrogen, amino, formyl, ($C_1$–$C_4$)alkyl, ($C_1$–$C_4$)alkoxy-($C_1$–$C_4$) alkyl, ($C_2$–$C_6$)alkenyl, ($C_2$–$C_6$)alkynyl, ($C_1$–$C_4$) alkylamino-($C_1$–$C_4$)alkyl, di-[($C_1$–$C_4$)alkyl]-amino-($C_1$–$C_4$)alkyl or phenyl, phenyl-($C_1$–$C_4$)alkyl or phenoxy-carbonyl or one of the three last-mentioned radicals which is substituted up to three times in the phenyl moiety by radicals of the group consisting of halogen, ($C_1$–$C_4$)alkyl, ($C_1$–$C_4$)alkoxy and ($C_1$–$C_4$) alkoxy-carbonyl, or $R^2$ and $R^3$, together with the nitrogen atom of the group $NR^2R^3$, are a heterocyclic radical having 3 to 6 ring atoms and 1 to 2 hetero-ring atoms, any further hetero-ring atoms in addition to the nitrogen atom being selected from the group consisting of N and O, and the radical being unsubstituted or substituted by one or more radicals from the group consisting of halogen, ($C_1$–$C_4$)alkyl and oxo, $R^4$ is hydrogen, amino, formyl, ($C_1$–$C_4$)alkyl, di-[($C_1$–$C_4$) alkyl]-amino, ($C_1$–$C_4$)alkoxy-($C_1$–$C_4$)alkyl, ($C_2$–$C_6$) alkenyl, ($C_2$–$C_6$)alkynyl, ($C_1$–$C_4$)dialkylamino-($C_1$–$C_4$)alkyl, phenyl, phenoxy-($C_1$–$C_4$)alkyl, phenyl-($C_1$–$C_4$)alkyl, phenoxy-carbonyl, phenylaminocarbonyl or one of the five last-mentioned radicals which is mono- to trisubstituted in the phenyl moiety by radicals from the group consisting of halogen, ($C_1$–$C_4$)alkyl, ($C_1$–$C_4$)alkoxy and ($C_1$–$C_4$)alkoxycarbonyl, $R^5$ and $R^6$ independently of one another are hydrogen, ($C_1$–$C_4$)alkyl, ($C_3$–$C_6$)cycloalkyl, ($C_1$–$C_4$)alkoxy-($C_1$–$C_4$)alkyl, ($C_2$–$C_6$)alkenyl, ($C_2$–$C_6$)alkynyl, di-[($C_1$–$C_4$)-alkyl]amino-($C_1$–$C_4$)alkyl, phenyl, phenoxy-($C_1$–$C_4$)alkyl, phenyl-($C_1$–$C_4$)alkyl or one of the three last-mentioned radicals which is mono- to trisubstituted in the phenyl moiety by radicals from the group consisting of halogen, ($C_1$–$C_4$)alkyl, ($C_1$–$C_4$)alkoxy and ($C_1$–$C_4$)alkoxy-carbonyl, or $R^5$ and $R^6$ together are an alkylene chain having 2 to 4 carbon atoms which is unsubstituted or substituted by one or more radicals from the group consisting of halogen, ($C_1$–$C_4$)alkyl and oxo, ($R^7$)$_n$ are n radicals $R^7$ which, in the case of n=2, 3, 4 or 5, are identical or different, $R^7$ in each case being halogen, hydroxyl, amino, nitro, formyl, aminocarbonyl, carboxyl, cyano, thiocyanato, $(C_1-C_6)$alkyl, $(C_1-C_4)$alkoxy, halo-$(C_1-C_4)$alkyl, halo-$(C_1-C_4)$alkoxy, hydroxy-$(C_1-C_4)$alkyl, hydroxy-$(C_1-C_4)$alkoxy, $(C_1-C_4)$alkoxy-$(C_1-C_4)$alkyl, $(C_1-C_4)$alkoxy-$(C_1-C_4)$-alkoxy, halo-$(C_1-C_4)$alkoxy-$(C_1-C_4)$alkyl, halo-$(C_1-C_4)$alkoxy-$(C_1-C_4)$alkoxy, $(C_3-C_6)$cycloalkyl, halo-$(C_3-C_6)$cycloalkyl, $(C_2-C_6)$alkenyl, halo-$(C_2-C_6)$alkenyl, $(C_2-C_6)$alkynyl, halo-$(C_2-C_6)$alkynyl, $(C_1-C_4)$alkylcarbonyl, $(C_1-C_4)$haloalkylcarbonyl, $(C_3-C_6)$cycloalkyloxy, halo-$(C_3-C_6)$cycloalkyloxy, $(C_3-C_6)$cycloalkylcarbonyl, halo-$(C_3-C_6)$cycloalkylcarbonyl, $(C_1-C_4)$alkoxycarbonyl, halo-$(C_1-C_4)$alkoxycarbonyl, $(C_1-C_4)$alkylcarbonyloxy, halo-$(C_1-C_4)$alkylcarbonyloxy, $(C_1-C_4)$alkylcarbonyl-$(C_1-C_4)$alkyl, $(C_1-C_4)$alkoxycarbonyl-$(C_1-C_4)$alkyl, $(C_1-C_4)$alkylcarbonyloxy-$(C_1-C_4)$alkyl, $(C_1-C_4)$alkylthio, halo-$(C_1-C_4)$alkylthio, $(C_1-C_4)$alkylamino, di-[$(C_1-C_4)$alkyl]-amino, $(C_1-C_6)$alkanoylamino, N-[$(C_1-C_6)$alkanoyl]-N-[$(C_1-C_4)$alkyl]-amino, $(C_1-C_6)$alkanoylamino-$(C_1-C_4)$alkyl, N-[$(C_1-C_6)$alkanoyl]-N-[$(C_1-C_4)$alkyl]-amino-$(C_1-C_4)$alkyl or phenyl, phenoxy, phenylcarbonyl, phenoxycarbonyl, phenylcarbonyloxy, phenoxy-$(C_1-C_4)$alkyl, phenylcarbonyl-$(C_1-C_4)$alkyl, phenyl-$(C_1-C_4)$alkyl, phenyl-$(C_2-C_6)$-alkenyl, phenyl-$(C_2-C_6)$alkynyl, heterocyclyl, heterocyclyloxy, heterocyclylthio, heterocyclylamino, heterocyclyl-$(C_1-C_4)$alkyl, or one of the 15 last-mentioned radicals which is substituted in the cyclic moiety by one or more radicals from the group consisting of halogen, hydroxyl, nitro, $(C_1-C_4)$alkyl, $(C_1-C_4)$alkoxy, $(C_1-C_4)$alkylthio, $(C_1-C_4)$-haloalkyl and $(C_1-C_4)$haloalkoxy, or two adjacent radicals $R^7$ together are a fused-on cycle having 4 to 6 ring atoms which is carbocyclic or contains hetero-ring atoms from the group consisting of O, S and N, and which is unsubstituted or substituted by one or more radicals from the group consisting of halogen, $(C_1-C_4)$alkyl and oxo, X is a group of the formula —O— or —NR*—, R* being hydrogen or methyl, and n is 0, 1, 2, 3, 4 or 5, heterocyclyl in the radicals in each case containing 3 to 6 ring atoms and 1 to 3 hetero-ring atoms from the group consisting of N, O and S, preferably N and O, except for the compounds defined above under a) and b).

Preference is furthermore given to the novel compounds of the formula (I) and salts thereof as claimed in any of claims 1 to 4, wherein $R^1$ is $(C_1-C_4)$alkyl, $(C_1-C_4)$haloalkyl, $(C_1-C_4)$hydroxyalkyl or $(C_1-C_4)$alkoxy-$(C_1-C_4)$alkyl, $R^2$ and $R^3$ independently of one another are hydrogen, amino, formyl or $(C_1-C_4)$alkyl or $R^2$ and $R^3$, together with the nitrogen atom of the group NR$^2$R$^3$, are a heterocyclic radical having 4 to 6 ring atoms which, in addition to the nitrogen atom, may contain a further hetero-ring atom from the group consisting of N and O as hetero-ring atom, $R^4$ is hydrogen or $(C_1-C_4)$alkyl, $R^5$ is hydrogen, $(C_1-C_4)$alkyl, $(C_2-C_4)$alkenyl, $(C_2-C_4)$alkynyl, $(C_3-C_6)$cycloalkyl $(C_1-C_4)$alkoxy-$(C_1-C_4)$alkyl or phenyl, preferably methyl, ethyl, n-propyl, isopropyl or cyclopropyl, and $R^6$ is hydrogen, $(C_1-C_4)$alkyl, $(C_2-C_4)$alkenyl, $(C_2-C_4)$alkynyl, $(C_3-C_6)$cycloalkyl $(C_1-C_4)$alkoxy-$(C_1-C_4)$alkyl or phenyl, preferably hydrogen, or $R^5$ and $R^6$ together are an alkylene chain having 2 to 4 carbon atoms, $R^7$ independently of one another are halogen, hydroxyl, amino, nitro, formyl, carboxyl, cyano, $(C_1-C_6)$alkyl, $(C_1-C_4)$alkoxy, halo-$(C_1-C_4)$alkyl, halo-$(C_1-C_4)$alkoxy, hydroxy-$(C_1-C_4)$alkyl, hydroxy-$(C_1-C_4)$alkoxy, $(C_1-C_4)$alkoxy-$(C_1-C_4)$alkyl, halo-$(C_1-C_4)$alkoxy-$(C_1-C_4)$alkyl, halo-$(C_1-C_4)$alkyloxy-$(C_1-C_4)$-alkoxy, $(C_1-C_4)$alkoxy-$(C_1-C_4)$alkoxy, $(C_3-C_6)$cycloalkyl, halo-$(C_3-C_6)$cycloalkyl, $(C_2-C_6)$alkenyl, halo-$(C_2-C_6)$alkenyl, $(C_2-C_6)$alkynyl, halo-$(C_2-C_6)$alkynyl, $(C_1-C_4)$alkylcarbonyl, halo-$(C_1-C_4)$alkylcarbonyl, $(C_1-C_4)$alkoxycarbonyl, halo-$(C_1-C_4)$alkoxycarbonyl, $(C_1-C_4)$alkylcarbonyloxy, halo-$(C_1-C_4)$alkyl-carbonyloxy, $(C_1-C_4)$alkylcarbonyl-$(C_1-C_4)$alkyl, $(C_1-C_4)$alkylthio, halo-$(C_1-C_4)$alkylthio, $(C_1-C_4)$alkylamino, di-[$(C_1-C_4)$-alkyl]-amino, phenyl, phenoxy, phenylcarbonyl, phenoxycarbonyl, phenylcarbonyloxy, phenoxy-$(C_1-C_4)$alkyl, phenylcarbonyl-$(C_1-C_4)$alkyl, phenyl-$(C_1-C_4)$alkyl, phenyl-$(C_2-C_4)$alkenyl, phenyl-$(C_2-C_4)$alkynyl, heterocyclyl, heterocyclyloxy, heterocyclylthio, heterocyclylamino or one of the 14 last-mentioned radicals which is substituted in the cyclic moiety by one or more radicals from the group consisting of halogen, $(C_1-C_4)$alkyl, $(C_1-C_4)$alkoxy, $(C_1-C_4)$haloalkyl and $(C_1-C_4)$haloalkoxy, heterocyclyl in the radicals having 3 to 6 ring atoms and 1 to 3 hetero-ring atoms from the group consisting of N and O, or two adjacent radicals $R^7$ together are a fused-on cycle having 4 to 6 ring atoms, which is carbocyclic or contains hetero-ring atoms from the group consisting of O and N, and which is unsubstituted or substituted by one or more radicals $(C_1-C_4)$alkyl, X is a group of the formula —O— or —NH— and n is 0, 1, 2, 3, 4 or 5, except for the compounds mentioned above under a) and b).

Particular preference is furthermore given to the novel compounds of the formula (I) and salts thereof, in which a1) $R^1$ is $(C_1-C_6)$haloalkyl, preferably $(C_1-C_4)$haloalkyl, $R^2$, $R^3$, $R^4$, $R^6$ are each hydrogen, $R^5$ is methyl, n is the number 3, 4 or 5, X is an oxygen atom and $(R^7)_n$ are n radicals $R^7$ which are identical or different, $R^7$ in each case being halogen, hydroxyl, amino, nitro, formyl, carboxyl, cyano, $(C_1-C_6)$alkyl, $(C_1-C_4)$alkoxy, halo-$(C_1-C_4)$alkyl, halo-$(C_1-C_4)$alkoxy, hydroxy-$(C_1-C_4)$alkyl, hydroxy-$(C_1-C_4)$alkoxy, $(C_1-C_4)$alkoxy-$(C_1-C_4)$alkyl, halo-$(C_1-C_4)$alkoxy-$(C_1-C_4)$alkyl, halo-$(C_1-C_4)$alkyloxy-$(C_1-C_4)$-alkoxy, $(C_1-C_4)$alkoxy-$(C_1-C_4)$alkoxy, $(C_3-C_6)$cycloalkyl, halo-$(C_3-C_6)$cycloalkyl, $(C_2-C_4)$alkenyl, halo-$(C_2-C_4)$alkenyl, $(C_2-C_4)$alkynyl, halo-$(C_2-C_4)$alkynyl, $(C_1-C_4)$alkylcarbonyl, $(C_1-C_4)$alkoxycarbonyl, $(C_1-C_4)$alkylcarbonyloxy, $(C_1-C_4)$alkylcarbonyl-$(C_1-C_4)$alkyl, $(C_1-C_4)$alkylthio, $(C_1-C_4)$aikylamino, di-[$(C_1-C_4)$-alkyl]-amino or phenyl, phenoxy, phenylcarbonyl, phenoxycarbonyl, phenylcarbonyloxy, phenoxy-$(C_1-C_4)$alkyl, phenylcarbonyl-$(C_1-C_4)$alkyl, phenyl-$(C_1-C_4)$alkyl or one of the 8 last-mentioned radicals which is substituted in the phenyl moiety by one or more radicals from the group consisting of halogen, $(C_1-C_4)$alkyl, $(C_1-C_4)$alkoxy, $(C_1-C_4)$haloalkyl and $(C_1-C_4)$haloalkoxy, or two adjacent radicals $R^7$ together are a fused-on cycle having 4 to 6 ring atoms, which is carbocyclic or contains one or two hetero-ring atoms from the group consisting of O and N, and which is unsubstituted or substituted by one or more radicals $(C_1-C_4)$alkyl, or a2) $R^1$ is $(C_1-C_6)$haloalkyl, preferably $(C_1-C_4)$haloalkyl, $R^2$, $R^3$, $R^4$, $R^6$ are each hydrogen,
$R^5$ is methyl,
n is the number 1 or 2,
X is an oxygen atom,
$(R^7)_n$ are n radicals $R^7$ which, in the case of n=2, are defined the same, $R^7$ in each case being chlorine, bromine, iodine, hydroxyl, amino, nitro, formyl, carboxyl, cyano, $(C_2-C_4)$alkoxy, methyl which is substituted by one or more radicals from the group consisting of chlorine, bromine and iodine, $(C_2-C_4)$haloalkyl, halo-$(C_1-C_4)$alkoxy, hydroxy-$(C_1-C_4)$alkyl, hydroxy-$(C_1-C_4)$alkoxy, $(C_1-C_4)$alkoxy-$(C_1-C_4)$alkyl, halo-$(C_1-C_4)$alkoxy-$(C_1-C_4)$alkyl, halo-$(C_1-C_4)$alkyloxy-$(C_1-C_4)$-alkoxy, $(C_1-C_4)$alkoxy-$(C_1-C_4)$alkoxy, $(C_3-C_6)$cycloalkyl, halo-$(C_3-C_6)$cycloalkyl, $(C_2-C_4)$alkenyl, halo-$(C_2-C_4)$alkenyl, $(C_2-C_4)$alkynyl, halo-$(C_2-C_4)$alkynyl, $(C_1-C_4)$alkylcarbonyl, $(C_1-C_4)$alkoxycarbonyl, $(C_1-C_4)$alkylcarbonyloxy, $(C_1-C_4)$alkylcarbonyl-$(C_1-C_4)$alkyl, $(C_1-C_4)$alkylthio, halo-$(C_1-C_4)$alkylthio, $(C_1-C_4)$alkylamino, di-[$(C_1-C_4)$-alkyl]-amino or phenyl, phenoxy, phenylcarbonyl, phenoxycarbonyl, phenylcarbonyloxy, phenoxy-$(C_1-C_4)$alkyl, phenylcarbonyl-$(C_1-C_4)$alkyl, phenyl-$(C_1-C_4)$alkyl or one of the 8 last-mentioned radicals which is substituted in the phenyl moiety by one or more radicals from the group consisting of halogen, $(C_1-C_4)$alkyl, $(C_1-C_4)$alkoxy, $(C_1-C_4)$haloalkyl and $(C_1-C_4)$haloalkoxy, or two adjacent radicals $R^7$ together are a fused-on cycle having 4 to 6 ring atoms, which is carbocyclic or contains 1 or 2 hetero-ring atoms from the group consisting of O and N, and which is unsubstituted or substitued by one or more radicals $(C_1-C_4)$alkyl, or a3) $R^1$ is $(C_1-C_6)$haloalkyl, preferably $(C_1-C_4)$haloalkyl, $R^2$, $R^3$, $R^4$, $R^6$ are each hydrogen,
$R^5$ is methyl,
n is the number 2,
X is an oxygen atom and
$(R^7)_n$ are the two radicals $R^7$, the two radicals $R^7$ being structurally different and otherwise as defined above under al), or else two adjacent radicals $R^7$ together are a fused-on cycle having 4 to 6 ring atoms, which is carbocyclic or contains 1 or 2 hetero-ring atoms from the group consisting of O and N, and which is unsubstituted or substituted by one or more radicals $(C_1-C_4)$alkyl, or b1) $R^1$ is $(C_1-C_6)$alkyl, preferably $(C_1-C_4)$alkyl, which is unsubstituted or substituted by 1 to 4 substituents from the group consisting of $(C_1-C_4)$alkoxy and hydroxyl, $R^2$, $R^3$, $R^4$, $R^6$ are each hydrogen,
$R^5$ is methyl,
n is the number 1, 2, 3 or 4,
X is an oxygen atom and
$(R^7)_n$ are n radicals $R^7$ which, in the case of n=2, 3 or 4, are identical or different, $R^7$ in each case being hydroxyl, amino, nitro, formyl, carboxyl, cyano, $(C_1-C_4)$alkoxy, halo-$(C_1-C_4)$alkyl, halo-$(C_1-C_4)$alkoxy, hydroxy-$(C_1-C_4)$alkyl, hydroxy-$(C_1-C_4)$ alkoxy, $(C_1-C_4)$alkoxy-$(C_1-C_4)$alkyl, halo-$(C_1-C_4)$alkoxy-$(C_1-C_4)$alkyl, halo-$(C_1-C_4)$alkyloxy-$(C_1-C_4)$-alkoxy, $(C_1-C_4)$alkoxy-$(C_1-C_4)$alkoxy, $(C_3-C_3)$cycloalkyl, halo-$(C_3-C_6)$cycloalkyl, $(C_2-C_4)$alkenyl, halo-$(C_2-C_4)$alkenyl, $(C_2-C_4)$alkynyl, halo-$(C_2-C_4)$alkynyl, $(C_1-C_4)$alkylcarbonyl, $(C_1-C_4)$alkoxycarbonyl, $(C_1-C_4)$alkylcarbonyloxy, $(C_1-C_4)$alkylcarbonyl-$(C_1-C_4)$alkyl, $(C_1-C_4)$alkylthio, halo-$(C_1-C_4)$alkylthio, $(C_1-C_4)$alkylamino, di-[$(C_1-C_4)$-alkyl]-amino or phenyl, phenoxy, phenylcarbonyl, phenoxycarbonyl, phenylcarbonyloxy, phenoxy-$(C_1-C_4)$alkyl, phenylcarbonyl-$(C_1-C_4)$alkyl, phenyl-$(C_1-C_4)$alkyl or one of the 8 last-mentioned radicals which is substituted in the phenyl moiety by one or more radicals from the group consisting of halogen, $(C_1-C_4)$alkyl, $(C_1-C_4)$alkoxy, $(C_1-C_4)$haloalkyl and $(C_1-C_4)$haloalkoxy, or two adjacent radicals $R^7$ together are a fused-on cycle having 4 to 6 ring atoms, which is carbocyclic or contains 1 or 2 hetero-ring atoms from the group consisting of O and N. and which is unsubstituted or substituted by one or more radicals $(C_1-C_4)$alkyl.

The present invention also provides processes for preparing the novel compounds of the formula (I) or salts thereof, which comprise a) reacting a compound of the formula (II),

$R^1$-Fu    (II)

in which Fu is a functional group from the group consisting of carboxylate, carboxylic acid ortho ester, carbonyl chloride, carboxamide, carboxylic anhydride and trichloromethyl with a biguanidide of the formula (III) or an acid addition salt thereof

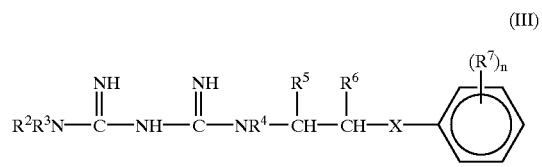

or b) reacting a compound of the formula (IV)

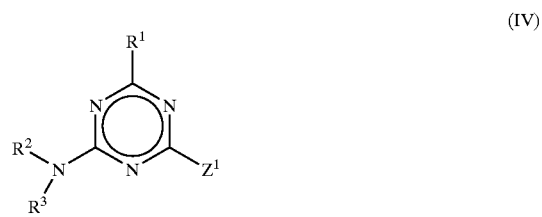

in which $Z^1$ is an exchangeable radical or a leaving group, with a suitable amine of the formula (V) or an acid addition salt thereof

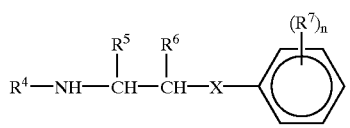
(V)

where, in the formulae (II), (III), (IV) and (V), the radicals $R^1$ to $R^7$ and X and also n are as defined for formula (I).

The reaction of the compounds of the formula (II) and (III) preferably takes place with base catalysis in an inert organic solvent, for example tetrahydrofuran (THF), dioxane, acetonitrile, dimethylformamide (DMF), methanol and ethanol, at temperatures between −10° C. and the boiling point of the solvent, preferably at from 20° C. to 60° C.; if acid addition salts of the formula (III) are used, these are generally liberated in situ with the aid of a base. Suitable bases or basic catalysts are alkali metal hydroxides, alkali metal hydrides, alkali metal carbonates, alkali metal alcoholates, alkaline earth metal hydroxides, alkaline earth metal hydrides, alkaline earth metal carbonates or organic bases such as triethylamine or 1,8-diazabicyclo[5.4.0]undec-7-ene (DBU). In this context the respective base is employed, for example, in the range from 0.1 to 3 mole equivalents relative to the compound of the formula (III). The compound of the formula (II) can, for example, be employed relative to the compound of the formula (III), in an equimolar quantity or with an excess of up to 2 mole equivalents. In principle, the appropriate methods are known in the literature (compare: Comprehensive Heterocyclic Chemistry, A. R. Katritzky, C. W. Rees, Pergamon Press, Oxford, N.Y., 1984, Vol.3; Part 2B; ISBN 0-08-030703-5, p.290).

The reaction of the compounds of the formula (IV) and (V) preferably takes place with base catalysis in an inert organic solvent, for example THF, dioxane, acetonitrile, DMF, methanol and ethanol, at temperatures between −10° C. and the boiling point of the respective solvent or solvent mixture, preferably at from 20° C. to 60° C., the compound (V), if employed as acid addition salt, being liberated if appropriate in situ with a base. Suitable bases or basic catalysts are alkali metal hydroxides, alkali metal hydrides, alkali metal carbonates, alkali metal alcoholates, alkaline earth metal hydroxides, alkaline earth metal hydrides, alkaline earth metal carbonates or organic bases such as triethylamine or 1,8-diazabicyclo[5.4.0]undec-7-ene (DBU). In this context the respective base is generally employed in the range from 1 to 3 mole equivalents relative to the compound of the formula (IV), while the compound of the formula (IV) can, for example, be employed in equimolar quantities relative to the compound of the formula (V) or with an excess of up to 2 mole equivalents. In principle, the appropriate methods are known from the literature (cf. Comprehensive Heterocyclic Chemistry, A. R. Katritzky, C. W. Rees, Pergamon Press, Oxford, N.Y., 1984, Vol.3; Part 2B; ISBN 0-08-030703-5, p. 482).

The precursors of the formulae (II), (III), (IV) and (V) are either commercially available or can be prepared by or in accordance with methods known from the literature. Examples of suitable preparations are described below.

The compounds (II), (III) and (V) can be prepared, for example, by or in accordance with the processes described in EP-A-0492615, EP-A-0509544 and EP-A-0506059 and the literature cited therein.

The compound of the formula (IV), or a direct precursor thereof, can be prepared, for example, as follows:

1. By reaction of a compound of the formula (II) with an amidino-thiourea derivative of the formula (VI),

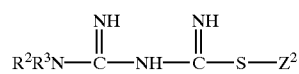
(VI)

in which $Z^2$ is $(C_1–C_4)$-alkyl or phenyl-$(C_1–C_4)$-alkyl and $R^2$ and $R^3$ are as defined for formula (I), giving compounds of the formula (IV) in which $Z^1$ is $—SZ^2$.

2. By reaction of an amidine of the formula (VII) or an acid addition salt thereof,

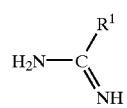
(VII)

in which $R^1$ is as defined for formula (I),
with an N-cyano dithioiminocarbonate of the formula (VIII),

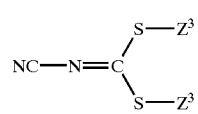
(VIII)

in which $Z^3$ is $(C_1–C_4)$-alkyl or phenyl-$(C_1–C_4)$-alkyl, giving compounds of the formula (IV) in which $Z^1$ is $—S—Z^3$.

3. By reaction of an alkali metal dicyanamide with a carboxylic acid derivative of the abovementioned formula (II), giving compounds of the formula (IV) in which $Z^1$ is $NH_2$.

4. By reaction of trichloroacetonitrile with a nitrile of the formula (IX)

$R^1$-CN (IX)

in which $R^1$ is as defined in formula (I), giving firstly compounds of the formula (X),

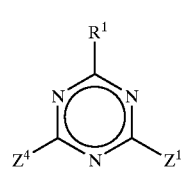
(X)

in which $Z^1$ and $Z^4$ are each $CCl_3$, which by subsequent reaction with compounds of the formula $HNR^2R^3$ ($R^2$ and $R^3$ as in formula (I)) lead to compounds of the formula (IV), in which $Z^1$ is $CCl_3$.

The reaction of the carboxylic acid derivatives of the formula (II) with the amidinothiourea derivatives of the formula (VI) preferably takes place with base catalysis in an organic solvent, for example acetone, THF, dioxane, acetonitrile, DMF, methanol and ethanol, at temperatures from −10° C. to the boiling point of the solvent, preferably at from 0° C. to 20° C. However, the reaction can also be carried out in water or in aqueous solvent mixtures with one or more of the abovementioned organic solvents. If the compound (VI) is employed as acid addition salt, it can if desired be liberated in situ with a base. Suitable bases or basic catalysts are alkali metal hydroxides, alkali metal hydrides, alkali metal carbonates, alkali metal alcoholates, alkaline earth metal hydroxides, alkaline earth metal hydrides, alkaline earth metal carbonates or organic bases such as triethylamine or 1,8-diazabicyclo[5.4.0]undec-7-ene (DBU). In this context the respective base is employed in the range from 1 to 3 mole equivalents relative to the compound of the formula (VI). Compounds of the formula (II) and (VI) can, for example, be employed in equimolar quantities or with an excess of up to 2 mole equivalents of compound of the formula (II). In principle the appropriate methods are known from the literature (cf.: H. Eilingsfeld, H. Scheuermann, Chem. Ber.; 1967, 100, 1874).

The reaction of the amidines of the formula (VII) with the N-cyano dithioiminocarbonates of the formula (VIII) preferably takes place with base catalysis in an inert organic solvent, for example acetonitrile, DMF, dimethylacetamide (DMA), N-methylpyrrolidone (NMP), methanol and ethanol, at temperatures from −10° C. to the boiling point of the solvent, preferably at from 20° C. to 80° C. If (VII) is employed as acid addition salt, it can if desired be liberated in situ with a base. Suitable bases or basic catalysts are alkali metal hydroxides, alkali metal hydrides, alkali metal carbonates, alkali metal alcoholates, alkaline earth metal hydroxides, alkaline earth metal hydrides, alkaline earth metal carbonates or organic bases such as triethylamine or 1,8-diazabicyclo[5.4.0]undec-7-ene (DBU). In this context the respective base is employed, for example, in the range from 1 to 3 mole equivalents relative to the compound of the formula (VIII); compounds of the formula (VII) and (VIII) can in general be employed in equimolar quantities or with an excess of 2 mole equivalents of compound of the formula (II). In principle the appropriate methods are known from the literature (cf.: T. A. Riley, W. J. Henney, N. K. Dalley, B. E. Wilson, R. K. Robins; J. Heterocyclic Chem.; 1986, 23 (6), 1706–1714).

Intermediates of the formula (X) where $Z^1$=chlorine can be prepared by reacting alkali metal dicyanamide with a carboxylic acid derivative of the formula (II), in which case Fu is preferably the functional group carbonyl chloride or carboxamide. The reaction components are, for example, reacted with acid catalysis in an inert organic solvent such as toluene, chlorobenzene or chlorinated hydrocarbons at temperatures between −10° C. and the boiling point of the solvent, preferably at from 20° C. to 80° C., it being possible to chlorinate the resulting intermediates in situ using an appropriate chlorinating reagent, for example phosphorus oxychloride. Examples of suitable acids are hydrohalic acids such as HCl or else Lewis acids, for example $AlCl_3$ or $BF_3$ (cf. U.S. Pat. No. 5,095,113, DuPont).

Intermediates of the formula (X) where $Z^1$, $Z^4$=trihalomethyl can be prepared by reacting the corresponding trihaloacetonitriles with a carbonitrile of the formula (IX). The reaction components are, for example, reacted with acid catalysis in an inert organic solvent such as toluene, chlorobenzene or chlorinated hydrocarbons at temperatures between −40° C. and the boiling point of the solvent, preferably at from −10° C. to 30° C. Examples of suitable acids are hydrohalic acids such as HCl or else Lewis acids such as $AlCl_3$ or $BF_3$ (cf. EP-A-1 30939, Ciba Geigy).

Intermediates of the formula (IV), in which $Z^1$=($C_1$–$C_4$) alkylmercapto or unsubstituted phenyl-($C_1$–$C_4$)-alkylmercapto, can be converted in an inert organic solvent, for example toluene, chlorobenzene, chlorinated hydrocarbons or others, at temperatures between −40° C. and the boiling point of the solvent, preferably at from 20° C. to 80° C., using an appropriate chlorinating reagent, for example elemental chlorine or phosphorus oxychloride, to more reactive chlorotriazines of the formula (IV), in which $Z^1$ is Cl (cf. J. K. Chakrabarti, D. E. Tupper; Tetrahedron 1975, 31(16), 1879–1882).

Intermediates of the formula (IV), in which $Z^1$=($C_1$–$C_4$) alkylmercapto or unsubstituted or substituted phenyl-($C_1$–$C_4$)-alkylmercapto or ($C_1$–$C_4$)alkyl-phenylthio can be oxidized in an appropriate solvent, for example chlorinated hydrocarbons, acetic acid, water, alcohols, acetone or mixtures thereof, at temperatures between 0° C. and the boiling point of the solvent, preferably from 20° C. to 80° C., using a suitable oxidation reagent such as m-chloroperbenzoic acid, hydrogen peroxide, potassium peroxomonosulfate (cf.: T. A. Riley, W. J. Henney, N. K. Dailey, B. E. Wilson, R. K. Robins; J. Heterocyclic Chem.; 1986, 23 (6), 1706–1714).

For the preparation of the acid addition salts of the compounds of the formula (I), suitable acids are the following: hydrohalic acids such as hydrochloric acid or hydrobromic acid, and also phosphoric acid, nitric acid, sulfuric acid, mono- or bifunctional carboxylic acids and hydroxycarboxylic acids such as acetic acid, maleic acid, succinic acid, fumaric acid, tartaric acid, citric acid, salicylic acid, sorbic acid or lactic acid, and also sulfonic acids such as p-toluenesulfonic acid or 1,5-naphthalenedisulfonic acid. The acid addition compounds of the formula (I) can be obtained in a simple manner by the customary methods of forming salts, for example by dissolving a compound of the formula (I) in an appropriate organic solvent such as, for example, methanol, acetone, methylene chloride or benzine and adding the acid at temperatures from 0 to 100° C., and can be isolated in a known manner, for example by filtration, and can if desired be purified by washing with an inert organic solvent.

The base addition salts of the compounds of formula (I) are preferably prepared in inert polar solvents such as, for example, water, methanol or acetone at temperatures from 0 to 100° C. Examples of suitable bases for preparing the salts according to the invention are alkali metal carbonates, such as potassium carbonate, alkali metal hydroxides and alkaline earth metal hydroxides, for example NaOH or KOH, alkali metal hydrides and alkaline earth metal hydrides, for example NaH, alkali metal alcoholates and alkaline earth metal alcoholates, for example sodium methoxide and potassium tert-butoxide, or ammonia or ethanolamine.

By the "inert solvents" mentioned in the above process variants, solvents are meant which are in each case inert under the respective reaction conditions but which need not be inert under any reaction conditions.

The novel compounds of the formula (I) and the salts thereof, referred to together below as (novel) compounds of the formula (I), have an outstanding herbicidal activity against a broad spectrum of economically important monocotyledonous and dicotyledonous weeds. The active compounds also act effectively against difficult-to-control perennial weeds which produce shoots from rhizomes, rootstocks or other perennial organs. In this context it does not matter whether the substances are applied before sowing, pre-emergence or post-emergence.

Individually, examples may be mentioned of some representatives of the monocotyledonous and dicotyledonous weed flora which can be controlled by the compounds according to the invention, without such mention being intended to restrict the invention to specific species.

Examples of monocotyledonous weed species against which the active compounds act effectively are Avena, Lolium, Alopecurus, Phalaris, Echinochloa, Digitaria, Setaria and Cyperus species from the annual group and, among the perennial species, Agropyron, Cynodon, Imperata and Sorghum and also perennial Cyperus species.

In the case of dicotyledonous weed species, the spectrum of action extends to species such as, for example, Galium, Viola, Veronica, Lamium, Stellaria, Amaranthus, Sinapis, lpomoea, Matricaria, Abutilon and Sida among the annuals and Convolvulus, Cirsium, Rumex and Artemisia among the perennial weeds.

The novel active compounds also display outstanding control of weeds which occur under the specific growing conditions in rice, examples being Sagittaria, Alisma, Eleocharis, Scirpus and Cyperus.

Where the novel compounds are applied to the surface of the soil before germination, either the weed seedlings are prevented completely from emerging, or the weeds grow until they reach the cotyledon stage, but then stop growing and, finally, die off completely after three to four weeks have elapsed.

Where the active compounds are applied post-emergence to the green parts of plants, there is likewise a very rapid and drastic termination of growth after treatment, and the weed plants remain at the growth stage they were at at the time of application, or die off completely after a certain time, so that in this manner competition from weeds, which is damaging to the crop plants, is eliminated very early on and in a sustained manner.

Even though the novel compounds have an excellent herbicidal activity with respect to monocotyledonous and dicotyledonous weeds, crop plants of economically important crops, for example wheat, barley, rye, rice, maize, sugar beet, cotton and soya, suffer only minimal or zero damage. For these reasons the present compounds are highly suitable for the selective control of unwanted plant growth in crops of agriculturally useful plants.

Furthermore, the substances according to the invention exhibit outstanding growth-regulating properties in crop plants. They intervene with a regulatory action in the endogenous plant metabolism and can therefore be employed for the targeted control of plant contents and for facilitating the harvest, for example by provoking desiccation and stunted growth. Moreover, they are also suitable for generally controlling and inhibiting unwanted vegetative growth without killing the plants in doing so. In the case of numerous monocotyledonous and dicotyledonous crops, inhibition of vegetative growth plays an important role, since it allows falling over to be reduced or prevented completely.

The novel compounds can be applied in the customary formulations in the form of wettable powders, emulsifiable concentrates, sprayable solutions, dusts or granules. The invention therefore also provides herbicidal and plant growth-regulating compositions comprising compounds of the formula (I).

The compounds of the formula (I) can be formulated in various ways depending on the prevailing biological and/or chemico-physical parameters. Examples of suitable formulation options are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, capsule suspensions (CS), dusts (DP), seed-dressing compositions, granules for broadcasting and soil application, granules (GR) in the form of microgranules, spray granules, coating granules and adsorption granules, water-dispersible granules (WG), water-soluble granules (SG), ULV formulations, micro-capsules and waxes.

These individual formulation types are known in principle and are described, for example, in Winnacker-Küchler, "Chemische Technologie" [Chemical Technology], Volume 7, C. Hauser Verlag Munich, 4th. Edition 1986; Wade van Valkenburg, "Pesticide Formulations", Marcel Dekker, N.Y., 1973; K. Martens, "Spray Drying" Handbook, 3rd Ed. 1979, G. Goodwin Ltd. London.

The necessary formulation auxiliaries, such as inert materials, surfactants, solvents and other additives, are likewise known and are described, for example, in Watkins, "Handbook of Insecticide Dust Diluents and Carriers", 2nd Ed., Darland Books, Caldwell N. J., H.v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Pubi. Corp., Ridgewood N.J.; Sisley and Wood, "Encyclopedia of Surface Active Agents", Chem. Publ. Co. Inc., N.Y. 1964; Schönfeldt, "Grenz-fl ächenaktive Äthylenoxidaddukte" [Surface-active ethylene oxide adducts], Wiss. Verlagsgesell., Stuttgart 1976; Winnacker-Küchler, "Chemische Technologie" [Chemical Technology], Volume 7, C. Hauser Verlag Munich, 4th Edition 1986.

Based on these formulations it is also possible to produce combinations with other pesticidally active substances, for example insecticides, acaricides, herbicides and fungicides, and also with safeners, fertilizers and/or growth regulators, for example in the form of a ready-mix or tank mix.

Wettable powders are preparations which are uniformly dispersible in water and which contain, in addition to the active compound and as well as a diluent or inert substance, surfactants of ionic and/or nonionic type (wetting agents, dispersants), for example polyethoxylated alkyl phenols, polyethoxylated fatty alcohols, polyethoxylated fatty amines, fatty alcohol polyglycol ether sulfates, alkanesulfonates, alkylbenzenesulfonates, sodium ligninsulfonate, sodium 2,2'-dinaphthylmethane-6,6'-disulfonate, sodium dibutylnaphthalenesulfonate or else sodium oleoylmethyltaurinate. To prepare the wettable powders, the herbicidal active compounds are finely ground, for example in customary apparatus such as hammer mills, fan mills and air-jet mills, and are mixed simultaneously or subsequently with the formulation auxiliaries.

Emulsifiable concentrates are prepared by dissolving the active compound in an organic solvent, for example butanol, cyclohexanone, dimethylformamide, xylene or else relatively high-boiling aromatic compounds or hydrocarbons or mixtures of the organic solvents, with the addition of one or more surfactants of ionic and/or nonionic type (emulsifiers). Examples of emulsifiers which can be used are calcium alkylarylsulfonates, such as Ca dodecylbenzenesulfonate, or nonionic emulsifiers, such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters or polyoxyethylene sorbitan esters, for example polyoxyethylene sorbitan fatty acid esters.

Dusts are obtained by grinding the active compound with finely divided solid substances, for example talc, natural clays, such as kaolin, bentonite and pyro- phyllite, or diatomaceous earth.

Suspension concentrates can be water- or oil-based. They can be prepared, for example, by wet milling using commercially customary bead mills, with or without the addition of surfactants as already mentioned above, for example, in the case of the other formulation types.

Emulsions, for example oil-in-water emulsions (EW), can be prepared for example by means of stirrers, colloid mills and/or static mixers using aqueous organic solvents and, if desired, surfactants as already mentioned above, for example, in the case of the other formulation types.

Granules can be prepared either by spraying the active compound onto adsorptive, granulated inert material or by applying active-compound concentrates to the surface of carriers such as sand, kaolinites or granulated inert material, by means of adhesive binders, for example polyvinyl alcohol, sodium polyacrylate or else mineral oils. Suitable active compounds can also be granulated in the manner which is customary for the preparation of fertilizer granules, if desired as a mixture with fertilizers.

Water-dispersible granules are generally prepared by the customary processes, such as spray-drying, fluidized-bed granulation, disk granulation, mixing using high-speed mixers, and extrusion without solid inert material. For the preparation of disk, fluidized-bed, extruder and spray granules, see for example processes in "Spray-Drying Handbook" 3rd ed. 1979, G. Goodwin Ltd., London; J. E. Browning, "Agglomeration", Chemical and Engineering 1967, pages 147 ff.; "Perry's Chemical Engineer's Handbook", 5th Ed., McGraw-Hill, New York 1973, pp. 8–57.

For further details on the formulation of crop protection products, see for example G. C. Klingman, "Weed Control as a Science", John Wiley and Sons Inc., New York, 1961, pages 81-96 and J. D. Freyer, S. A. Evans, "Weed Control Handbook", 5th Ed., Blackwell Scientific Publications, Oxford, 1968, pages 101–103.

The agrochemical formulations generally contain from 0.1 to 99% by weight, in particular from 0.1 to 95% by weight, of active compoundof the formula (I). In wettable powders the concentration of active compound is, for example, from about 10 to 90% by weight, the remainder to 100% by weight consisting of customary formulation constituents. In emulsifiable concentrates the concentration of active compound can be from about 1 to 90%, preferably from 5 to 80%, by weight. Formulations in the form of dusts contain from 1 to 30% by weight of active compound, preferably most commonly from 5 to 20% by weight of active compound, while sprayable solutions contain from about 0.05 to 80%, preferably from 2 to 50%, by weight of active compound. In the case of water-dispersible granules the content of active compound depends partly on whether the active compound is in liquid or solid form and on the granulation auxiliaries, fillers, etc. that are used. In water-dispersible granules the content of active compound, for example, is between 1 and 95% by weight, preferably between 10 and 80% by weight.

In addition, said formulations of active compound may comprise the tackifiers, wetting agents, dispersants, emulsifiers, penetrants, preservatives, antifreeze agents, solvents, fillers, carriers, colorants, antifoams, evaporation inhibitors and pH and viscosity regulators which are customary in each case.

Components which can be used in combination (co-components) for the novel active compounds in mixed formulations or in a tank mix are, for example, known active compounds, as described, for example, in Weed Research 26, 441–445 (1986), or "The Pesticide Manual", 10th edition, The British Crop Protection Council and the Royal Soc. of Chemistry, 1994, England, and literature cited therein. Examples of herbicides which are known from the literature and can be combined with the compounds of the formula (I) are the following active compounds (Note: The compounds are denoted either by their "common name" in accordance with the International Organization for Standardization (ISO) or by their chemical name, together, if appropriate, with a customary code number): acetochlor; acifluorfen; aclonifen; AKH 7088, i.e. [[[1-[5-[2-chloro-4-(trifluoromethyl)phenoxy]-2-nitrophenyl]-2-methoxyethylidene]amino]oxy] acetic acid and its methyl ester; alachlor; alloxydim; ametryn; amidosulfuron; amitrol; AMS, i.e. ammonium sulfamate; anilofos; asulam; atrazin; azimsulfurone (DPX-A8947); aziprotryn; barban; BAS 516H. i.e. 5-fluor-2-phenyl-4H-3,1-benzoxazin-4-one; benazolin; benfluralin; benfuresate; bensulfuron-methyl; bensulide; bentazone; benzofenap; benzofluor; benzoylprop-ethyl; benzthiazuron; bialaphos; bifenox; bromacil; bromobutide; bromofenoxim; bromoxynil; bromuron; buminafos; busoxinone; butachlor; butamifos; butenachlor; buthidazole; butralin; butylate; cafenstrole (CH-900); carbetamide; cafentrazone (ICI-A0051); CDAA, i.e. 2-chloro-N,N-di-2-propenylacetamide; CDEC, i.e. 2-chloroallyl diethyidithiocarbamate; chlomethoxyfen; chloramben; chlorazifop-butyl, chlormesulon (ICI-A0051); chlorbromuron; chlorbufam; chlorfenac; chlorflurecol-methyl; chloridazon; chlorimuron ethyl; chlornitrofen; chlorotoluron; chloroxuron; chlorpropham; chlorsulfuron; chlorthal-dimethyl; chlorthiamid; cinmethylin; cinosulfuron; clethodim; clodinafop and its ester derivatives (e.g. clodinafop-propargyl); clomazone; clomeprop; cloproxydim; clopyralid; cumyluron (JC 940); cyanazine; cycloate; cyclosulfamuron (AC 104); cycloxydim; cycluron; cyhalofop and its ester derivatives (e.g. butyl ester, DEH-112); cyperquat; cyprazine; cyprazole; daimuron; 2,4-DB; dalapon; desmedipham; desmetryn; di-allate; dicamba; dichlobenil; dichlorprop; diclofop and its esters such as diclofop-methyl; diethatyl; difenoxuron; difenzoquat; diflufenican; dimefuron; dimethachlor; dimethametryn; dimethenamid (SAN-582H); dimethazone, clomazon; dimethipin; dimetrasulfuron, dinitramine; dinoseb; dinoterb; diphenamid; dipropetryn; diquat; dithiopyr; diuron; DNOC; eglinazine-ethyl; EL 177, i.e. 5-cyano-1-(1,1-dimethylethyl)-N-methyl-1H-pyrazole-4-carboxamide; endothal; EPTC; esprocarb; ethalfluralin; ethametsulfuron-methyl; ethidimuron; ethiozin; ethofumesate; F5231, i.e. N-[2-chloro-4-fluoro-5-[4-(3-fluoropropyl)-4,5-dihydro-5-oxo-1H-tetrazol- 1-yl]phenyl]ethanesulfonamide; ethoxyfen and its esters (e.g. ethyl ester, HN-252); etobenzanid (HW 52); fenoprop; fenoxan, fenoxaprop and fenoxaprop-P and esters thereof, for example fenoxaprop-P-ethyl and fenoxaprop-ethyl; fenoxydim; fenuron; flamprop-methyl; flazasulfuron; fluazifop and fluazifop-P and esters thereof, for example fluazifop-butyl and fluazifop-P-butyl; fluchloralin; flumetsulam; flumeturon; flumiclorac and its esters (e.g. pentyl ester, S-23031); flumioxazin (S-482); flumipropyn; flupoxam (KNW-739); fluorodifen; fluoroglycofen-ethyl; flupropacil (UBIC-4243); fluridone; flurochloridone; fluroxypyr; flurtamone; fomesafen; fosamine; furyloxyfen; glufosinate; glyphosate; halosafen; halosulfuron and its esters (e.g. methyl ester, NC-319); haloxyfop and its esters; haloxyfop-P (=R-haloxyfop) and its esters; hexazinone; imazamethabenz-methyl; imazapyr; imazaquin and salts such as the ammonium salt; imazethamethapyr; imazethapyr; imazosulfuron; ioxynil; isocarbamid; isopropalin; isoproturon; isouron; isoxaben; isoxapyrifop; karbutilate; lactofen; lenacil; linuron; MCPA; MCPB; mecoprop; mefenacet; mefluidid; metamitron; metazachlor; methabenzthiazuron; metham; methazole; methoxyphenone; methyldymron; metabenzuron, methobenzuron; metobromuron; metolachlor; metosulam (XRD 511); metoxuron; metribuzin; metsulfuron-methyl; MH; molinate; monalide; monocarbamide dihydrogensulfate; monolinuron; monuron; MT 128, i.e. 6-chloro-N-(3-chloro-2-propenyl)-5-methyl-N-phenyl-3-pyridazinamine; MT 5950, i.e. N-[3-chloro-4-(1-methylethyl)-phenyl]-2-methylpentanamide; naproanilide;

napropamide; naptalam; NC 310, i.e. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiargyl (RP-020630); oxadiazon; oxyfluorfen; paraquat; pebulate; pendimethalin; perfluidone; phenisopham; phenmedipham; picloram; piperophos; piributicarb; pirifenop-butyl; pretilachlor; primisulfuron-methyl; procyazine; prodiamine; profluralin; proglinazine-ethyl; prometon; prometryn; propachlor; propanil; propaquizafop and its esters; propazine; propham; propisochlor; propyzamide; prosulfalin; prosulfocarb; prosulfuron (CGA-152005); prynachlor; pyrazolinate; pyrazon; pyrazosulfuron-ethyl; pyrazoxyfen; pyridate; pyrithiobac (KIH-2031); pyroxofop and its esters (e.g. propargyl ester); quinclorac; quinmerac; quinofop and its ester derivatives, quizalofop and quizalofop-P and their ester derivatives, for example quizalofop-ethyl; quizalofop-P-tefuryl and -ethyl; renriduron; rimsulfuron (DPX-E 9636); S 275, i.e. 2-[4-chloro-2-fluoro-5-(2-propynyloxy)phenyl]-4,5,6,7-tetrahydro-2H-indazole; secbumeton; sethoxydim; siduron; simazine; simetryn; SN 106279, i.e. 2-[[7-[2-chloro-4-(trifluoromethyl)phenoxy]-2-naphthalenyl]oxy] propanoic acid and its methyl ester; sulfentrazon (FMC-97285, F-6285); sulfazuron; sulfometuron-methyl; sulfosate (ICI-A0224); TCA; tebutam (GCP-5544); tebuthiuron; terbacil; terbucarb; terbuchlor; terbumeton; terbuthylazine; terbutryn; TFH 450, i.e. N,N-diethyl-3-[(2-ethyl-6-methylphenyl)sulfonyl]-1H-1,2,4-triazole-1-carboxamide; thenylchlor (NSK-850); thiazafluron; thiazopyr (Mon-13200); thidiazimin (SN-24085); thifensulfuron-methyl; thiobencarb; tiocarbazil; tralkoxydim; tri-allate; triasulfuron; triazofenamide; tribenuron-methyl; triclopyr; tridiphane; trietazine; trifluralin; triflusulfuron and esters (e.g. methyl ester, DPX-66037); trimeturon; tsitodef; vernolate; WL 110547, i.e. 5-phenoxy-1-[3-(trifluoromethyl)phenyl]-1H-tetrazole; UBH-509; D-489; LS 82-556; KPP-300; NC-324; NC-330; KH-218; DPX-N8189; SC-0774; DOWCO-535; DK-8910; V-53482; PP-600; MBH-001; KIH-9201; ET-751; KIH-6127 and KIH-2023.

For use, the formulations in customary commercial form are, if desired, diluted in a customary manner, for example using water in the case of wettable powders, emulsifiable concentrates, dispersions and water-dispersible granules. Preparations in the form of dusts, granules for soil application or broadcasting, and also sprayable solutions are not normally diluted further with additional inert substances prior to use.

The required application rate of the compounds of the formula (I) varies with the external conditions, such as temperature, humidity, nature of the herbicide used, etc. It can vary within broad limits, for example between 0.001 and 10.0 kg/ha or more of active substance, but is preferably between 0.005 and 5 kg/ha.

A. CHEMICAL EXAMPLES a) 2-Amino4-isopropyl-6-[2-(3-trifluoromethylphenoxy)-1-ethyl-ethylamino]-1,3,5-triazine (Table 1, Example 68)

2.6 g (0.015 mol) of 2-amino4-chloro-6-isopropyl-1,3,5-triazine, 4.0 g (0.015 mol) of 1-(3-trifluoromethylphenoxy)-2-aminobutane hydrochloride and 6.2 g (0.045 mol) of potassium carbonate were added to 50 ml of dimethylformamide (DMF). The mixture was heated at 80° C. for 3 hours, added into water and extracted with ethyl acetate. The organic phase was washed with water, dried over magnesium sulfate and filtered and the solvent was evaporated under reduced pressure. Purification by silica gel column chromatography using ethyl acetate/petroleum ether (1:1) gave 4.2 g (76%) of the title compound.

b) 2-Amino4-(1-fluoro-1-methylethyl)6-[2-(3-iodophenoxy)-1-methyl-ethylamino]-1,3,5-triazine (Table 1, Example 151)

8.0 g of a ground molecular sieve 3 Å, 1.5 g (0.050 mol) of sodium hydride 80% and 6.0 g (0.045 mol) of methyl 1-fluoro-2-methylpropanoate were added to 9.9 g (0.025 mol) of 2-biguanidino-1-(3-iodophenoxy)-propane hydrochloride in 100 ml of acetonitrile. The mixture was stirred at 25° C. for 2 hours and then at 65° C. for 5 hours. The reaction mixture was filtered, the filtrate was concentrated and the residue was taken up in ethyl acetate. The organic phase was washed with water, dried over magnesium sulfate and filtered and the solvent was evaporated under reduced pressure. Purification by silica gel column chromatography using ethyl acetate/petroleum ether (1:1) gave 3.4 g (32%) of the title compound.

The compounds described in Tables 1 and 2 below are obtained according to or similar to Examples a) and b) above, if appropriate by using customary known methods as described, for example, further above. In the tables:

| | |
|---|---|
| No. = | Example or example number |
| Phys. data = | Characteristic physical data |
| NMR = | $^1$H nuclear magnetic resonance spectrum, for the data, see end of the table in question |
| Me = | Methyl |
| Et = | Ethyl |
| Pr = | Propyl = n-propyl |
| i-Pr = | Isopropyl |
| c-Pr = | Cyclopropyl |
| Bu = | Butyl |
| Pe = | Pentyl |
| Ph = | Phenyl |
| Index numbers = for $(R^7)_n$ | Positions at the phenyl ring, for example: 3,5-Me$_2$ = methyl in positions 3 and 5, position 1 being the "yl" position of the phenyl radical (="phen-1-yl"). |

In the tables, $(R^7)_n$=H indicates the case where n=0 (=no substitution).

TABLE 1

Compounds of the formula (1a)

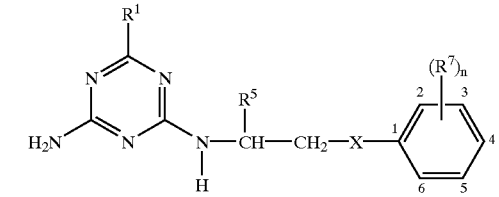

(1a)

| No. | $R^1$ | $R^5$ | X | $(R^7)_n$ | Phys. data |
|---|---|---|---|---|---|
| 1 | i-Pr | Me | O | 3-Ph | NMR |
| 2 | " | " | " | 3-C≡CH | |
| 3 | " | " | " | 3-C≡CMe | |
| 4 | " | " | " | 3-C≡CPh | NMR |
| 5 | " | " | " | 3-OMe | NMR |
| 6 | " | " | " | 3-OEt | NMR |
| 7 | " | " | " | 3-OPh | NMR |
| 8 | " | " | " | 3,5-(OMe)$_2$ | |
| 9 | " | " | " | 3,5-(OEt)$_2$ | |
| 10 | " | " | " | 3-CF$_3$ | |
| 11 | " | " | " | 3-OCF$_3$ | NMR |
| 12 | " | " | " | 3-OC$_2$F$_4$H | NMR |
| 13 | " | " | " | 3-Me, 5-OMe | |
| 14 | " | " | " | 3-Me, 5-OEt | |
| 15 | " | " | " | 3-Me, 5-OPh | |

TABLE 1-continued

Compounds of the formula (1a)

(1a)

| No. | R¹ | R⁵ | X | (R⁷)$_n$ | Phys. data |
|---|---|---|---|---|---|
| 16 | " | " | " | 3-Me, 5-CF$_3$ | |
| 17 | " | " | " | 3-Me, 5-OCF$_3$ | |
| 18 | " | " | " | 3-Me, 5-OC$_2$F$_4$H | |
| 19 | " | " | " | 3-F, 5-OMe | NMR |
| 20 | i-Pr | Me | O | 3-F, 5-OEt | |
| 21 | " | " | " | 3-F, 5-OPh | |
| 22 | " | " | " | 3-F, 5-CF$_3$ | |
| 23 | " | " | " | 3-F, 5-OCF$_3$ | |
| 24 | " | " | " | 3-Cl, 5-OMe | NMR |
| 25 | " | " | " | 3-Br, 5-OMe | |
| 26 | i-Pr | Et | O | H | NMR |
| 27 | " | " | " | 3-Me | NMR |
| 28 | " | " | " | 3,5-Me$_2$ | |
| 29 | " | " | " | 3-Et | |
| 30 | " | " | " | 3,5-Et$_2$ | |
| 31 | " | " | " | 3-i-Pr | |
| 32 | " | " | " | 3,5-i-Pr$_2$ | |
| 33 | " | " | " | 3-c-Pr | |
| 34 | " | " | " | 3,5-c-Pr$_2$ | |
| 35 | " | " | " | 3-Me, 5-Et | |
| 36 | " | " | " | 3-Me, 5-i-Pr | |
| 37 | " | " | " | 3-Me, 5-c-Pr | |
| 38 | " | " | " | 3-Ph | |
| 39 | " | " | " | 3-C≡CH | NMR |
| 40 | " | " | " | 3-C≡CMe | |
| 41 | " | " | " | 3-C≡CPh | |
| 42 | " | " | " | 3-OMe | NMR |
| 43 | " | " | " | 3-OEt | |
| 44 | " | " | " | 3-OPh | NMR |
| 45 | " | " | " | 3,5-OMe$_2$ | NMR |
| 46 | " | " | " | 3-Me, 5-OMe | |
| 47 | " | " | " | 3-Me, 5-OEt | |
| 48 | i-Pr | Et | O | 3-Me, 5-OPh | |
| 49 | " | " | " | 3,5-(OEt)$_2$ | |
| 50 | " | " | " | 3,5-(OPh)$_2$ | |
| 51 | i-Pr | Et | O | 3-F | NMR |
| 52 | " | " | " | 3-Cl | NMR |
| 53 | " | " | " | 3-Br | NMR |
| 54 | " | " | " | 3-I | NMR |
| 55 | " | " | " | 3,5-F$_2$ | NMR |
| 56 | " | " | " | 3,5-Cl$_2$ | NMR |
| 57 | " | " | " | 3,5-Br$_2$ | |
| 58 | " | " | " | 3,5-I$_2$ | |
| 59 | " | " | " | 3-Cl, 5-F | |
| 60 | " | " | " | 3-F, 5-Me | |
| 61 | " | " | " | 3-Cl, 5-Me | |
| 62 | " | " | " | 3-Br, 5-Me | NMR |
| 63 | " | " | " | 3-I, 5-Me | |
| 64 | " | " | " | 3-F, 5-OMe | NMR |
| 65 | " | " | " | 3-Cl, 5-OMe | NMR |
| 66 | " | " | " | 3-Br, 5-OMe | |
| 67 | " | " | " | 3-I, 5-OMe | |
| 68 | " | " | " | 3-CF$_3$ | NMR |
| 69 | " | " | " | 3-OCF$_3$ | NMR |
| 70 | " | " | " | 3-OC$_2$F$_4$H | NMR |
| 71 | " | " | " | 3-F, 5-CF$_3$ | |
| 72 | " | " | " | 3-F, 5-OCF$_3$ | |
| 73 | " | " | " | 3-CF$_3$, 5-Me | |
| 74 | " | " | " | 3-OCF$_3$, 5-Me | |
| 75 | " | " | " | 3-CF$_3$, 5-OCF$_3$ | |
| 76 | i-Pr | i-Pr | O | H | NMR |
| 77 | " | " | " | 3-Me | NMR |
| 78 | " | " | " | 3,5-Me$_2$ | |
| 79 | " | " | " | 3-F | NMR |
| 80 | " | " | " | 3-Cl | NMR |
| 81 | " | " | " | 3-Br | |
| 82 | " | " | " | 3-I | |
| 83 | " | " | " | 3-OMe | NMR |
| 84 | " | " | " | 3,5-F$_2$ | |
| 85 | " | " | " | 3,5-(OMe)$_2$ | |
| 86 | " | " | " | 3-Et | |
| 87 | " | " | " | 3-OEt | |
| 88 | " | " | " | 3-C≡CH | |
| 89 | " | " | " | 3-Me, 5-OMe | |
| 90 | " | " | " | 3-CF$_3$ | |
| 91 | " | " | " | 3-OCF$_3$ | |
| 92 | " | " | " | 3-OC$_2$F$_4$H | |
| 93 | " | " | " | 3-Me, 5-F | |
| 94 | " | " | " | 3-Me, 5-Cl | |
| 95 | " | " | " | 3-Me, 5-Br | |
| 96 | " | " | " | 3-Me, 5-I | |
| 97 | " | " | " | 3-OMe, 5-F | |
| 98 | " | " | " | 3-OMe, 5-Cl | |
| 99 | " | " | " | 3-OMe, 5-Br | |
| 100 | " | " | " | 3-OMe, 5-I | |
| 101 | i-Pr | c-Pr | O | H | NMR |
| 102 | " | " | " | 3-Me | NMR |
| 103 | " | " | " | 3-Et | |
| 104 | i-Pr | c-Pr | O | 3,5-Me$_2$ | |
| 105 | " | " | " | 3-C≡CH | |
| 106 | " | " | " | 3-F | NMR |
| 107 | " | " | " | 3-Cl | NMR |
| 108 | " | " | " | 3-Br | NMR |
| 109 | " | " | " | 3-I | |
| 110 | " | " | " | 3-OMe | NMR |
| 111 | " | " | " | 3,5-F$_2$ | NMR |
| 112 | " | " | " | 3,5-(OMe)$_2$ | |
| 113 | " | " | " | 3-OEt | |
| 114 | " | " | " | 3-CF$_3$ | |
| 115 | " | " | " | 3-OCF$_3$ | |
| 116 | " | " | " | 3-OC$_2$F$_4$H | |
| 117 | " | " | " | 3-Me, 5-OMe | |
| 118 | " | " | " | 3-Me, 5-F | |
| 119 | " | " | " | 3-Me, 5-Cl | |
| 120 | " | " | " | 3-Me, 5-Br | |
| 121 | " | " | " | 3-Me, 5-I | |
| 122 | " | " | " | 3-OMe, 5-I | |
| 123 | " | " | " | 3-OMe, 5-Cl | NMR |
| 124 | " | " | " | 3-OMe, 5-Br | |
| 125 | " | " | " | 3-OMe, 5-I | |
| 126 | CF(CH$_3$)$_2$ | Me | O | 3-Ph | NMR |
| 127 | " | " | " | 3-CH≡CH$_2$ | |
| 128 | " | " | " | 3-CH≡CHCH$_3$ | |
| 129 | " | " | " | 3-CH≡C(CH$_3$)$_2$ | |
| 130 | " | " | " | 3-C≡CH | NMR |
| 131 | " | " | " | 3-C≡CCH$_3$ | |
| 132 | CF(CH$_3$)$_2$ | Me | O | 3-Me, 5-CH≡CH$_2$ | |
| 133 | " | " | " | 3-Me, 5-C≡CH | |
| 134 | " | " | " | 3-C≡C-Ph | NMR |
| 135 | " | " | " | 3-C≡C-Et | |
| 136 | " | " | " | 3-C≡C-Pr | |
| 137 | " | " | " | 3-C≡C-i-Pr | |
| 138 | " | " | " | 3-C≡C-c-Pr | |
| 139 | " | " | " | 3-C$_2$H$_4$Ph | |
| 140 | " | " | " | 3-Pe | |
| 141 | " | " | " | 3-CH$_2$CH$_2$-i-Pr | |
| 142 | " | " | " | 3-CH$_2$CH$_2$-c-Pr | |
| 143 | " | " | " | 3-Me, 5-NH$_2$ | |

TABLE 1-continued

Compounds of the formula (1a)

| No. | R¹ | R⁵ | X | (R⁷)ₙ | Phys. data |
|---|---|---|---|---|---|
| 144 | " | " | " | 3-Me, 5-NO₂ | |
| 145 | " | " | " | 3-Me, 5-OH | |
| 146 | " | " | " | 3-NH₂ | |
| 147 | " | " | " | 3-NO₂ | |
| 148 | " | " | " | 3-NMe₂ | NMR |
| 149 | " | " | " | 3-C≡N | NMR |
| 150 | " | " | " | 3-OH | |
| 151 | CF(CH₃)₂ | Me | O | 3-I | NMR |
| 152 | " | " | " | 3-Br | NMR |
| 153 | " | " | " | 3-Cl | NMR |
| 154 | " | " | " | 3-I, 5-Me | NMR |
| 155 | " | " | " | 3-Br, 5-Me | NMR |
| 156 | " | " | " | 3-Cl, 5-Me | NMR |
| 157 | " | " | " | 3-F, 5-Me | |
| 158 | " | " | " | 2-I, 5-Me | |
| 159 | " | " | " | 2-Br, 5-Me | |
| 160 | CF(CH₃)₂ | Me | O | 2-Cl, 5-Me | |
| 161 | " | " | " | 2-F, 5-Me | |
| 162 | " | " | " | 6-I, 5-Me | |
| 163 | " | " | " | 6-Br, 5-Me | |
| 164 | " | " | " | 6-Cl, 5-Me | |
| 165 | " | " | " | 6-F, 5-Me | |
| 166 | " | " | " | 4-I, 5-Me | |
| 167 | " | " | " | 4-Br, 5-Me | |
| 168 | " | " | " | 4-Cl, 5-Me | |
| 169 | " | " | " | 4-F, 5-Me | |
| 170 | " | " | " | 2-I | |
| 171 | " | " | " | 2-Br | |
| 172 | " | " | " | 2-Cl | NMR |
| 173 | " | " | " | 4-I | |
| 174 | " | " | " | 4-Br | |
| 175 | " | " | " | 4-Cl | NMR |
| 176 | CF(CH₃)₂ | Me | O | 3,5-Cl₂ | NMR |
| 177 | " | " | " | 3,5-Br₂ | |
| 178 | " | " | " | 3,5-I₂ | |
| 178a | " | " | " | 3-Cl, 5-Br | NMR |
| 179 | " | " | " | 3-Cl, 5-F | |
| 180 | " | " | " | 2,3-Cl₂ | NMR |
| 181 | " | " | " | 2,4-Cl₂ | |
| 182 | " | " | " | 2,5-Cl₂ | NMR |
| 183 | " | " | " | 2,6-Cl₂ | |
| 184 | " | " | " | 3,4-Cl₂ | NMR |
| 184a | " | " | " | 3-F,4-Me | |
| 185 | " | " | " | 2,3,5-F₃ | |
| 186 | " | " | " | 3,4,5-F₃ | NMR |
| 187 | " | " | " | 2,3,5,6-F₄ | |
| 187a | " | " | " | 2-Me,3-F | NMR |
| 188 | CF(CH₃)₂ | Me | O | 2,3,4,5,6-F₅ | |
| 188a | " | " | " | 2-Me, 5-F | NMR |
| 189 | " | " | " | 2-Cl, 5-F | NMR |
| 190 | " | " | " | 4-Cl, 5-F | |
| 191 | " | " | " | 6-Cl, 5-F | |
| 192 | " | " | " | 3-Cl, 2-F | |
| 193 | " | " | " | 3-Cl, 4-F | NMR |
| 194 | " | " | " | 3-Cl, 6-F | |
| 195 | CF(CH₃)₂ | Me | O | 3-F, 5-OMe | NMR |
| 196 | " | " | " | 3-F, 5-OEt | |
| 197 | " | " | " | 3-F, 5-OPr | |
| 198 | " | " | " | 3-F, 5-OBu | |
| 199 | " | " | " | 3-F, 5-OPh | |
| 200 | " | " | " | 3-OEt | NMR |
| 201 | " | " | " | 3-OPr | |
| 202 | " | " | " | 3-OBu | NMR |
| 203 | " | " | " | 3-OPh | NMR |
| 204 | " | " | " | 3,5-(OEt)₂ | |
| 205 | " | " | " | 3,5-(OPr)₂ | NMR |
| 206 | " | " | " | 3,5-(OBu)₂ | |
| 207 | " | " | " | 3,5-(OPh)₂ | |
| 208 | " | " | " | 3-Me, 5-OMe | NMR |
| 209 | " | " | " | 3-Me, 5-OEt | NMR |
| 210 | " | " | " | 3-Me, 5-OPr | |
| 211 | " | " | " | 3-Me, 5-OBu | |
| 212 | " | " | " | 3-Me, 5-OPh | |
| 213 | " | " | " | 3-Cl, 5-OMe | NMR |
| 214 | " | " | " | 3-Cl, 5-OEt | |
| 215 | " | " | " | 3-Cl, 5-OPr | |
| 216 | CF(CH₃)₂ | Me | O | 3-Cl, 5-OBu | |
| 217 | " | " | " | 3-Cl, 5-OPh | |
| 218 | " | " | " | 3-Br, 5-OMe | NMR |
| 219 | " | " | " | 3-I, 5-OMe | |
| 220 | CF(CH₃)₂ | Me | O | 3-CF₃, 5-Me | |
| 221 | " | " | " | 3-CF₃, 5-F | |
| 222 | " | " | " | 3-CF₃, 5-Cl | |
| 223 | " | " | " | 3-CF₃, 5-Br | NMR |
| 224 | " | " | " | 3-CF₃, 5-I | |
| 225 | " | " | " | 3-CF₃, 5-OMe | NMR |
| 226 | " | " | " | 3-CF₃, 5-C≡CH | |
| 227 | " | " | " | 3-OCF₃, 5-Me | |
| 228 | " | " | " | 3-OCF₃, 5-F | |
| 229 | " | " | " | 3-OCF₃, 5-Cl | |
| 230 | " | " | " | 3-OCF₃, 5-Br | |
| 231 | " | " | " | 3-OCF₃, 5-I | |
| 232 | " | " | " | 3-OCF₃, 5-OMe | |
| 233 | " | " | " | 3-OCF₃,C≡CH | |
| 234 | " | " | " | 3-OCF₃ | NMR |
| 235 | " | " | " | 3-CF₃, 5-OCF₃ | |
| 236 | " | " | " | 3-OC₂F₄H, 5-Me | |
| 237 | " | " | " | 3-OC₂F₄H, 5-F | |
| 238 | " | " | " | 3-OC₂F₄H, 5-Cl | |
| 239 | " | " | " | 3-OC₂F₄H, 5-Br | |
| 240 | " | " | " | 3-OC₂F₄H, 5-I | |
| 241 | " | " | " | 3-OC₂F₄H, 5-OMe | |
| 242 | " | " | " | 3-OC₂F₄H, 5-C≡CH | |
| 243 | " | " | " | 3-OC₂F₄H | NMR |
| 244 | CF(CH₃)₂ | Me | O | 3-CF₃, 5-OC₂F₄H | |
| 245 | CF(CH₃)₂ | Et | O | 3-Ph | |
| 246 | " | " | " | 3-CH=CH₂ | |
| 247 | " | " | " | 3-CH=CHCH₃ | |
| 248 | " | " | " | 3-CH=C(CH₃)₂ | |
| 249 | " | " | " | 3-C≡CH | NMR |
| 250 | " | " | " | 3-C≡CCH₃ | |
| 251 | " | " | " | 3-Me, 5-CH=CH₂ | |
| 252 | " | " | " | 3-Me, 5-C≡CH | |
| 253 | " | " | " | 3-C≡C-Ph | |
| 254 | " | " | " | 3-C≡C-Et | |
| 255 | " | " | " | 3-C≡C-Pr | |
| 256 | " | " | " | 3-C≡C-i-Pr | |
| 257 | " | " | " | 3-C≡C-c-Pr | |
| 258 | " | " | " | 3-C₂H₄Ph | |
| 259 | " | " | " | 3-Pe | |
| 260 | " | " | " | 3-C₂H₄-i-Pr | |
| 261 | " | " | " | 3-C₂H₄-c-Pr | |
| 262 | " | " | " | 3-Me, 5-NH₂ | |
| 263 | " | " | " | 3-Me, 5-NO₂ | |
| 264 | " | " | " | 3-Me, 5-OH | |
| 265 | " | " | " | 3-NH₂ | |
| 266 | " | " | " | 3-NO₂ | |
| 267 | " | " | " | 3-NMe₂ | |

TABLE 1-continued

Compounds of the formula (1a)

$$R^1 \text{ on triazine with } H_2N, \text{ NH-CH}(R^5)\text{-CH}_2\text{-X-phenyl}(R^7)_n \quad (1a)$$

| No. | $R^1$ | $R^5$ | X | $(R^7)_n$ | Phys. data |
|---|---|---|---|---|---|
| 268 | " | " | " | 3-C≡N | |
| 269 | " | " | " | 3-OH | |
| 270 | CF(CH$_3$)$_2$ | Et | O | 3-I | NMR |
| 271 | " | " | " | 3-Br | NMR |
| 272 | CF(CH$_3$)$_2$ | Et | O | 3-Cl | NMR |
| 273 | " | " | " | 3-I, 5-Me | |
| 274 | " | " | " | 3-Br, 5-Me | NMR |
| 275 | " | " | " | 3-Cl, 5-Me | NMR |
| 276 | " | " | " | 3-F, 5-Me | |
| 277 | " | " | " | 2-I, 5-Me | |
| 278 | " | " | " | 2-Br, 5-Me | |
| 279 | " | " | " | 2-Cl, 5-Me | |
| 280 | " | " | " | 2-F, 5-Me | |
| 281 | " | " | " | 6-I, 5-Me | |
| 282 | " | " | " | 6-Br, 5-Me | |
| 283 | " | " | " | 6-Cl, 5-Me | |
| 284 | " | " | " | 6-F, 5-Me | |
| 285 | " | " | " | 4-I, 5-Me | |
| 286 | " | " | " | 4-Br, 5-Me | |
| 287 | " | " | " | 4-Cl, 5-Me | |
| 288 | " | " | " | 4-F, 5-Me | |
| 289 | " | " | " | 2-I | |
| 290 | " | " | " | 2-Br | |
| 291 | " | " | " | 2-Cl | |
| 292 | " | " | " | 4-I | |
| 293 | " | " | " | 4-Br | |
| 294 | " | " | " | 4-Cl | |
| 295 | CF(CH$_3$)$_2$ | Et | O | 3, 5-Cl$_2$ | NMR |
| 296 | " | " | " | 3,5-Br$_2$ | |
| 297 | " | " | " | 3,5-I$_2$ | |
| 297a | " | " | " | 3-Cl, 5-Br | NMR |
| 298 | " | " | " | 3-Cl, 5-F | |
| 299 | " | " | " | 2,3-Cl$_2$ | NMR |
| 300 | CF(CH$_3$)$_2$ | Et | O | 2,4-Cl$_2$ | |
| 301 | " | " | " | 2, 5-Cl$_2$ | NMR |
| 302 | " | " | " | 2,6-Cl$_2$ | |
| 303 | " | " | " | 3,4-Cl$_2$ | |
| 304 | " | " | " | 2,3,5-F$_3$ | |
| 304a | " | " | " | 3-F,4-Me | |
| 305 | " | " | " | 3,4,5-F$_3$ | |
| 306 | " | " | " | 2,3,5,6-F$_4$ | |
| 306a | " | " | " | 2-Me,3-F | NMR |
| 307 | " | " | " | 2,3,4,5,6,F$_5$ | |
| 307a | " | " | " | 2-Me, 5-F | NMR |
| 308 | " | " | " | 2-Cl, 5-F | |
| 309 | " | " | " | 4-Cl, 5-F | |
| 310 | " | " | " | 6-Cl, 5-F | |
| 311 | " | " | " | 3-Cl, 2-F | |
| 312 | " | " | " | 3-Cl, 4-F | |
| 313 | " | " | " | 3-Cl, 6-F | |
| 314 | CF(CH$_3$)$_2$ | Et | O | 3-F, 5-OMe | NMR |
| 315 | " | " | " | 3-F, 5-OEt | |
| 316 | " | " | " | 3-F, 5-OPr | |
| 317 | " | " | " | 3-F, 5-OBu | |
| 318 | " | " | " | 3-F, 5-OPh | |
| 319 | " | " | " | 3-OEt | |
| 320 | " | " | " | 3-OPr | |
| 321 | " | " | " | 3-OBu | |
| 322 | " | " | " | 3-OPh | NMR |
| 323 | " | " | " | 3,5-(OEt)$_2$ | |
| 324 | " | " | " | 3,5-(OPr)$_2$ | |
| 325 | " | " | " | 3,5-(OBu)$_2$ | |
| 326 | " | " | " | 3,5-(OPh)$_2$ | |
| 327 | " | " | " | 3-Me, 5-OMe | |
| 328 | CF(CH$_3$)$_2$ | Et | O | 3-Me, 5-OEt | |
| 329 | " | " | " | 3-Me, 5-OPr | |
| 330 | " | " | " | 3-Me, 5-OBu | |
| 331 | " | " | " | 3-Me, 5-OPh | |
| 332 | " | " | " | 3-Cl, 5-OMe | NMR |
| 333 | " | " | " | 3-Cl, 5-OEt | |
| 334 | " | " | " | 3-Cl, 5-O-Pr | |
| 335 | " | " | " | 3-Cl, 5-O-Bu | |
| 336 | " | " | " | 3-Cl, 5-OPh | |
| 337 | " | " | " | 3-Br, 5-OMe | |
| 338 | " | " | " | 3-I, 5-OMe | |
| 339 | CF(CH$_3$)$_2$ | Et | O | 3-CF$_3$, 5-Me | |
| 340 | " | " | " | 3-CF$_3$, 5-F | |
| 341 | " | " | " | 3-CF$_3$, 5-Cl | |
| 342 | " | " | " | 3-CF$_3$, 5-Br | NMR |
| 343 | " | " | " | 3-CF$_3$, 5-I | |
| 344 | " | " | " | 3-CF$_3$, 5-OMe | NMR |
| 345 | " | " | " | 3-CF$_3$, 5-C≡CH | |
| 346 | " | " | " | 3-OCF$_3$, 5-Me | |
| 347 | " | " | " | 3-OCF$_3$, 5-F | |
| 348 | " | " | " | 3-OCF$_3$, 5-Cl | |
| 349 | " | " | " | 3-OCF$_3$, 5-Br | |
| 350 | " | " | " | 3-OCF$_3$, 5-I | |
| 351 | " | " | " | 3-OCF$_3$, 5-OMe | |
| 352 | " | " | " | 3-OCF$_3$, 5-C≡CH | |
| 353 | " | " | " | 3-OCF$_3$ | NMR |
| 354 | " | " | " | 3-CF$_3$, 5-OCF$_3$ | |
| 355 | " | " | " | 3-OC$_2$F$_4$, 5-Me | |
| 356 | CF(CH$_3$)$_2$ | Et | O | 3-OC$_2$F$_4$H, 5-F | |
| 357 | " | " | " | 3-OC$_2$F$_4$H, 5-Cl | |
| 358 | " | " | " | 3-OC$_2$F$_4$H, 5-Br | |
| 359 | " | " | " | 3-OC$_2$F$_4$H, 5-I | |
| 360 | " | " | " | 3-OC$_2$F$_4$H, 5-OMe | |
| 361 | " | " | " | 3-OC$_2$F$_4$H, 5-C≡CH | |
| 362 | " | " | " | 3-OC$_2$F$_4$H | NMR |
| 363 | " | " | " | 3-CF$_3$, 5-OC$_2$F$_4$H | |
| 364 | CF(CH$_3$)$_2$ | Et | O | H | NMR |
| 365 | " | " | " | 3-Me | NMR |
| 366 | " | " | " | 3,5-Me$_2$ | NMR |
| 367 | " | " | " | 3-Me, 5-Et | |
| 368 | " | " | " | 3-Me, 5-i-Pr | |
| 369 | " | " | " | 3-F | NMR |
| 370 | " | " | " | 3,5-F$_2$ | NMR |
| 371 | " | " | " | 3-CF$_3$ | NMR |
| 372 | " | " | " | 3-OMe | NMR |
| 373 | " | " | " | 3,5-(OMe)$_2$ | NMR |
| 374 | " | " | " | 3-Et | |
| 375 | " | " | " | 3,5-Et$_2$ | |
| 376 | " | " | " | 3-i-Pr | |
| 377 | " | " | " | 3,5-(i-Pr)$_2$ | |
| 378 | " | " | " | 3-c-Pr | |
| 379 | " | " | " | 3,5-(c-Pr)$_2$ | |
| 380 | CF(CH$_3$)$_2$ | i-Pr | O | H | NMR |
| 381 | " | " | " | 3-Me | NMR |
| 382 | " | " | " | 3,5-Me$_2$ | NMR |
| 383 | " | " | " | 3-F | NMR |
| 384 | CF(CH$_3$)$_2$ | i-Pr | O | 3-Cl | NMR |
| 385 | " | " | " | 3-Br | |
| 386 | " | " | " | 3-I | |
| 387 | " | " | " | 3-OMe | NMR |
| 388 | " | " | " | 3,5-F$_2$ | |
| 389 | " | " | " | 3,5-(OMe)$_2$ | |
| 390 | " | " | " | 3-Et | |
| 391 | " | " | " | 3-OEt | |

TABLE 1-continued

Compounds of the formula (1a)

(1a)

R¹ group attached to triazine ring with H₂N and NH-CH(R⁵)-CH₂-X-phenyl(R⁷)ₙ substituents

| No. | R¹ | R⁵ | X | (R⁷)ₙ | Phys. data |
|---|---|---|---|---|---|
| 392 | " | " | " | 3-C≡CH | |
| 393 | " | " | " | 3-Me, 5-OMe | |
| 394 | " | " | " | 3-CF₃ | |
| 395 | " | " | " | 3-OCF₃ | |
| 396 | " | " | " | 3-OC₂F₄H | |
| 397 | " | " | " | 3-Me, 5-F | |
| 398 | " | " | " | 3-Me, 5-Cl | |
| 399 | " | " | " | 3-Me, 5-Br | |
| 400 | " | " | " | 3-Me, 5-I | |
| 401 | " | " | " | 3-OMe, 5-F | |
| 402 | " | " | " | 3-OMe, 5-Cl | |
| 403 | " | " | " | 3-OMe, 5-Br | |
| 404 | " | " | " | 3-OMe, 5-I | |
| 405 | CF(CH₃)₂ | c-Pr | O | H | NMR |
| 406 | " | " | " | 3-Me | NMR |
| 407 | " | " | " | 3-Et | |
| 408 | " | " | " | 3,5-Me₂ | |
| 409 | " | " | " | 3-C≡CH | |
| 410 | " | " | " | 3-F | NMR |
| 411 | " | " | " | 3-Cl | NMR |
| 412 | CF(CH₃)₂ | c-Pr | O | 3-Br | |
| 413 | " | " | " | 3-I | |
| 414 | " | " | " | 3-OMe | NMR |
| 415 | " | " | " | 3,5-F₂ | NMR |
| 416 | " | " | " | 3,5-(OMe)₂ | |
| 417 | " | " | " | 3-OEt | |
| 418 | " | " | " | 3-CF₃ | |
| 419 | " | " | " | 3-OCF₃ | |
| 420 | " | " | " | 3-OC₂F₄H | |
| 421 | " | " | " | 3-Me, 5-OMe | |
| 422 | " | " | " | 3-Me, 5-F | |
| 423 | " | " | " | 3-Me, 5-Cl | |
| 424 | " | " | " | 3-Me, 5-Br | |
| 425 | " | " | " | 3-Me, 5-I | |
| 426 | " | " | 1 | 3-OMe, 5-I | |
| 427 | " | " | " | 3-OMe, 5-Cl | NMR |
| 428 | " | " | " | 3-OMe, 5-Br | |
| 429 | " | " | " | 3-OMe, 5-I | |
| 430 | CCl(CH₃)₂ | Et | O | 3-F | |
| 431 | " | " | " | 3-Cl | |
| 432 | " | " | " | 3-Br | |
| 433 | " | " | " | 3-I | |
| 434 | " | " | " | 3,5-F₂ | |
| 435 | " | " | " | H | |
| 436 | " | " | " | 3-Me | |
| 437 | " | " | " | 3,5-Me₂ | |
| 438 | " | " | " | 3-C≡CH | |
| 439 | " | " | " | 3-OMe | |
| 440 | CCl(CH₃)₂ | Et | O | 3,5-(OMe)₂ | |
| 441 | " | " | " | 3-Me, 5-OMe | |
| 442 | " | " | " | 3-CF₃ | |
| 443 | " | " | " | 3-OCF₃ | |
| 444 | " | " | " | 3-OC₂F₄H | |
| 445 | " | " | " | 3-Me, 5-F | |
| 446 | " | " | " | 3-Me, 5-Cl | |
| 447 | " | " | " | 3-Me, 5-Br | |
| 448 | " | " | " | 3-Me, 5-I | |
| 449 | " | " | " | 3-OMe, 5-F | |
| 450 | " | " | " | 3-OMe, 5-Cl | |
| 451 | " | " | " | 3-OMe, 5-Br | |
| 452 | " | " | " | 3-OMe, 5-I | |
| 453 | " | " | " | 3-Et | |
| 454 | " | " | " | 3-OEt | |
| 455 | CCl(CH₃)₂ | Me | O | 3-Cl | NMR |
| 456 | " | " | " | 3-Br | |
| 457 | " | " | " | 3-I | |
| 458 | " | " | " | 3-OEt | |
| 459 | " | " | " | 3-OCF₃ | |
| 460 | " | " | " | 3-OC₂F₄H | |
| 461 | " | " | " | 3-C≡CH | |
| 462 | " | " | " | 3-Me, 5-F | |
| 463 | " | " | " | 3-Me, 5-Cl | NMR |
| 464 | " | " | " | 3-Me, 5-Br | |
| 465 | " | " | " | 3-Me, 5-I | NMR |
| 466 | " | " | " | 3-OMe, 5-F | |
| 467 | " | " | " | 3-OMe, 5-Cl | |
| 468 | CCl(CH₃)₂ | Me | O | 3-OMe, 5-Br | |
| 469 | " | " | " | 3-OMe, 5-I | |
| 470 | " | " | " | 3-Me, 5-OMe | |
| 471 | " | " | " | 3-Me, 5-OEt | |
| 472 | CCl(CH₃)₂ | i-Pr | O | H | |
| 473 | " | " | " | 3-Me | |
| 474 | " | " | " | 3,5-Me₂ | |
| 475 | " | " | " | 3-F | |
| 476 | " | " | " | 3,5-F₂ | |
| 477 | " | c-Pr | " | H | |
| 478 | " | " | " | 3-Me | |
| 479 | " | " | " | 3,5-Me₂ | |
| 480 | " | " | " | 3-F | |
| 481 | " | " | " | 3,5-F₂ | |
| 482 | i-Pr | Me | O | 3-OPr | |
| 483 | " | " | " | 3-OBu | NMR |
| 484 | " | " | " | 3-O-i-Pr | |
| 485 | " | " | " | 3-O-c-Pr | |
| 486 | " | " | " | 3,5-(OPr)₂ | NMR |
| 487 | " | " | " | 3-CN | NMR |
| 488 | " | " | " | 3-Me, 5-O-i-Pr | NMR |
| 489 | " | " | " | 3-Me, 5-O-c-Pr | |
| 490 | " | Et | " | 2,3-Cl₂ | NMR |
| 491 | CF(CH₃)₂ | Me | O | 3-Cl, 2-Me | |
| 492 | " | " | " | 3-Cl, 4-Me | NMR |
| 493 | " | " | " | 3-Cl, 6-Me | NMR |
| 494 | " | " | " | 3-O-i-Pr | |
| 495 | " | " | " | 3-O-c-Pr | |
| 496 | CF(CH₃)₂ | Me | O | 3-Me, 5-O-i-Pr | NMR |
| 497 | " | " | " | 3-F, 5-O-i-Pr | |
| 498 | " | " | " | 3-Cl, 5-O-i-Pr | |
| 499 | " | Et | " | 3-Cl, 2-Me | |
| 500 | " | " | " | 3-Cl, 4-Me | NMR |
| 501 | " | " | " | 3-Cl, 6-Me | |
| 502 | " | Me | NH | H | |
| 503 | " | " | " | 3-Me | |
| 504 | " | " | " | 3,5-Me₂ | |
| 505 | " | " | N-Me | H | |
| 506 | " | " | " | 3-Me | |
| 507 | " | " | " | 3,5-Me₂ | |
| 508 | " | " | S | H | |
| 509 | " | " | " | 3-Me | |
| 510 | " | " | " | 3,5-Me₂ | |

¹H NMR data (CDCl₃, 300 MHz, δ reference to TMS as standard) of the compounds of the formula (1a) of Table 1:

Example No. NMR Data 1 1.2 (d, 6H), 1.4 (d, 3H), 2.7 (m, 1H), 4.0 (m, 1H), 4.1 (m, 1H), 4.5 (m, 1H), 5.2 (m, 3H), 6.9–7.6 (m, 9H).

4 1.2 (d, 6H), 1.4 (d, 3H), 2.7 (m, 1H), 3.9 (m, 1H), 4.1 (m, 1H), 4.4 (m, 1H), 5.2 (m, 3H), 6.9–7.6 (m, 9H).

5 1.2 (d, 6H), 1.4 (d, 3H), 3.8 (s, 3H), 3.9 (m, 1H), 4.1 (m, 1H), 4.4 (m, 1H), 5.2 (m, 3H), 6.5 (m, 3H), 7.2 (m, 1H).

6 1.2 (d, 6H), 1.3 (d, 3H), 1.4 (t, 3H), 2.7 (m, 1H), 3.9 (m, 1H), 4.0 (m, 3H), 4.4 (m, 1H), 5.2 (m, 3H), 6.5 (m, 2H), 6.8 (m, 1H), 7.2 (m, 1H).

7 1.2 (d, 6H), 1.3 (d, 3H), 2.7 (m, 1H), 3.9 (m, 1H), 4.1 (m, 1H), 4.4 (m, 1H), 5.2 (m, 3H), 6.6 (m, 2H), 7.2 (m, 7H).

11 1.2 (d, 6H), 1.4 (d, 3H), 2.7 (m, 1H), 3.9 (m, 1H), 4.1 (m, 1H), 4.4 (m, 1H), 5.2 (m, 3H), 6.8 (m, 3H), 7.3 (m, 1H).

12 1.2 (d, 6H), 1.4 (d, 3H), 2.7 (m, 1H), 3.9 (m, 1H), 4.1 (m, 1H), 4.4 (m, 1H), 5.2 (m, 3H), 5.9 (tt, 1H), 6.8 (m, 3H), 7.3 (m, 1H).

19 1.2 (d, 6H), 1.4 (d, 3H), 2.7 (m, 1H), 3.8 (s, 3H), 3.9 (m, 1H), 4.1 (m, 1H), 4.4 (m, 1H), 5.2 (m, 3H), 6.2–6.5 (m, 3H).

24 1.2 (d, 6H), 1.4 (d, 3H), 2.7 (m, 1H), 3.8(5, 3H), 3.9 (m, 1H), 4.1 (m, 1H), 4.4 (m, 1H), 5.2 (m, 3H), 6.6 (m, 3H).

26 1.0 (t, 3H), 1.2 (d, 6H), 1.7 (m, 1H), 1.9 (m, 1H), 2.7 (m, 1H), 3.9–4.4 (m, 3H), 5.2 (m, 3H), 6.8–7.0 (m, 3H), 7.3 (m, 2H).

27 1.0 (t, 3H), 1.2 (d, 6H), 1.7 (m, 1H), 1.8 (m, 1H), 2.3 (s, 3H), 2.7 (m, 1H), 3.9 (m, 1H), 4.1 (m, 1H), 4.3 (m, 1H), 5.2 (brd., 3H), 6.7 (m, 3H), 7.2 (m, 1H).

39 1.0 (t, 3H), 1.2 (d, 6H), 1.7 (m, 1H), 1.9 (m, 1H), 2.7 (m, 1H), 3.0 (s, 1H), 3.9 (m, 1H), 4.1 (m, 1H), 4.3 (m, 1H), 5.2 (m, 3H), 6.9 (m, 1H), 7.1 (m, 1H), 7.2 (m, 2H).

42 1.0 (t, 3H), 1.2 (d, 6H), 1.7 (m, 1H), 1.9 (m, 1H), 2.7 (m, 1H), 3.8 (s, 3H), 3.9–4.4 (m, 3H), 5.2 (m, 3H), 6.4–6.8 (m, 3H), 7.2 (m, 1H).

44 1.0 (t, 3H), 1.2 (d, 6H), 1.7 (m, 1H), 1.8 (m, 1H), 2.7 (m, 1H), 3.9 (m, 1H), 4.1 (m, 1H), 4.3 (m, 1H), 5.2 (brd., 3H), 6.5–7.4 (m, 9H).

45 1.0 (t, 3H), 1.2 (d, 6H), 1.7 (m, 1H), 1.9 (m, 1H), 2.7 (m, 1H), 3.7 (s, 6H), 3.8–4.4 (m, 3H), 5.5 (m, 3H), 6.1–6.3 (m, 3H).

51 1.0 (t, 3H), 1.2 (d, 6H), 1.7 (m, 1H), 1.9 (m, 1H), 2.7 (m, 1H), 3.8–4.4 (m, 3H), 5.2 (m, 3H), 6.6–6.8 (m, 3H), 7.2 (m, 1H).

52 1.0 (t, 3H), 1.2 (d, 6H), 1.7 (m, 1H), 1.9 (m, 1H), 2.7 (m, 1H), 3.8–4.4 (m, 3H), 5.5 (m, 3H), 6.7–7.2 (m, 4H).

53 1.0 (t, 3H), 1.2 (d, 6H), 1.7 (m, $_1$H), 1.9 (m, 1H), 2.7 (m, 1H), 3.8–4.4 (m, 3H), 5.6 (m, 3H), 6.8 (m, 1H), 7.0–7.2 (m, 3H).

54 1.0 (t, 3H), 1.2 (d, 6H), 1.6 (m, 1H), 1.8 (m, 1H), 2.7 (m, 1H), 3.9 (m, 1H), 4.1 (m, 1H), 4.3 (m, 1H), 5.3 (m, 3H), 6.9 (m, 2H), 7.3 (m, 2H).

55 1.0 (t, 3H), 1.2 (d, 6H), 1.7 (m, 1H), 1.9 (m, 1H), 2.7 (m, 1H), 3.8–4.4 (m, 3H), 5.2 (m, 3H), 6.4–6.6 (m, 3H).

56 1.0 (t, 3H), 1.2 (d, 6H), 1.7 (m, 1H), 1.9 (m, 1H), 2.7 (m, 1H), 3.8–4.4 (m, 3H), 5.5 (m, 3H), 6.8–7.1 (m, 3H).

62 1.0 (t, 3H), 1.2 (d, 6H), 1.6 (m, 1H), 1.8 (m, 1H), 2.3 (s, 3H), 2.7 (m, 1H), 3.9 (m, 1H), 4.1 (m, 1H), 4.3 (m, 1H), 5.2 (m, 3H), 6.6 (m, 1H), 6.9 (m, 2H).

64 1.0 (t, 3H), 1.2 (d, 6H), 1.6 (m, 1H), 1.8 (m, 1H), 2.7 (m, 1H), 3.8 (s, 3H), 3.9 (m, 1H), 4.1 (m, 1H), 4.3 (m, 1H), 5.2 (m, 3H), 6.2–6.5(m, 3H).

65 1.9 (t, 3H), 1.2 (d, 6H), 1.6 (m, 1H), 1.8 (m, 1H), 2.7 (m, 1H), 3.8 (s, 3H), 3.9 (m, 1H), 4.1 (m, 1H), 4.2 (m, 1H), 5.4 (m, 3H), 6.6 (m, 3H).

68 1.0 (t, 3H), 1.2 (d, 6H), 1.7 (m, 1H), 1.8 (m, 1H), 2.7 (m, 1H), 4.0 (m, 1H), 4.1 (m, 1H), 4.3 (m, 1H), 5.2 (m, 3H), 7.1 (m, 3H), 7.4(m, 1H).

69 1.0 (t, 3H), 1.2 (d, 6H), 1.7 (m, 1H), 1.8 (m, 1H), 2.7 (m, 1H), 4.0 (m, 1H), 4.1 (m, 1H), 4.3 (m, 1H), 5.1 (m, 3H), 6.8 (m, 3H), 7.3(m, 1H).

70 1.0 (t, 3H), 1.2 (d, 6H), 1.7 (m, 1H), 1.8 (m, 1H), 2.7 (m, 1H), 4.0 (m, 1H), 4.1 (m, 1H), 4.3 (m, 1H), 5.1 (m, 3H), 5.9 (tt, 1H), 6.8(m, 3H), 7.3 (m, 1H).

76 1.0 (d, 6H), 1.2 (d, 6H), 2.1 (m, 1H), 2.5 (m, 1H), 3.9–4.4 (m, 3H), 5.2 (m, 3H), 6.8–7.0 (m, 3H), 7.2 (m, 2H).

77 1.0 (d, 6H), 1.2 (d, 6H), 2.1 (m, 1H), 2.3 (s, 3H), 2.5 (m, 1H), 3.9–4.4 (m, 3H), 5.3 (m, 3H), 6.6–6.8 (m, 3H), 7.2 (m, 1H).

79 1.0 (d, 6H), 1.2 (d, 6H), 2.1 (m, 1H), 2.7 (m, 1H), 3.9–4.4 (m, 3H), 5.3 (m, 3H), 6.6 –6.8 (m, 3H), 7.2 (m, 1H).

80 1.0 (d, 6H), 1.2 (d, 6H), 2.1 (m, 1H) 2.7 (m, 1H), 3.9–4.4 (m, 3H), 5.2 (m, 3H), 6.8–7.2 (m, 4H).

83 1.0 (d, 6H), 1.2 (d, 6H), 2.1 (m, 1H), 2.6 (m, 1H), 3.7 (s, 3H), 3.8–4.3 (m, 3H), 5.4 (m, 3H), 6.3–6.6 (m, 3H), 7.1 (m, 1H).

101 0.3–0.6 (m, 4H), 1.2 (m, 1H), 1.2 (d, 6H), 2.5 (m, 1H), 3.7 (m, 1H), 4.0–4.2 (m, 2H), 5.4 (m, 3H), 6.8–7.0 (m, 3H), 7.3 (m, 1H).

102 0.3–0.6 (m, 4H), 1.2 (m, 1H), 1.2 (d, 6H), 2.3 (s, 3H), 2.7 (m, 1H), 3.7 (m, 1H), 4.0–4.2 (m, 2H), 5.4 (m, 3H), 6.6–6.8 (m, 3H), 7.1(m, 1H).

106 0.3–0.6 (m, 4H), 1.2 (m, 1H), 1.2 (d, 6H), 2.7 (m, 1H), 3.7 (m, 1H), 4.0–4.2 (m, 2H), 5.3 (m, 3H), 6.6–6.8 (m, 3H), 7.2 (m, 1H).

107 0.3–0.6 (m, 4H), 1.2 (m, 1H), 1.2 (d, 6H), 2.7 (m, 1H), 3.7 (m, 1H), 4.0–4.2 (m, 2H), 5.2 (m, 3H), 6.8–7.2 (m, 4H).

108 0.3–0.6 (m, 4H), 1.1–1.3 (m, 7H), 2.7 (m, 1H), 3.9 (m, 1H), 4.0–4.2 (m, 2H), 5.3 (m, 3H), 6.8 (m, 1H), 7.0–7.2 (m, 3H).

110 0.3–0.6 (m, 4H), 1.2 (m, 1H), 1.2 (d, 6H), 2.7 (m, 1H), 3.7 (m, 1H), 3.8 (s, 3H), 4.0–4.2 (m, 2H), 5.6 (m, 3H), 6.4–6.8 (m, 3H), 7.2(m, 1H).

111 0.3–0.6 (m, 4H), 1.2 (m, 1H), 1.2 (d, 6H), 1.7 (m, 1H), 2.7 (m, 1H), 3.7 (m, 1H), 4.0–4.2 (m, 2H), 5.2 (m, 3H), 6.3–6.6 (m, 3H).

123 0.3–0.6 (m, 4H), 1.2 (m, 1H), 1.2 (d, 6H), 2.7 (m, 1H), 3.7 (m, 1H), 3.8 (s, 3H), 4.0–4.2 (m, 2H), 5.2 (m, 3H), 6.4–6.7 (m, 3H).

126 1.4 (d, 3H), 1.7 (d, 6H), 4.0 (m, 1H), 4.1 (m, 1H), 4.5 (m, 1H), 5.5 (m, 3H), 6.9–7.6 (m, 9H).

130 1.4 (d, 3H), 1.7 (d, 6H), 3.1 (s, 1H), 3.9 (m, 1H), 4.1 (m, 9H), 4.4 (m, 1H), 5.4 (m, 3H), 6.9 (m, 1H), 7.1 (m, 1H), 7.2 (m, 1H).

134 1.4 (d, 3H), 1.7 (d, 6H), 3.9 (m, 1H), 4.1 (m, 1H), 4.5 (m, 1H), 5.5 (m, 3H), 6.9 bis 7.6 (m, 9H).

148 1.4 (d, 3H) 1.7 (d, 6H), 2.9 (s, 6H), 4.0 (m, 2H), 4.4 (m, 1H), 5.5 (m, 3H), 6.3 (m, 3H), 7.1 (m, 1H).

149 1.4 (d, 3H), 1.7 (d, 6H), 3.9 (m, 1H), 4.1 (m, 2H), 4.5 (m, 1H), 5.7 (m, 3H), 7.3 (m, 4H).

151 1.4 (d, 3H), 1.7 (d, 6H), 3.9 (m, 1H), 4.1 (m, 1H), 4.4 (m, 1H), 5.5 (m, 3H), 6.9 (m, 2H), 7.3 (m, 2H).

152 1.4 (d, 3H), 1.7 (d, 6H), 3.9 (m, 1H), 4.1 (m, 1H), 4.4 (m, 1H), 5.5 (m, 3H), 6.8 (m, 1H), 7.1 (m, 3H).

153 1.4 (d, 3H), 1.7 (d, 6H), 3.9 (m, 1H), 4.1 (m, 1H), 4.4 (m, 1H), 5.5 (m, 3H), 6.8 (m, 1H), 6.9 (m, 1H), 7.1 (m, 2H).

154 1.4 (d, 3H), 1.7 (d, 6H), 2.3 (s, 3H), 3.9 (m, 1H), 4.0 (m, 1H), 4.4 (m, 1H), 5.4 (m, 3H), 6.7 (m, 1H), 7.2 (m, 2H).

155 1.4 (d, 3H), 1.7 (d, 6H), 2.3 (s, 3H), 3.9 (m, 1H), 4.0 (m, 1H), 4.4(m, 1H), 5.5 (m, 3H), 6.7 (m, 1H), 7.0 (m, 2H).

156 1.4 (d, 3H), 1.7 (d, 6H), 2.3 (s, 3H), 3.9 (m, 1H), 4.0 (m, 1H), 4.4(m, 1H), 5.3 (m, 3H), 6.6–6.9 (m, 3H).

172 1.4 (d, 3H), 1.7 (d, 6H), 4.0 (m, 1H), 4.1 (m, 1H), 4.5 (m, 1H), 5.2 (m, 3H), 6.9 (m, 2H), 7.2 (m, 1H), 7.4 (m, 1H).

175 1.4 (d, 3H), 1.7 (d, 6H), 3.9 (m, 1H), 4.0 (m, 1H), 4.4 (m, 1H), 5.4 (m, 3H), 6.8 (m, 2H), 7.2 (m, 2H).

176 1.4 (d, 3H), 1.7 (d, 6H), 3.9 (m, 1H), 4.1 (m, 1H), 4.4 (m, 1H), 5.5 (m, 3H), 7.0 (s, 3H).

178a 1.4 (d, 3H), 1.7 (d, 6H), 3.9 (m, 1H), 4.1 (m, 1H), 4.4 (m, 1H), 5.4 (m, 3H), 7.0 (m, 1H), 7.1 (m, 2H)

180 1.4 (d, 3H), 1.7 (d, 6H), 4.0 (m, 1H), 4.1 (m, 1H), 4.5 (m, 1H), 5.4 (m, 3H), 6.9 (m, 1H), 7.1 (m, 2H).

182 1.4 (d, 3H), 1.7 (d, 6H), 4.0 (m, 1H), 4.2 (m, 1H), 4.5 (m, 1H), 5.5 (m, 3H), 6.9 (m, 1H), 7.2 (m, 2H).

184 1.3 (d, 3H), 1.7 (d, 6H), 3.9 (m, 1H), 4.0 (m, 1H), 4.4 (m, 1H), 5.4 (brd., 3H), 6.8 (m, 1H), 7.0 (m, 2H).

186 1.4 (d, 3H), 1.7 (d, 6H), 3.9 (m, 1H), 4.0 (m, 1H), 4.4 (m, 1H), 5.4 (m, 3H), 6.6 (m, 2H).

187a 1.4 (d, 3H), 1.7 (d, 6H), 2.1 (s, 3H), 4.0 (m, 2H), 4.5 (m, 1H), 5.4 (m, 3H), 6.6 (m, 2H), 7.1 (m, 1H).

188a 1.4 (d, 3H), 1.7 (d, 6H), 2.2 (s, 3H), 3.9 (m, 1H), 4.0 (m, 1H), 4.5 (m, 1H), 5.4 (m, 3H), 6.5 –7.1 (m, 3H).

189 1.4 (d, 3H), 1.7 (d, 6H), 4.0 (m, 1H), 4.1 (m, 1H), 4.5 (m, 1H), 5.4 (m, 3H), 6.6 (m, 1H), 7.3 (m, 2H).

193 1.3 (d, 3H), 1.7 (d, 6H), 3.9 (m, 1H), 4.0 (m, 1H), 4.4 (m, 1H), 5.4 (m, 3H), 6.8 (m, 1H), 7.0 (m, 2H).

195 1.4 (d, 3H), 1.7 (d, 6H), 3.8 (s, 3H), 3.9 (m, 1H), 4.1 (m, 1H), 4.4 (m, 1H), 5.4 (m, 3H), 6.2–6.5 (m, 3H).

200 1.4 (m, 6H), 1.7 (d, 6H), 3.9 (m, 1H), 4.0 (m, 3H), 4.4 (m, 1H), 5.5 (m, 3H), 6.5 (m, 2H), 6.8 (m, 1H), 7.2 (m, 1H).

202 1.0 (t, 3H), 1.4 (d, 3H), 1.5 (m, 2H), 1.7 (d, 6H), 1.8 (m, 2H), 3.9 (m, 3H), 4.1 (m, 1H), 4.4 (m, 1H), 5.5 (m, 3H), 6.5 (m, 2H), 6.8 (m, 1H), 7.2 (m, 1H).

203 1.4 (d, 3H, 1.7 (d, 6H), 3.9 (m, 1H), 4.1 (m, 1H), 4.4 (m, 1H), 5.4 (m, 3H), 6.6–7.4 (m, 9H).

205 1.0 (t, 6H), 1.3 (d, 3H), 1.7 (d, 6H), 1.8 (tq, 4H), 3.8 (m, 1H), 3.9 (t, 4H), 4.1 (m, 1H), 4.4 (m, 1H), 5.4 (m, 3H), 6.1 (s, 1H), 6.3 (s, 2H).

208 1.4 (d, 3H), 1.7 (d, 6H), 2.3 (s, 3H), 3.8 (s, 3H), 3.9 (m, 1H), 4.1 (m, 1H), 4.4 (m, 1H), 5.4 (brd., 3H), 6.3 (m, 2H), 6.6 (m, 1H).

209 1.3 (t, 3H), 1.4 (d, 3H), 1.7 (d, 6H), 2.3 (s, 3H), 3.9 (m, 1H), 4.0 (q, 2H), 4.1 (m, 1H), 4.4 (m, 1H), 5.4 (d, 1H), 5.6 (brd., 2H), 6.3 (s, 2H), 6.4 (s, 1H).

213 1.4 (d, 3H), 1.7 (d, 6H), 3.8 (s, 3H), 3.9 (m, 1H), 4.1 (m, 1H), 4.4 (m, 1H), 5.5 (m, 3H), 6.6 (m, 3H).

218 1.4 (d, 3H), 1.7 (d, 6H), 3.8 (s, 3H), 3.9 (m, 1H), 4.1 (m, 1H), 4.4 (m, 1H), 5.4 (m, 3H), 6.6–6.8 (m, 3H).

223 1.4 (d, 3H), 1.6 (d, 6H), 3.9 (m, 1H), 4.1 (m, 1H), 4.4 (m, 1H), 5.4 (m, 3H), 7.1 (m, 1H), 7.4 (m, 2H).

225 1.4 (d, 3H), 1.7 (d, 6H), 3.8 (s, 3H), 3.9 (m, 1H), 4.1 (m, 1H), 4.4 (m, 1H), 5.5 (m, 3H), 6.8 (m, 3H).

234 1.4 (d, 3H), 1.7 (d, 6H), 3.9 (m, 1H), 4.1 (m, 1H), 4.4 (m, 1H), 5.5 (m, 3H), 6.8 (m, 3H), 7.3 (m, 1H).

243 1.4 (d, 3H), 1.7 (d, 6H), 3.9 (m, 1H), 4.1 (m, 1H), 4.5 (m, 1H), 5.4 (m, 3H), 5.9 (tt, 1H), 6.8 (m, 3H), 7.3 (m, 1H).

249 1.0 (t, 3H), 1.7 (d, 6H), 1.7 (m, 1H), 1.9 (m, 1H), 3.0 (s, 1H), 3.9 (m 1H), 4.1 (m, 1H), 4.1 (m, 1H), 4.3 (m, 1H), 5.4 (m, 3H), 6.9 (m, 1H), 7.1 (m, 1H), 7.2 (m, 2H).

270 1.0 (t, 3H), 1.7 (d, 6H), 1.7 (m, 1H), 1.8 (m, 1H), 3.9 (m, 1H), 4.1 (m, 1H), 4.3 (m, 1 H), 5.4 (m, 3H), 6.9 (m, 2H), 7.3 (m, 2H).

271 1.0 (t, 3H), 1.7 (d, 6H), 1.7 (m, 1H), 1.9 (m, 1H), 3.9–4.4 (m, 3H), 5.5 (m, 3H), 6.8–7.2 (m, 4H).

272 1.0 (t, 3H), 1.7 (d, 6H), 1.7 (m, 1H), 1.9 (m, 1H), 3.9–4.4 (m, 3H),5.5 (m, 3H), 6.7–7.2 (m, 4H).

274 1.0 (t, 3H), 1.7 (d, 6H), 1.6 (m, 1H), 1.8 (m, 1H), 2.3 (s, 3H), 3.9 (m, 1H), 4.1 (m, 1H, 4.2 (m, 1H), 5.4 (m, 3H), 6.6 (m, 1H), 6.9 (m, 2H).

275 1.0 (t, 3H), 1.7 (d, 6H), 1.7 (m, 1H), 1.9 (m, 1H), 2.3 (s, 3H), 3.9 (m, 1H), 4.0 (m, 1H), 4.2 (m, 1H), 5.2 (m, 3H), 6.6–6.9 (m, 3H).

295 1.0 (t, 3H), 1.7 (d, 6H), 1.7 (m, 1H), 1.9 (m, 1H), 3.8–4.4 (m, 3H), 5.5 (m, 3H), 6.8–7.1 (m, 3H).

297a 1.0 (t, 3H), 1.7 (d, 6H), 1.7 (m, 1H), 1.9 (m, 1H), 3.9 (m, 1H), 4.2 (m, 2H), 5.4 (m, 3H), 7.0 (m, 1H), 7.1 (m, 2H).

299 1.0 (t, 3H), 1.7 (d, 6H), 1.7 (m, 1H), 1.9 (m, 1H), 4.1 (m, 2H), 4.4 (m, 1H), 5.4 (m, 3H), 6.8 (m, 1H), 7.1 (m, 2H).

301 1.0 (t, 3H), 1.7 (d, 6H), 1.7 (m, 1H), 1.8 (m, 1H), 4.0 (m, 1H), 4.1 (m, 1H), 4.3 (m, 1H), 5.5 (brd., 3H), 6.9–7.3 (m, 3H).

306 1.0 (t, 3H), 1.7 (d, 6H), 1.7 (m, 1H), 1.9 (m, 1H), 2.1 (s, 3H), 4.0 (m, 2H), 4.3 (m, 1H), 5.4 (m, 3H), 6.6 (m, 2H), 7.1 (m, 1H).

307a 1.0 (t, 3H), 1.7 (d, 6H), 1.7 (m, 1H), 1.9 (m, 1H), 2.1 (s, 3H), 4.0 (m, 2H), 4.3 (m, 1H), 5.4 (m, 3H), 6.5–7.1 (m, 3H).

314 1.0 (t, 3H), 1.7 (d, 6H), 1.7 (m, 1H), 1.9 (m, 1H), 3.8 (s, 3H), 3.9 (m, 1H), 4.1 (m, 1H), 4.3 (m, 1H), 5.5 (m, 3H), 6.2–6.5 (m, 3H).

322 1.0 (t, 3H), 1.6 (d, 6H), 1.7 (m, 1H), 1.8 (m, 1H), 3.9 (m, 1H), 4.1 (m, 1H), 4.0 (m, 1H), 4.3 (m, 1H), 5.4 (brd., 3H), 6.5–7.4 (m, 9H).

332 1.0 (t, 3H), 1.7 (d, 6H), 1.7 (m, 1H), 1.8 (m, 1H), 3.8 (s, 3H), 3.9 (m, 1H), 4.1 (m, 1H), 4.3 (m, 1H), 5.4 (m, 3H), 6.6 (m, 3H).

342 1.0 (t, 3H), 1.6 (d, 6H), 1.7 (m, 1H), 1.9 (m, 1H), 3.9 (m, 1H), 4.2 (m, 2H), 5.4 (m, 3H), 7.1 (m, 1H), 7.4 (m, 2H).

344 1.0 (t, 3H), 1.7 (d, 6H), 1.7 (m, 1H), 1.9 (m, 1H), 3.8 (s, 3H), 3.9 (m, 1H), 4.1 (m, 1H), 4.3 (m, 1H), 5.4 (m, 3H), 6.7–6.9 (m, 3H).

353 1.0 (t, 3H), 1.7 (d, 6H), 1.7 (m, 1H), 1.8 (m, 1H), 4.0 (m, 1H), 4.1 (m, 1H), 4.3 (m, 1H), 5.4 (m, 3H), 6.8 (m, 3H), 7.3 (m, 1H).

362 1.0 (t, 3H), 1.6 (d, 6H), 1.7 (m, 1H), 1.8 (m, 1H), 3.9 (m, 1H), 4.1 (m, 1H), 4.3 (m, 1H), 5.4 (brd., 3H), 5.9 (tt, 1H), 6.8 (m, 3H), 7.2 (m, 1H).

364 1.0 (t, 3H), 1.7 (d, 6H), 1.7 (m, 1H), 1.9 (m, 1H), 3.9–4.4 (m, 3H), 5.6 (m, 3H), 6.8–7.0 (m, 3H), 7.2 (m, 2H).

365 1.0 (t, 3H), 1.7 (d, 6H), 1.7 (m, 1H), 1.8 (m, 1H), 2.3 (s, 3H), 3.9 (m, 1H), 4.1 (m, 1H), 4.3 (m, 1H), 5.4 (brd., 3H), 6.7 (m, 3H), 7.2 (m, 1H).

366 1.0 (t, 3H), 1.7 (d, 6H), 1.7 (m, 1H), 1.8 (m, 1H), 2.3 (s, 6H), 3.9 (m, 1H), 4.0 (m, 1H), 4.3 (m, 1H), 5.4 (brd., 3H), 6.5 (s, 2H), 6.6 (s, 1H).

369 1.0 (t, 3H), 1.7 (d, 6H), 1.7 (m, 1H), 1.9 (m, 1H), 3.9–4.4 (m, 3H), 5.4 (m, 3H), 6.6–6.8 (m, 3H), 7.2 (m, 1H).

370 1.0 (t, 3H), 1.7 (d, 6H), 1.7 (m, 1H), 1.9 (m, 1H), 3.9–4.4 (m, 3H), 5.4 (m, 3H), 6.3–6.6 (m, 3H).

371 1.0 (t, 3H), 1.6 (d, 6H), 1.7 (m, 1H), 1.8 (m, 1H), 4.0 (m, 1H), 4.1 (m, 1H), 4.3 (m, 1H), 5.5 (brd., 3H), 7.0–7.2 (m, 3H), 7.4 (m, 1H).

372 1.0 (t, 3H), 1.7 (d, 6H), 1.7 (m, 1H), 1.9 (m, 1H), 3.8 (s, 3H), 3.9–4.4 (m, 3H), 5.6 (m, 3H), 6.4–6.7 (m, 3H), 7.2 (m, 1H).

373 1.0 (t, 3H), 1.7 (d, 6H), 1.7 (m, 1H), 1.9 (m, 1H), 3.8 (s, 6H), 3.9–4.4 (m, 3H), 5.5 (m, 3H), 6.0–6.3 (m, 3H).

380 1.0 (d, 6H), 1.7 (d, 6H), 2.1 (m, 1H), 3.9–4.3 (m, 3H), 5.5 (m, 3H), 6.8–7.0 (m, 3H), 7.2 (m, 2H).

381 1.0 (d, 6H),1.7 (d, 6H),2.1 (m, 1H),2.3 (s, 3H),3.9–4.3 (m, 3H), 5.4 (m, 3H), 6.6–6.8 (m, 3H), 7.1 (m, 1H).

382 1.0 (d, 6H), 1.7 (d, 6H), 2.2 (m, 1H), 3.9 (m, 1H), 4.1 (m, 2H), 5.4 (brd., 3H), 6.5 (s, 2H), 6.6 (s, 1H).

383 1.0 (d, 6H), 1.7 (d, 6H), 2.1 (m, 1H), 3.9–4.3 (m, 3H), 5.4 (m, 3H), 6.6–6.8 (m, 3H), 7.2 (m, 1H).

384 1.0 (d, 6H), 1.7 (d, 6H), 2.1 (m, 1H), 3.9–4.3 (m, 3H), 5.3 (m, 3H), 6.7–7.3 (m, 4H).

387 1.0 td, 6H), 1.7 (d, 6H), 2.1 (m, 1H), 3.8 (s, 3H), 4.0–4.3 (m, 3H), 5.3 (m, 3H), 6.4–6.7 (m, 3H), 7.2 (m, 1H).

405 0.3–0.6 (m, 4H), 1.2 (m, 1H), 1.7 (d, 6H), 3.7 (m, 1H), 4.0–4.2 (m, 2H), 5.4 (m, 3H), 6.8–7.0 (m, 3H), 7.3 (m, 2H).

406 0.3–0.6 (m, 4H), 1.2 (m, 1H), 1.7 (d, 6H), 2.3 (s, 3H), 3.7 (m, 1H), 4.0–4.2 (m, 2H), 5.5 (m, 3H), 6.6–6.8 (m, 3H), 7.1 (m, 1H).

410 0.3–0.6 (m, 4H), 1.2 (m, 1H), 1.7 (d, 6H), 3.7 (m, 1H), 4.0–4.2 (m, 2H), 5.5 (m, 3H) 6.6–6.8 (m, 3H), 7.2 (m, 1H).

411 0.3–0.6 (m, 4H), 1.2 (m, 1H), 1.6 (d, 6H), 3.7 (m, 1H), 4.0–4.2 (m, 2H), 5.6 (m, 3H), 6.8–7.3 (m, 4H).

414 0.3–0.6 (m, 2H), 0.9 (m, 1H), 1.1–1.3 (m, 2H), 1.7 (d, 6H), 3.7 (m, 1H), 3.9 (s, 3H), 4.0–4.2 (m, 2H), 5.6 (m, 3H), 6.4–6.5 (m, 3H), 7.2 (m, 1H).

415 0.3–0.6 (m, 4H), 1.2 (m, 1H), 1.7 (d, 6H), 3.7 (m, 1H), 4.0–4.2 (m, 2H), 5.4 (m, 3H), 6.3–6.6 (m, 3H).

427 0.3–0.6 (m, 2H), 0.9 (m, 1H), 1.1–1.3 (m, 2H), 1.7 (d, 6H), 3.7 (m, 1H), 3.8 (s, 3H), 4.0–4.2 (m, 2H), 5.4 (m, 3H), 6.4–6.7 (m, 3H).

455 1.4 (d, 3H), 1.9 (s, 6H), 3.9 (m, 1H), 4.1 (m, 1H), 4.4 (m, 1H), 5.4 (m, 3H), 6.8 (m, 1H), 6.9 (m, 1H), 7.2 (m, 2H).

463 1.4 (d, 3H), 1.9 (s, 6H), 2.3 (s, 3H), 3.9 (m, 1H), 4.0 (m, 1H), 4.4 (m, 1H), 5.3 (m, 3H), 6.6–6.9 (m, 3H).

465 1.4 (d, 3H), 1.9 (s, 6H), 2.3 (s, 3H), 3.9 (m, 1H), 4.0 (m, 1H), 4.4 (m, 1H), 5.2 (m, 3H), 6.7 (m, 1H), 7.1 (m, 2H).

483 1.0 (t, 3H), 1.2 (d, 6H), 1.4 (d, 3H), 1.5 (dt, 2H), 1.8 (dd, 2H), 2.7 (m, 1H), 3.9 (m, 3H), 4.1 (m, 1H), 4.4.(m, 1H), 5.4 (m, 3H), 6.5 (m, 2H), 6.8 (m, 1H), 7.2 (m, 1H).

486 1.0 (t, 6H), 1.2 (d, 6H), 1.3 (d, 3H), 1.8 (tq, 4H), 2.7 (m, 1H), 3.8 (m, 1H), 3.9 (t, 4H), 4.1 (m, 1H), 4.4 (m, 1H), 5.3 (m, 3H), 6.1 (s, 1H), 6.3 (s, 2H).

487 1.2 (d, 6H), 1.4 (d, 3H), 2.7 (m, 1H), 3.9 (m, 1H), 4.1 (m, 1H), 4.4 (m, 1H), 5.2 (m, 3H), 7.3 (m, 4H).

488 1.2 (d, 6H), 1.3 (m, 9H), 2.3 (s, 3H), 2.7 (m, 1H), 3.9 (m, 1H), 4.1 (m, 1H), 4.4 (m, 1H), 4.5 (m, 1H), 5.4 (d, 1H), 5.6 (brd., 2H), 6.3 (s, 2H), 6.6 (s, 1H).

490 1.0 (t, 3H) 1.2 (d, 6H), 1.7 (m, 1H), 1.9 (m, 1H), 2.7 (m, 1H), 4.1 (m, 2H), 4.3 (m, 1H), 5.2 (m, 3H), 6.9 (m, 1H), 7.1 (m, 2H). 492 1.4 (d, 3H), 1.6 (d, 6H), 2.3 (s, 3H), 3.9 (m, 1H), 4.0 (m, 1H), 4.4 (m, 1H), 5.5 (brd., 3H), 6.7 (m, 3H), 7.1 (m, 2H).

493 1.4 (d, 3H), 1.7 (d, 6H), 2.2 (s, 3H), 3.9 (m, 1H), 4.1 (m, 1H), 4.4 (m, 1H), 5.4 (m, 3H), 6.8 (m, 1H), 7.0 (m, 2H).

496 1.3 (m, 9H), 1.7 (d, 6H), 2.3 (s, 3H), 3.9 (m, 1H), 4.1 (m, 1H), 4.3 (m, 1H), 4.5 (m, 1H), 5.4 (m, 1H), 5.6 (brd., 2H), 6.3 (s, 2H), 6.6 (s, 1H).

500 1.0 (t, 3H). 1.6 (d, 6H), 1.7 (m, 1H), 1.8 (m, 1H), 2.3 (s, 3H), 3.9 (m 1H), 4.0 (m, 1H), 4.3 (m, 1H), 5.5 (brd., 3H), 6.7 (m, 3H), 7.1 (m, 2H).

TABLE 2

Compounds of the formula (1b)

(1b)

| No. | $R^2$ | $R^3$ | $R^4$ | $R^5$ | $R^6$ | X | $(R^7)_n$ | Phys. data |
|---|---|---|---|---|---|---|---|---|
| 2-1 | H | H | H | Me | H | NH | 3,5-Me$_2$ | |
| 2-2 | H | H | H | Me | H | NH | 3,5-F$_2$ | |
| 2-3 | NH$_2$ | H | H | Me | H | O | 3-Me | |

TABLE 2-continued

Compounds of the formula (1b)

(1b)

| No. | $R^2$ | $R^3$ | $R^4$ | $R^5$ | $R^6$ | X | $(R^7)_n$ | Phys. data |
|---|---|---|---|---|---|---|---|---|
| 2-4 | NH$_2$ | H | H | Me | H | O | 3,5-Me$_2$ | |
| 2-5 | NH$_2$ | H | H | Me | H | O | 3-F | |
| 2-6 | NH$_2$ | H | H | Me | H | O | 3,5-F$_2$ | |
| 2-7 | CHO | H | H | Me | H | O | 3,5-Me$_2$ | |
| 2-8 | CHO | H | H | Me | H | O | 3,5-F$_2$ | |
| 2-9 | Me | H | H | Me | H | O | 3,5-Me$_2$ | |
| 2-10 | Me | H | H | Me | H | O | 3,5-F$_2$ | |
| 2-11 | H | H | Me | H | H | O | 3,5-Me$_2$ | |
| 2-12 | H | H | Me | H | H | O | 3,5-F$_2$ | |
| 2-13 | H | H | H | Me | Me | O | 3,5-Me$_2$ | |
| 2-14 | H | H | H | Me | Me | O | 3,5-F$_2$ | |
| 2-15 | H | H | H | Ph | H | O | 3-Me | |
| 2-16 | H | H | H | Ph | H | O | 3,5-Me$_2$ | NMR |
| 2-17 | H | H | H | Ph | H | O | 3-F | |
| 2-18 | H | H | H | Ph | H | O | 3-Cl | |
| 2-19 | H | H | H | Ph | H | O | 3-Br | |
| 2-20 | H | H | H | Ph | H | O | 3-I | |
| 2-21 | H | H | H | Ph | H | O | 3,5-F$_2$ | |
| 2-22 | H | H | H | Ph | H | O | 3-CF$_3$ | |
| 2-23 | H | H | H | Ph | H | O | 3-OMe$_2$ | |
| 2-24 | H | H | H | Ph | H | O | 3,4-Cl$_2$ | NMR |
| 2-25 | H | H | H | H | Ph | O | 3-F | |
| 2-26 | H | H | H | H | Ph | O | 3-Cl | |
| 2-27 | H | H | H | H | H | O | H | |
| 2-28 | H | H | H | H | H | O | 3,5-Me$_2$ | |
| 2-29 | H | H | H | H | H | O | 3,5-F$_2$ | |
| 2-30 | H | H | H | H | H | NH | 3,5-F$_2$ | |
| 2-31 | H | H | H | H | H | NH | 3,5-Me$_2$ | |
| 2-32 | H | H | H | H | H | NH | 3,5-F$_2$ | |
| 2-33 | H | H | H | Ph | H | O | H | |
| 2-34 | H | H | H | Pr | H | O | 3-Me | NMR |
| 2-35 | H | H | H | Pr | H | O | 3,5-Me$_2$ | |
| 2-36 | H | H | H | Pr | H | O | 3-F | NMR |
| 2-37 | H | H | H | Pr | H | O | 3,5-F$_2$ | |
| 2-38 | H | H | H | Pr | H | O | 3-Cl | NMR |
| 2-39 | H | H | H | Pr | H | O | 3-Br | |
| 2-40 | H | H | H | Pr | H | O | 3-I | |
| 2-41 | H | H | H | Pr | H | O | H | NMR |
| 2-42 | H | H | H | Pr | H | O | 3-CF$_3$ | |
| 2-43 | H | H | H | Pr | H | O | 3-OMe | |
| 2-44 | NH$_2$ | H | H | Me | H | O | 3-Cl | |
| 2-45 | NH$_2$ | H | H | Me | H | NH | 3-Cl | |
| 2-46 | NH$_2$ | H | H | Et | H | O | 3-Cl | |
| 2-47 | NH$_2$ | H | H | Et | H | NH | 3-Cl | |
| 2-48 | NH$_2$ | H | H | Pr | H | O | 3-Cl | |
| 2-49 | NH$_2$ | H | H | Pr | H | NH | 3-Cl | |
| 2-50 | NH$_2$ | H | H | i-Pr | H | O | 3-Cl | |
| 2-51 | NH$_2$ | H | H | i-Pr | H | NH | 3-Cl | |
| 2-52 | NH$_2$ | H | H | c-Pr | H | O | 3-Cl | |
| 2-53 | NH$_2$ | H | H | c-Pr | H | NH | 3-Cl | |

$^1$H NMR data (CDCl$_3$, 300 MHz, δ reference to TMS standard) of the compounds of the formula (1b) of Table 2: Example No./NMR Data 2-16 1.7 (d, 6H), 4.3 (d, 2H), 5.4 (brd., 3H), 6.0 (brd., 1H), 6.5 (s, 2H), 6.6 (brd., 1H), 7.3 (m, 5H).

2-24 1.7 (d, 6H), 4.3 (d, 2H), 5.4 (brd., 3H), 6.0 (brd., 1H), 6.8 (brd., 1H), 7.0–7.4 (m, 7H).

2-34 0.9 (t, 3H), 1.4 (m, 2H), 1.6–1.8 (m, 8H), 2.3 (s, 3H), 3.9–4.1 (m, 2H), 4.4 (m, 1H), 5.5 (m, 3H), 6.6–6.8 (m, 3H), 7.2 (m, 1H).

2-36 0.9 (t, 3H), 1.4–1.8 (m, 10H), 3.9–4.1 (m, 2H), 4.3 (m, 1H), 5.3 (m, 3H), 6.6–6.8 (m, 3H), 7.2 (m, 1H).

2-38 0.9 (t, 3H), 1.4–1.8 (m, 4H), 1.7 (d, 6H), 3.9 (m, 1H), 4.0 (m, 1H), 4.3 (m, 1H), 5.5 (m, 3H), 6.8 (m, 1H), 6.9 (m, 1H), 7.1 (m, 2H).

2-41 0.9 (t, 3H), 1.4–1.8 (m, 10H), 3.9 (m, 1H), 4.1 (m, 2H), 4.4 (m, 1H), 5.6 (m, 3H), 6.8–7.0 (m, 3H), 7.2 (m, 2H).

B. Formulation Examples a) A dusting agent is obtained by mixing 10 parts by weight of a compound of the formula (I) and 90 parts by weight of talc as inert substance and comminuting the mixture in a hammer mill.

b) A readily water-dispersible wettable powder is obtained by mixing 25 parts by weight of a compound of the formula (I), 64 parts by weight of kaolin-containing quartz as inert material, 10 parts by weight of potassium ligninsulfonate and 1 part by weight of sodium oleoylmethyltaurinate as wetting agent and dispersant and grinding the mixture in a pinned disk mill.

c) A readily water-dispersible dispersion concentrate is obtained by mixing 20 parts by weight of a compound of the formula (I) and 6 parts by weight of alkylphenol polyglycol ether (®Triton X 207), 3 parts by weight of isotridecanol polyglycol ether (8 EO) and 71 parts by weight of paraffinic mineral oil (boiling range for example from about 255 to over 277° C.) and grinding the mixture in a ball mill to a fineness below 5 microns.

d) An emulsifiable concentrate is obtained from 15 parts by weight of a compound of the formula (I), 75 parts by weight of cyclohexanone as solvent and 10 parts by weight of ethoxylated nonylphenol as emulsifier.

e) Water-dispersible granules are obtained by mixing 75 parts by weight of a compound of the formula (I), 10 parts by weight of calcium ligninsulfonate, 5 parts by weight of sodium lauryl sulfate, 3 parts by weight of polyvinyl alcohol, and 7 parts by weight of kaolin, grinding the mixture in a pinned disk mill and granulating the powder in a fluidized bed by spraying on water as granulation liquid.

f) Water-dispersible granules are also obtained by homogenizing and precomminuting 25 parts by weight of a compound of the formula (I), 5 parts by weight of sodium 2,2'-dinaphthylmethane-6,6'-disulfonate, 2 parts by weight of sodium oleoylmethyltaurinate, 1 part by weight of polyvinyl alcohol, 17 parts by weight of calcium carbonate, and 50 parts by weight of water, in a colloid mill, followed by grinding in a bead mill, and atomizing and drying the resulting suspension in a spray tower, using a single-substance nozzle.

C. Biological Examples

1. Preemergence Action Against Weeds

Seeds or rhizome pieces of monocotyledonous or dicotyledonous weed plants are placed in sandy loam soil in cardboard pots and covered with soil. The novel compounds, formulated as wettable powders or emulsion concentrates, are then applied to the surface of the soil cover in the form of an aqueous suspension or emulsion at an application rate of from 600 to 800 l of water/ha (converted), in various dosages.

After the treatment, the pots are placed in a greenhouse and kept under good growth conditions for the weeds. After the test plants have emerged after a trial period of 3 to 4 weeks, the damage to the plants or the negative effect on emergence is rated visually by comparison with untreated controls. As shown by the test results, the novel compounds have a good herbicidal pre-emergence activity against a broad spectrum of gramineous and broad-leaved weeds. For example, the Example Nos.1, 4, 5, 6, 7, 11, 12, 19, 24, 26, 27, 39, 42, 44, 45, 51 to 56, 62, 64, 65, 68, 69, 70, 76, 77, 79, 80, 83, 101, 102, 106–111, 123, 126, 130, 134, 148, 149, 151, 152, 153, 154, 155, 156, 172, 175, 176, 178a, 180, 182, 186, 187a, 188a, 189, 193, 195, 200, 202, 203, 205, 208, 209, 213, 218, 222, 225, 234, 243, 249, 270, 271, 272, 274, 275, 295, 297a, 299, 301, 306a, 307a, 314, 322, 332, 342, 344, 353, 362, 364, 365, 366, 369, 370, 371, 372, 373, 380, 381, 382, 384, 386, 405, 406, 410, 411, 414, 415, 427, 455, 463, 465, 486, 487, 490, 492, 493, 496, 500, 2-16, 2-19, 2-24, 2-26, 2-39, 242 and 245 (see Tables 1 and 2) show herbicidal activity, in most cases very good herbicidal activity, in the test against harmful plants such as Stellaria media, Matricaria inodora, Sorghum halepense, Digitaria adscendens, Setaria pumila, Avena fatua, Galium aparine, Polygonum persicaria, Veronica persica, Amaranthus retroflexus, Xanthium orientate, chenopodium album, Pharbitis purpurea, Abutilon theophrasti, Lamium purpureum, Viola tricolor and Echinochloa crus-galli when applied pre-emergence at a rate of 1.25 kg of active substance per hectare.

2. Post-emergence Action Against Weeds

Seeds or rhizome pieces of monocotyledonous and dicotyledonous weeds are placed in sandy loam soil in cardboard pots, covered with soil and cultivated in a greenhouse under good growth conditions. Two to three weeks after sowing, the test plants are treated at the three-leaf stage. The novel compounds, formulated as wettable powders or emulsion concentrates, are sprayed in various dosages onto the green parts of the plants at an application rate of from 600 to 800 l of water/ha (converted), and, after the test plants have remained in the greenhouse for about 3 to 4 weeks under optimum growth conditions, the action of the preparations is rated visually by comparison with untreated controls. The novel compositions also have a good post-emergence herbicidal activity against a broad spectrum of economically important gramineous and broad-leaved weeds. For example, Example Nos. 1, 4, 5, 6, 7, 11, 12,19, 24, 26, 27, 39, 42, 44, 45, 51 to 56, 62, 64, 65, 68, 69, 70, 76, 77, 79, 80, 83, 101, 102, 106–111, 123, 126, 130, 134, 148, 149, 151, 152, 153, 154, 155, 156, 172, 175, 176, 178a, 180, 182, 186, 187a,188a, 189, 193, 195, 200, 202, 203, 205, 208, 209, 213, 218, 222, 225, 234, 243, 249, 270, 271, 272, 274, 275, 295, 297a, 299, 301, 306a, 307a, 314, 322, 332, 342, 344, 353, 362, 364, 365, 366, 369, 370, 371, 372, 373, 380, 381, 382, 384, 386, 405, 406, 410, 411, 414, 415, 427, 455, 463, 465, 486, 487, 490, 492, 493, 496, 500, 2-16, 2-19, 2-24, 2-26, 2-39, 2-42 and 245 (see Tables 1 and 2) show herbicidal activity, in most cases very good herbicidal activity, in the test against harmful plants such as Sorghum halepense, Digitaria adscendens, Setaria pumila, Avena fatua, Galium aparine, Polygonum persicaria, Veronica persica, Amaranthus retroflexus, Xanthium orientate, Chenopodium album, Pharbitis purpurea, Abutilon theophrasti, Lamium purpureum, Viola tricolor, Echinochloa crusgalli, Stellaria media, Matricaria inodora, Cyperus iria and Avena sativa when applied post-emergence at a rate of 1.25 kg or less of active substance per hectare.

3. Action on Weeds in Rice

Transplanted and sown rice and also typical rice weeds (gramineous and broad-leaved) are cultivated in closed plastic pots in a greenhouse to the three-leaf stage (Echinochloa 1.5-leaf) under paddy rice conditions (dammed height of water: 2–3 cm). This is followed by treatment with the novel compounds. For this purpose the formulated active compounds are suspended, dissolved or emulsified in water and applied by pouring them into the dammed water around the test plants in different dosages. After this treatment, the test plants are set up in a greenhouse under optimum growth conditions and are maintained in this way under these conditions throughout the test period. About three weeks after application, evaluation is made by visual rating of the damage to the plants by comparison with untreated controls, in which case, for example, the compounds of Example Nos.1, 4, 5, 6, 7, 11, 12, 19, 24, 26, 27, 39, 42, 44, 45, 51 to 56, 62, 64, 65, 68, 69, 70, 76, 77, 79, 80, 83, 101, 102, 106–111, 123, 126, 130, 134, 148, 149, 151, 152, 153, 154, 155, 156, 172, 175, 176, 178a, 180, 182, 186, 187a, 188a, 189, 193, 195, 200, 202, 203, 205, 208, 209, 213, 218, 222, 225, 234, 243, 249, 270, 271, 272, 274, 275, 295, 297a, 299, 301, 306a, 307a, 314, 322, 332, 342, 344, 353, 362, 364, 365, 366, 369, 370, 371, 372, 373, 380, 381, 382, 384, 386, 405, 406, 410, 411, 414, 415, 427, 455, 463, 465, 486, 487, 490, 492, 493, 496, 500, 2-16, 2-19, 2-24, 2-26, 2-39, 242 and 245 (see Tables 1 and 2) in the test show very good herbicidal activity in the test against harmful plants which are typical for rice crops, for example *Cyperus monti, Eleocharis acicularis, Echinochloa crusgalli* and *Sagittaria pygmaea*.

4. Tolerance by Crop Plants

In further greenhouse experiments, seeds of a relatively large number of crop plants and weeds are placed in sandy loam soil and covered with soil. Some of the pots are treated immediately as described under Section 1, while the remainder are placed in a greenhouse until the plants have developed two to three true leaves, and then sprayed with various dosages of the novel substances of the formula (I), as described in Section 2. Four to five weeks after the application, and after the plants have remained in the greenhouse, visual rating shows that the novel compounds leave dicotyledonous crops such as, for example, soya, cotton, oil seed rape, sugar beet and potatoes undamaged when employed pre- and post-emergence, even when high dosages of active compound are used. Moreover, some substances also leave gramineous crops unharmed, for example barley, wheat, rye, Sorghum species, maize or rice. Some of the compounds of the formula (I) display a high selectivity and are therefore suitable for controlling unwanted plant growth in agricultural crops.

What is claimed is:

1. A compound of the formula (I) or salt thereof

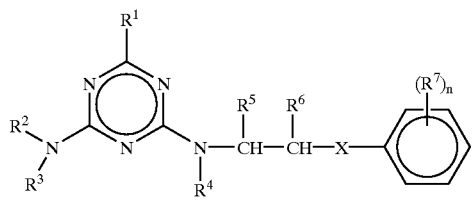

(I)

in which $R^1$ is $(C_1-C_4)$alkyl, $(C_1-C_4)$haloalkyl, $(C_1-C_4)$hydroxyalkyl, $(C_1-C_4)$alkoxy-$(C_1-C_4)$-alkyl or benzyl, $R^2$ and $R^3$ independently of one another are hydrogen, amino, formyl, $(C_1-C_4)$alkyl, $(C_1-C_4)$alkoxy-$(C_1-C_4)$alkyl, $(C_2-C_6)$alkenyl, $(C_2-C_6)$ alkynyl, $(C_1-C_4)$alkylamino-$(C_1-C_4)$alkyl, di-$[(C_1-C_4)$alkyl]-amino-$(C_1-C_4)$alky or phenyl, phenyl-$(C_1-C_4)$alkyl or phenoxycarbonyl or one of the three last-mentioned radicals which is substituted up to three times in the phenyl moiety by radicals of the group consisting of halogen, $(C_1-C_4)$alkyl, $(C_1-C_4)$alkoxy and $(C_1-C_4)$alkoxy-carbonyl, or $R^2$ and $R^3$, together with the nitrogen atom of the group $NR^2R^3$, are a heterocyclic radical having 3 to 6 ring atoms and 1 to 2 hetero-ring atoms, any further hetero-ring atoms in addition to the nitrogen atom being selected from the group consisting of N and O, and the radical being unsubstituted or substituted by one or more radicals from the group consisting of halogen, $(C_1-C_4)$alkyl and oxo, $R^4$ is hydrogen, amino, formyl, $(C_1-C_4)$alkyl, di-$[(C_1-C_4)$alkyl]-amino, $(C_1-C_4)$alkoxy-$(C_1-C_4)$alkyl, $(C_2-C_6)$alkenyl, $(C_2-C_6)$alkynyl, $(C_1-C_4)$dialkylamino-$(C_1-C_4)$alkyl, phenyl, phenoxy-$(C_1-C_4)$alkyl, phenyl-$(C_1-C_4)$alkyl, phenoxy-carbonyl, phenylaminocarbonyl or one of the five last-mentioned radicals which is mono-to trisubstituted in the phenyl moiety by radicals from the group consisting of halogen, $(C_1-C_4)$alkyl, $(C_1-C_4)$alkoxy and $(C_1-C_4)$alkoxy-carbonyl, $R^5$ is ethyl, n-propyl, i-propyl, n-butyl, i-butyl, sec-butyl, and tert-butyl, $R^6$ hydrogen, $(C_1-C_4)$alkyl, $(C_3-C_6)$cycloalkyl, $(C_1-C_4)$alkoxy-$(C_1-C_4)$alkyl, $(C_2-C_6)$alkenyl, $(C_2-C_6)$alkynyl, di-$[(C_1-C_4)$-alkyl]amino-$(C_1-C_4)$alkyl, phenyl, phenoxy-$(C_1-C_4)$alkyl, phenyl-$(C_1-C_4)$alkyl or one of the three last-mentioned radicals which is mono- to trisubstituted in the phenyl moiety by radicals from the group consisting of halogen, $(C_1-C_4)$alkyl, $(C_1-C_4)$alkoxy and $(C_1-C_4)$alkoxy-carbonyl, or $R^5$ and $R^6$ together are an alkylene chain having 2 to 4 carbon atoms which is unsubstituted or substituted by one or more radicals from the group consisting of halogen, $(C_1-C_4)$alkyl and oxo, $(R^7)n$ are n radicals $R^7$ which, in the case of n=2, 3, 4 or 5, are identical or different, $R^7$ in each case being halogen, hydroxyl, amino, nitro, formyl, aminocarbonyl, carboxyl, cyano, thiocyanato, $(C_1-C_6)$alkyl, $(C_1-C_4)$alkoxy, halo-$(C_1-C_4)$alkyl, halo-$(C_1-C_4)$alkoxy, hydroxy-$(C_1-C_4)$alkyl, hydroxy-$(C_1-C_4)$alkoxy, $(C_1-C_4)$alkoxy-$(C_1-C_4)$alkyl, $(C_1-C_4)$alkoxy-$(C_1-C_4)$-alkoxy, halo-$(C_1-C_4)$alkoxy-$(C_1-C_4)$alkyl, halo-$(C_1-C_4)$alkoxy-$(C_1-C_4)$alkoxy, $(C_3-C_6)$cycloalkyl, halo-$(C_3-C_6)$cycloalkyl, $(C_2-C_6)$alkenyl, halo-$(C_2-C_6)$alkenyl, $(C_2-C_6)$alkynyl, halo-$(C_2-C_6)$alkynyl, $(C_1-C_4)$alkylcarbonyl, $(C_1-C_4)$haloalkylcarbonyl, $(C_3-C_6)$cycloalkyloxy, halo-$(C_3-C_6)$cycloalkyloxy, $(C_3-C_6)$cycloalkylcarbonyl, halo-$(C_3-C_6)$cycloalkylcarbonyl, $(C_1-C_4)$alkoxycarbonyl, halo-$(C_1-C_4)$alkoxycarbonyl, $(C_1-C_4)$alkylcarbonyloxy, halo-$(C_1-C_4)$alkylcarbonyloxy, $(C_1-C_4)$alkylcarbonyl-$(C_1-C_4)$alkyl, $(C_1-C_4)$alkoxycarbonyl-$(C_1-C_4)$alkyl, $(C_1-C_4)$alkylcarbonyloxy-$(C_1-C_4)$alkyl, $(C_1-C_4)$alkylthio, halo-$(C_1-C_4)$alkylthio, $(C_1-C_4)$alkylamino, di-$[(C_1-C_4)$alkyl]-amino, $(C_1-C_6)$alkanoylamino, N-$[(C_1-C_6)$alkanoyl]-N-$[(C_1-C_4)$alkyl]-amino, $(C_1-C_6)$alkanoylamino-$(C_1-C_4)$alkyl, N-$[(C_1-C_6)$alkanoyl]-N-$[(C_1-C_4)$alkyl]-amino-$(C_1-C_4)$alkyl or phenyl, phenoxy, phenylcarbonyl, phenoxycarbonyl, phenylcarbonyloxy, phenoxy-$(C_1-C_4)$alkyl, phenylcarbonyl-$(C_1-C_4)$alkyl, phenyl-$(C_1-C_4)$alkyl, phenyl-$(C_2-C_6)$-alkenyl, phenyl-$(C_1-C_6)$alkynyl, or one of the 10 last-mentioned radicals which is substituted in the cyclic moiety by one or more radicals from the group consisting of halogen, hydroxyl, nitro, $(C_1-C_4)$alkyl, $(C_1-C_4)$alkoxy, $(C_1-C_4)$alkylthio, $(C_1-C_4)$-haloalkyl and $(C_1-C_4)$haloalkoxy, or two adjacent radicals $R^7$ together are a fused-on cycle having 4 to 6 ring atoms which is carbocyclic and which is unsubstituted or substituted by one or more radicals from the group consisting of halogen, $(C_1-C_4)$ alkyl and oxo, X is a group of the formula —O— or —NR*—, R* being hydrogen or methyl, and n is 0, 1, 2, 3, 4 or 5;

or wherein a1) R1 is $(C_1-C_4)$haloalkyl,
$R^2$, $R^3$, $R^4$, $R^6$ are each hydrogen,
$R^5$ is methyl,
n is the number 3, 4 or 5,
X is an oxygen atom and
$(R^7)n$ are n radicals $R^7$ which are identical or different, $R^7$ in each case being halogen, hydroxyl, amino, nitro, formyl, carboxyl, cyano, $(C_1-C_6)$alkyl, $(C_1-C_4)$alkoxy, halo-$(C_1-C_4)$alkyl, halo-$(C_1-C_4)$alkoxy, hydroxy-$(C_1-C_4)$alkyl, hydroxy-$(C_1-C_4)$alkoxy, $(C_1-C_4)$alkoxy-$(C_1-C_4)$alkyl, halo-$(C_1-C_4)$alkoxy-$(C_1-C_4)$alkyl, halo-$(C_1-C_4)$alkyloxy-$(C_1-C_4)$-alkoxy, $(C_1-C_4)$alkoxy-$(C_1-C_4)$alkoxy, $(C_3-C_6)$cycloalkyl, halo-$(C_3-C_6)$cycloalkyl, $(C_1-C_4)$alkenyl, halo-$(C_2-C_4)$alkenyl, $(C_2-C_4)$alkynyl, halo-$(C_2-C_4)$alkynyl, $(C_1-C_4)$alkylcarbonyl, $(C_1-C_4)$alkoxycarbonyl, $(C_1-C_4)$alkylcarbonyloxy, $(C_1-C_4)$alkylcarbonyl-$(C_1-C_4)$alkyl, $(C_1-C_4)$alkylthio, $(C_1-C_4)$alkylamino, di-[$(C_1-C_4)$-alkyl]-amino or phenyl, phenoxy, phenylcarbonyl, phenoxycarbonyl, phenylcarbonyloxy, phenoxy-$(C_1-C_4)$alkyl, phenylcarbonyl-$(C_1-C_4)$alkyl, phenyl-$(C_1-C_4)$ alkyl or one of the 8 last-mentioned radicals which is substituted in the phenyl moiety by one or more radicals from the group consisting of halogen, $(C_1-C_4)$alkyl, $(C_1-C_4)$alkoxy, $(C_1-C_4)$haloalkyl and $(C_1-C_4)$haloalkoxy, or two adjacent radicals $R^7$ together are a fused-on cycle having 4 to 6 ring atoms, which is carbocyclic and which is unsubstituted or substituted by one more radicals $(C_1-C_4)$alkyl, or a2) $R^1$ is $(C_1-C_4)$haloalkyl,
$R^2$, $R^3$, $R^4$, $R^6$ are each hydrogen,
$R^5$ is methyl,
n is the number 1 or 2,
X is an oxygen atom,
$(R^7)_n$ are n radicals $R^7$ which, in the case of n=2, are defined the same, $R^7$ in each case being chlorine, bromine, iodine, hydroxyl, amino, nitro, formyl, carboxyl, cyano, $(C_2-C_4)$alkoxy, methyl which is substituted by one or more radicals from the group consisting of chlorine, bromine and iodine, $(C_2-C_4)$ haloalkyl, halo-$(C_1-C_4)$alkoxy, hydroxy-$(C_1-C_4)$ alkyl, hydroxy-$(C_1-C_4)$alkoxy, $(C_1-C_4)$alkoxy-$(C_1-C_4)$alkyl, halo-$(C_1-C_4)$alkoxy-$(C_1-C_4)$alkyl, halo-$(C_1-C_4)$alkyloxy-$(C_1-C_4)$alkoxy, $(C_1-C_4)$ alkoxy-$(C_1-C_4)$alkoxy, $(C_3-C_6)$cycloalkyl, halo-$(C_3-C_6)$cycloalkyl, $(C_2-C_4)$alkenyl, halo-$(C_2-C_4)$ alkenyl, $(C_2-C_4)$alkynyl, halo-$(C_2-C_4)$alkynyl, $(C_1-C_4)$alkylcarbonyl, $(C_1-C_4)$alkoxycarbonyl, $(C_1-C_4)$alkylcarbonyloxy, $(C_1-C_4)$alkylcarbonyl-$(C_1-C_4)$alkyl, $(C_1-C_4)$alkylthio, $(C_1-C_4)$ alkylamino, di-[$(C_1-C_4)$alkyl]-amino or phenyl, phenoxy, phenylcarbonyl, phenoxycarbonyl, phenylcarbonyloxy, phenoxy-$(C_1-C_4)$alkyl, phenylcarbonyl-$(C_1-C_4)$alkyl, phenyl-$(C_1-C_4)$alkyl or one of the 8 last-mentioned radicals which is substituted in the phenyl moiety by one or more radicals from the group consisting of halogen, $(C_1-C_4)$alkyl, $(C_1-C_4)$alkoxy, $(C_1-C_4)$haloalkyl and $(C_1-C_4)$haloalkoxy, or two adjacent radicals $R^7$ together are a fused-on cycle having 4 to 6 ring atoms, which is carbocyclic and which is unsubstituted or substituted by one or more radicals $(C_1-C_4)$alkyl, or a3) $R^1$ is $(C_1-C_4)$haloalkyl,
$R^2$, $R^3$, $R^4$, $R^6$ are each hydrogen,
$R^5$ is methyl,
n is the number 2,
X is an oxygen atom and
$(R^7)_n$ are the two radicals $R^7$, the two radicals $R^7$ being structurally different and otherwise as defined above under a1), or else two adjacent radicals $R^7$ together are a fused-on cycle having 4 to 6 ring atoms, which is carbocyclic and which is unsubstituted or substituted by one or more radicals $(C_1-C_4)$alkyl, or b1) $R^1$ is $(C_1-C_4)$,alkyl which is unsubstituted or substituted by 1 to 4 substituents from the group consisting of $(C_1-C_4)$alkoxy and hydroxyl,
$R^2$, $R^3$, $R^4$, $R^6$ are each hydrogen,
$R^5$ is methyl,
n is the number 1, 2, 3 or 4,
X is an oxygen atom and
$(R^7)_n$ are n radicals $R^7$ which, in the case of n=2, 3 or 4, are identical or different, $R^7$ in each case being hydroxvl, amino, nitro, formyl, carboxyl, cyano, $(C_1-C_4)$alkoxy, halo-$(C_1-C_4)$alkyl, halo-$(C_1-C_4)$ alkoxy, hydroxy-$(C_1-C_4)$alkyl, hydroxy-$(C_1-C_4)$ alkoxy, $(C_1-C_4)$alkoxy-$(C_1-C_4)$alkyl, halo-$(C_1-C_4)$ alkoxy-$(C_1-C_4)$alkyl, halo-$(C_1-C_4)$alkyloxy-$(C_1-C_4)$-alkoxy, $(C_1-C_4)$alkoxy-$(C_1-C_4)$alkoxy, $(C_3-C_6)$cycloalkyl, halo-$(C_3-C_6)$cycloalkyl, $(C_2-C_4)$alkenyl, halo-$(C_2-C_4)$alkenyl, $(C_2-C_4)$ alkynyl, halo-$(C_2-C_4)$alkynyl, $(C_1-C_4)$ alkylcarbonyl, $(C_1-C_4)$alkoxycarbonyl, $(C_1-C_4)$ alkylcarbonyloxy, $(C_1-C_4)$alkylcarbonyl-$(C_1-C_4)$ alkyl, $(C_1-C_4)$alkylthio, halo-$(C_1-C_4)$alkylthio, $(C_1-C_4)$alkylamino, di-$(C_1-C_4)$-alkyl]-amino or phenyl, phenoxy, phenylcarbonyl, phenoxycarbonyl, phenylcarbonyloxy, phenoxy-$(C_1-C_4)$alkyl, phenylcarbonyl-$(C_1-C_4)$alkyl, phenyl-$(C_1-C_4)$ alkyl or one of the 8 last-mentioned radicals which is substituted in the phenyl moiety by one or more radicals from the group consisting of halogen, $(C_1-C_4)$alkyl, $(C_1-C_4)$alkoxy, $(C_1-C_4)$haloalkyl and $(C_1-C_4)$haloalkoxy, or two adjacent radicals $R^7$ together are a fused-on cycle having 4 to 6 ring atoms, which is carbocyclic and which is unsubstituted or substituted by one or more radicals $(C_1-C_4)$alkyl.

2. A compound of the formula (I) and salt thereof as claimed in claim 1 wherein $R^1$ is $(C_1-C_4)$alkyl, $(C_1-C_4)$haloalkyl, $(C_1-C_4)$ hydroxyalkyl or $(C_1-C_4)$alkoxy-$(C_1-C_4)$alkyl, $R^2$ and $R^3$ independently of one another are hydrogen, amino, formyl or $(C_1-C_4)$alkyl or $R^2$ and $R^3$, together with the nitrogen atom of the group $NR^2R^3$, are a heterocyclic radical having 4 to 6 ring atoms which, in addition to the nitrogen atom, may contain a further hetero-ring atom from the group consisting of N and O as hetero-ring atom, $R^4$ is hydrogen or $(C_1-C_4)$alkyl, $R^5$ ethyl, n-propyl, i-propyl, n-butyl, i-butyl, sec-butyl and t-butyl; or $R^6$ is hydrogen, $(C_1-C_4)$alkyl, $(C_2-C_4)$alkenyl, $(C_2-C_4)$alkynyl, $(C_3-C_6)$cycloalkyl or $(C_1-C_4)$alkoxy-$(C_1-C_4)$alkyl or phenyl or $R^5$ and $R^6$ together are an alkylene chain having 2 to 4 carbon atoms, $R^7$ independently of one another are halogen, hydroxyl, amino, nitro, formyl, carboxyl, cyano, $(C_1-C_6)$alkyl, $(C_1-C_4)$alkoxy, halo$(C_1-C_4)$alkoxy, halo-$(C_1-C_4)$alkoxy, hydroxy-$(C_1-C_4)$alkyl, hydroxy-$(C_1-C_4)$alkoxy, $(C_1-C_4)$alkoxy-$(C_1-C_4)$alkyl, halo-$(C_1-C_4)$alkoxy-$(C_1-C_4)$alkyl, halo-$(C_1-C_4)$alkyloxy-$(C_1-C_4)$alkoxy, $(C_1-C_4)$alkoxy-$(C_1-C_4)$alkoxy, $(C_3-C_6)$cycloalkyl, halo-$(C_3-C_6)$cycloalkyl, $(C_2-C_6)$alkenyl, halo-$(C_2-C_6)$alkenyl, $(C_2-C_6)$alkynyl, halo-$(C_2-C_6)$alkynyl, $(C_1-C_4)$alkylcarbonyl, halo-$(C_1-C_4)$alkylcarbonyl, $(C_1-C_4)$alkoxycarbonyl, halo-$(C_1-C_4)$alkoxycarbonyl, $(C_1-C_4)$alkylcarbonyloxy, halo-$(C_1-C_4)$alkyl-carbonyloxy, $(C_1-C_4)$alkylcarbonyl-$(C_1-C_4)$alkyl, $(C_1-C_4)$alkylthio, halo-$(C_1-C_4)$alkylthio, $(C_1-C_4)$alkylamino, di-[$(C_1-C_4)$alkyl]-amino, phenyl, phenoxy, phenylcarbonyl, phenoxycarbonyl, phenylcarbonyloxy, phenoxy-$(C_1-C_4)$alkyl, phenylcarbonyl-$(C_1-C_4)$alkyl, phenyl-$(C_1-C_4)$alkyl, phenyl-$(C_2-C_4)$alkenyl, phenyl-$(C_2-C_4)$alkynyl, or one of the 10 last-mentioned radicals which is substituted in the cyclic moiety by one or more radicals from the group consisting of halogen, $(C_1-C_4)$alkyl, $(C_1-C_4)$alkoxy, $(C_1-C_4)$haloalkyl and $(C_1-C_4)$haloalkoxy, heterocyclyl in the radicals having 3 to 6 ring atoms and 1 to 3 hetero-ring atoms from the group consisting of N and O, or two adjacent radicals $R^7$ together are a fused-on cycle having 4 to 6 ring atoms, which is carbocyclic or contains hetero-ring atoms from the group consisting of O and N, and which is unsubstituted or substituted by one or more radicals $(C_1-C_4)$alkyl, X is a group of the formula —O— or —NH— and n is 0, 1, 2, 3, 4 or 5.

3. A compound of the formula (I) and salt thereof as claimed in claim 1 wherein a1) $R^1$ is $(C_1-C_4)$haloalkyl,
$R^2$, $R^3$, $R^4$, $R^6$ are each hydrogen,
$R^5$ is methyl,
n is the number 3, 4 or 5,
X is an oxygen atom and
$(R^7)n$ are n radicals $R^7$ which are identical or different, $R^7$ in each case being halogen, hydroxyl, amino, nitro, formyl, carboxyl, cyano, $(C_1-C_6)$alkyl, $(C_1-C_4)$alkoxy, halo-$(C_1-C_4)$alkyl, halo-$(C_1-C_4)$alkoxy, hydroxy-$(C_1-C_4)$alkyl, hydroxy-$(C_1-C_4)$alkoxy, $(C_1-C_4)$alkoxy-$(C_1-C_4)$alkyl, halo-$(C_1-C_4)$alkoxy-$(C_1-C_4)$alkyl, halo-$(C_1-C_4)$alkyloxy-$(C_1-C_4)$-alkoxy, $(C_1-C_4)$alkoxy-$(C_1-C_4)$alkoxy, $(C_3-C_6)$cycloalkyl, halo-$(C_3-C_6)$cycloalkyl, $(C_2-C_4)$alkenyl, halo-$(C_2-C_4)$alkenyl, $(C_2-C_4)$alkynyl, halo-$(C_2-C_4)$alkynyl, $(C_1-C_4)$alkylcarbonyl, $(C_1-C_4)$alkoxycarbonyl, $(C_1-C_4)$alkylcarbonyloxy, $(C_1-C_4)$alkylcarbonyl-$(C_1-C_4)$alkyl, $(C_1-C_4)$alkylthio, $(C_1-C_4)$alkylamino, di-[$(C_1-C_4)$-alkyl)-amino or phenyl, phenoxy, phenylcarbonyl, phenoxycarbonyl, phenylcarbonyloxy, phenoxy-$(C_1-C_4)$alkyl, phenylcarbonyl-$(C_1-C_4)$alkyl, phenyl-$(C_1-C_4)$alkyl or one of the 8 last-mentioned radicals which is substituted in the phenyl moiety by one or more radicals from the group consisting of halogen, $(C_1-C_4)$alkyl, $(C_1-C_4)$alkoxy, $(C_1-C_4)$haloalkyl and $(C_1-C_4)$haloalkoxy, or two adjacent radicals $R^7$ together are a fused-on cycle having 4 to 6 ring atoms, which is carbocyclic and which is unsubstituted or substituted more radicals $(C_1-C_4)$alkyl, or a2) $R^1$ is $(C_1-C_4)$haloalkyl,
$R^2$, $R^3$, $R^4$, $R^6$ are each hydrogen,
$R^5$ is methyl,
n is the number 1 or 2,
X is an oxygen atom,
$(R^7)$ are n radicals $R^7$ which, in the case of n=2, are defined the same, $R^7$ in each case being chlorine, bromine, iodine, hydroxyl, amino, nitro, formyl, carboxyl, cyano, $(C_2-C_4)$alkoxy, methyl which is substituted by one or more radicals from the group consisting of chlorine, bromine and iodine, $(C_2-C_4)$haloalkyl, halo-$(C_1-C_4)$alkoxy, hydroxy-$(C_1-C_4)$alkyl, hydroxy-$(C_1-C_4)$alkoxy, $(C_1-C_4)$alkoxy-$(C_1-C_4)$alkyl, halo-$(C_1-C_4)$alkoxy-$(C_1-C_4)$alkyl, halo-$(C_1-C_4)$alkyloxy-$(C_1-C_4)$alkoxy, $(C_1-C_4)$alkoxy-$(C_1-C_4)$alkoxy, $(C_3-C_6)$cycloalkyl, halo-$(C_3-C_6)$cycloalkyl, $(C_2-C_4)$alkenyl, halo-$(C_2-C_4)$alkenyl, $(C_2-C_4)$alkynyl, halo-$(C_2-C_4)$alkynyl, $(C_1-C_4)$alkylcarbonyl, $(C_1-C_4)$alkoxycarbonyl, $(C_1-C_4)$alkylcarbonlyoxy, $(C_1-C_4)$alkylcarbonyl-$(C_1-C_4)$alkyl, $(C_1-C_4)$alkylthio, $(C_1-C_4)$alkylamino, di-[$(C_1-C_4)$alkyl]-amino or phenyl, phenoxy, phenylcarbonyl, phenoxycarbonyl, phenylcarbonyloxy, phenoxy-$(C_1-C_4)$alkyl, phenylcarbonyl-$(C_1-C_4)$alkyl, phenyl-$(C_1-C_4)$alkyl or one of the 8 last-mentioned radicals which is substituted in the phenyl moiety by one or more radicals from the group consisting of halogen, $(C_1-C_4)$alkyl, $(C_1-C_4)$alkoxy, $(C_1-C_4)$ haloalkyl and $(C_1-C_4)$haloalkoxy, or two adjacent radicals $R^7$ together are a fused-on cycle having 4 to 6 ring atoms, which is carbocyclic and which is unsubstituted or substituted by one or more radicals $(C_1-C_4)$alkyl, or a3) $R^1$ is $(C_1-C_4)$haloalkyl,
$R^2$, $R^3$, $^4$, $R^6$ are each hydrogen,
$R^5$ is methyl,
n is the number 2,
X is an oxygen atom and
$(R^7)_n$ are the two radicals $R^7$, the two radicals $R^7$ being structurally different and otherwise as defined above under a1), or else two adjacent radicals $R^7$ together are a fused-on cycle having 4 to 6 ring atoms, which is carbocyclic and which is unsubstituted or substituted by one or more radicals $(C_1-C_4)$alkyl, or b1) $R^1$ is $(C_1-C_4)$,alkyl which is unsubstituted or substituted by 1 to 4 substituents from the group consisting of $(C_1-C_4)$alkoxy and hydroxyl,
$R^2$, $R^3$, $R^4$, $R^6$ are each hydrogen,
$R^5$ is methyl,
n is the number 1, 2, 3 or 4,
X is an oxygen atom and
$(R^7)_n$ are n radicals $R^7$ which, in the case of n=2, 3 or 4, are identical or different, $R^7$ in each case being hydroxyl, amino, nitro, formyl, carboxyl, cyano, $(C_1-C_4)$alkoxy, halo-$(C_1-C_4)$alkyl, halo-$(C_1-C_4)$alkoxy, hydroxy-$(C_1-C_4)$alkyl, hydroxy-$(C_1-C_4)$alkoxy, $(C_1-C_4)$alkoxy-$(C_1-C_4)$alkyl, halo-$(C_1-C_4)$alkoxy-$(C_1-C_4)$alkyl, halo-$(C_1-C_4)$alkyloxy-$(C_1-C_4)$-alkoxy, $(C_1-C_4)$alkoxy-$(C_1-C_4)$alkoxy, $(C_3-C_6)$cycloalkyl, halo-$(C_3-C_6)$cycloalkyl, $(C_2-C_4)$alkenyl, halo-$(C_2-C_4)$alkenyl, $(C_2-C_4)$alkynyl, halo-$(C_2-C_4)$alkynyl, $(C_1-C_4)$alkylcarbonyl, $(C_1-C_4)$alkoxycarbonyl, $(C_1-C_4)$alkylcarbonyloxy, $(C_1-C_4)$alkylcarbonyl-$(C_1-C_4)$alkyl, $(C_1-C_4)$alkylthio, halo-$(C_1-C_4)$alkylthio, $(C_1-C_4)$alkylamino, di-$(C_1-C_4)$-alkyl]-amino or phenyl, phenoxy, phenylcarbonyl, phenoxycarbonyl, phenylcarbonyloxy, phenoxy-$(C_1-C_4)$alkyl, phenylcarbonyl-$(C_1-C_4)$alkyl, phenyl-$(C_1-C_4)$alkyl or one of the 8 last-mentioned radicals which is substituted in the phenyl moiety by one or more radicals from the group consisting of halogen, $(C_1-C_4)$alkyl, $(C_1-C_4)$alkoxy, $(C_1-C_4)$haloalkyl and $(C_1-C_4)$haloalkoxy, or two adjacent radicals $R^7$ together are a fused-on cycle having 4 to 6 ring atoms, which is carbocyclic and which is unsubstituted or substituted by one or more radicals $(C_1-C_4)$alkyl.

4. A compound of the formula I or a salt thereof

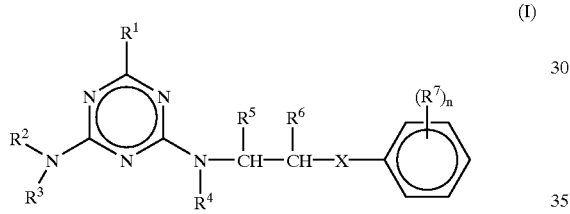

(I)

wherein
 $R^1$ is $(C_1-C_4)$haloalkyl,
 $R^2$, $R^3$, $R^4$, $R^6$ are each hydrogen
 $R^5$ is methyl
 n is the number 3, 4 or 5
 X is an oxygen atom and
 $(R^7)_n$ are n radicals $R^7$ which are identical or different, $R^7$ in each case being halogen, hydroxyl, amino, nitro, foreryl, carboxyl, cyano, $(C_1-C_6)$alkyl, $(C_1-C_4)$alkoxy, halo-$(C_1-C_4)$alkyl, halo-$(C_1-C_4)$alkoxy, hydroxy-$(C_1-C_4)$alkyl, hydroxy-$(C_1-C_4)$alkoxy, $(C_1-C_4)$alkoxy-$(C_1-C_4)$alkyl, halo-$(C_1-C_4)$alkoxy-$(C_1-C_4)$alkyl, halo$(C_1-C_4)$alkyloxy-$(C_1-C_4)$-alkoxy, $(C_1-C_4)$alkoxy-$(C_1-C_4)$alkoxy, $(C_3-C_6)$cycloalkyl, halo-$(C_3-C_6)$cycloalkyl, $(C_2-C_4)$alkenyl, halo-$(C_2-C_4)$alkenyl, $(C_2-C_4)$alkynyl, halo-$(C_2-C_4)$alkynyl, $(C_1-C_4)$alkylcarbonyl, $(C_1-C_4)$alkoxycarbonyt, $(C_1-C_4)$alkylcarbonyl, $(C_1-C_4)$alkylcarbonyl-$(C_1-C_4)$alkyl, $(C_1-C_4)$alkylthio, $(C_1-C_4)$alkylamino, di-[$(C_1-C_4)$-alkyl]-amino or phenyl, phenoxy, phenylcarbonyl, phenoxycarbonyl, phenylcarbonyoxy, phenoxy-$(C_1-C_4)$alkyl, phenylcarbonyl-$(C_1-C_4)$alkyl, phenyl-$(C_1-C_4)$alkyl or one of the 8 last-mentioned radicals which is substituted in the phenyl moiety by one or more radicals from the group consisting of h alogen, $(C_1-C_4)$alkyl, $(C_1-C_4)$alkoxy, $(C_1-C_4)$haloalkyl and $(C_1-C_4)$haloalkoxy, or two adjacent radicals $R^7$ together are a fused-on cycle having 4 to 6 ring atoms, which is carbocyclic and which is unsubstituted or substituted by one more radicals $(C_1-C_4)$alkyl.

5. A compound of the formula I or a salt thereof

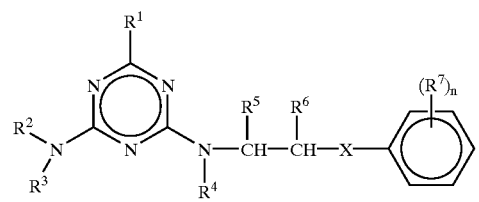

(I)

wherein
 $R^1$ is $(C_1-C_4)$haloalkyl,
 $R^2$, $R^3$, $R^4$, $R^6$ are each hydrogen,
 $R^5$ is methyl,
 n is the number 1 or 2,
 X is an oxygen atom and
 $(R^7)_n$ are n radicals $R^7$ which in the case of n=2 are defined the same, $R^7$ in each case being chlorine, bromine, iodine, hydroxyl, amino, nitro, formyl, carboxyl, cyano, $(C_2-C_4)$alkoxy, methyl which is substituted by one or more radicals from the group consisting of chlorine, bromine and iodine, $(C_2-C_4)$haloalkyl, halo-$(C_1-C_4)$alkoxy, hydroxy-$(C_1-C_4)$alkyl, hydroxy-$(C_1-C_4)$alkoxy, $(C_1-C_4)$alkoxy-$(C_1-C_4)$alkyl, halo-$(C_1-C_4)$alkoxy-$(C_1-C_4)$alkyl, halo-$(C_1-C_4)$alkyloxy-$(C_1-C_4)$-alkoxy, $(C_1-C_4)$alkoxy-$(C_1-C_4)$alkoxy, $(C_3-C_6)$cycloalkyl, halo-$(C_3-C_6)$cycloalkyl, $(C_2-C_4)$alkenyl, halo-$(C_2-C_4)$alkenyl, $(C_2-C_4)$alkynyl, halo-$(C_2-C_4)$alkynyl, $(C_1-C_4)$alkylcarbonyl, $(C_1-C_4)$alkoxycarbonyl, $(C_1-C_4)$alkylcarbonyloxy, $(C_1-C_4)$alkylcarbonyl-$(C_1-C_4)$alkyl, $(C_1-C_4)$alkylthio, $(C_1-C_4)$alkylamino, di[$(C_1-C_4)$-alkyl]-amino or phenyl, phenoxy, phenylcarbonyl, phenoxycarbonyl, phenylcarbonyloxy, phenoxy-$(C_1-C_4)$alkyl, phenylcarbonyl-$(C_1-C_4)$alkyl, phenyl-$(C_1-C_4)$alkyl or one of the 8 last-mentioned radicals which is substituted in the phenyl moiety by one or more radicals from the group consisting of halogen, $(C_1-C_4)$alkyl, $(C_1-C_4)$alkoxy, $(C_1-C_4)$haloalkyl and $(C_1-C_4)$haloalkoxy, or two adjacent radicals $R^7$ together are a fused-on cycle having 4 to 6 ring atoms, which is carbocyclic and which is unsubstituted or substituted by one or more radicals $(C_1-C_4)$alkyl.

6. A compound of the formula I or a salt therof

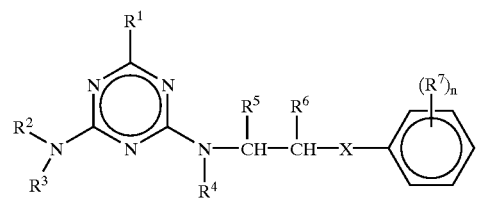

(I)

wherein
 R1 is $(C_1-C_4)$haloalkyl,
 $R^2$, $R^3$, $R^4$, $R^6$ are each hydrogen,
 $R^5$ is methyl,
 n is the number 2,
 X is an oxygen atom and
 $(R^7)n$ are the two radicals $R^7$, the two radical $R^7$ being structurally different and otherwise as defined above under a1), or else two adjacent radicals $R^7$ together are a fused-on cycle having 4 to 6 ring atoms, which is carbocyclic and which is unsubstituted or substituted by one or more radicals $(C_1-C_4)$alkyl.

7. A compound of the formula I or a salt thereof

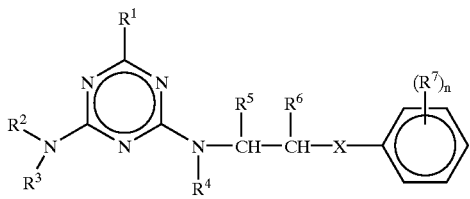
(I)

wherein $R^1$ is $(C_1-C_4)$alkyl which is unsubstituted or substituted by 1 to 4 substituents from the group consisting of $(C_1-C_4)$alkoxy and hydroxyl, $R^2$, $R^3$, $R^4$, $R^6$ are each hydrogen, $R^5$ is methyl, n is the number 1, 2, 3 or 4, X is an oxygen atom and $(R^7)n$ are n' radicals $R^7$ which, in the case of n=2, 3 or 4 are identical or different, $R^7$ in each case being hydroxyl, amino, nitro, formyl, carboxyl, cyano, $(C_1-C_4)$alkoxy, halo-$(C_1-C_4)$alkyl, halo-$(C_1-C_4)$alkoxy, hydroxy-$(C_1-C_4)$alkyl, hydroxy-$(C_1-C_4)$alkoxy, $(C_1-C_4)$alkoxy-$(C_1-C_4)$alkyl, halo-$(C_1-C_4)$alkoxy-$(C_1-C_4)$alkyl, halo-$(C_1-C_4)$alkyloxy-$(C_1-C_4)$alkoxy, $(C_1-C_4)$alkoxy-$(C_1-C_4)$alkoxy, $(C_3-C_6)$cycloalkyl, halo-$(C_3-C_6)$cycloalkyl, $(C_2-C_4)$alkenyl, halo-$(C_2-C_4)$alkenyl, $(C_2-C_4)$alkynyl, halo-$(C_2-C_4)$alkynyl, $(C_1-C_4)$alkylcarbonyl, $(C_1-C_4)$alkoxycarbonyl, $(C_1-C_4)$alkylcarbonyloxy, $(C_1-C_4)$alkylcarbonyl-$(C_1-C_4)$alkyl, $(C_1-C_4)$alkylthio, halo-$(C_1-C_4)$alkylthio, $(C_1-C_4)$alkylamino, di[$(C_1-C_4)$alkyl]-amino, or phenyl, phenoxy, phenylcarbonyl, phenoxycarbonyl, phenylcarbonyloxy, phenoxy-$(C_1-C_4)$alkyl, phenylcarbonyl-$(C_1-C_4)$alkyl, phenyl-$(C_1-C_4)$alkyl or one of the 8 last-mentioned radicals which is substituted in the phenyl moiety by one or more radicals from the group consisting of halogen, $(C_1-C_4)$alkyl, $(C_1-C_4)$alkoxy, $(C_1-C_4)$haloalkyl and $(C_1-C_4)$haloalkoxy, or two adjacent radicals $R^7$ together are a fused-on cycle having 4 to 6 ring atoms, which is carbocyclic and which is unsubstituted or substituted by one or more radicals $(C_1-C_4)$alkyl.

8. The compound according to claim 1, which is

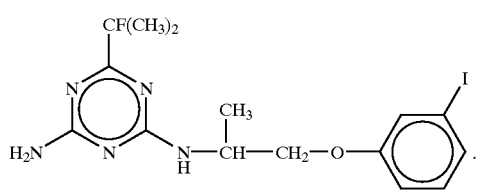

9. A compound of the formula (I) or a salt thereof as claimed in claim 1 where the compound is

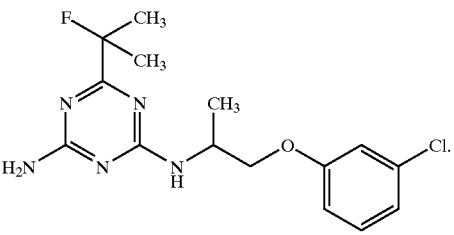

10. A compound of the formula (I) or a salt thereof as claimed in claim 1 where the compound is

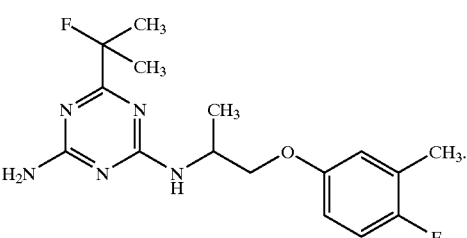

11. A process for preparing a compound of the formula (I) or salt thereof as claimed in claim 1 which comprises (a) reacting a compound of the formula II $$R^1-Fu \qquad (II)$$

in which Fu is a functional group from the group consisting of carboxylate, carboxylic acid ortho ester, carbonyl chloride, carboxamide, carboxylic anhydride and trichloromethyl with a biguanidide of the formula (III) or an acid addition salt thereof

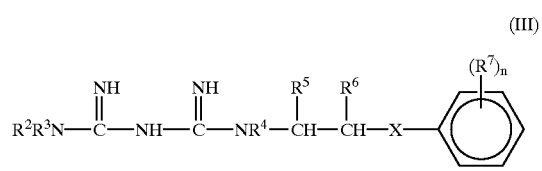
(III)

or b) reacting a compound of the formula (IV)

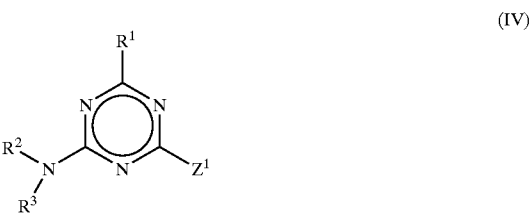
(IV)

in which $Z^1$ is an exchangeable radical or a leaving group, with a suitable amine of the formula (V) or an acid addition salt thereof

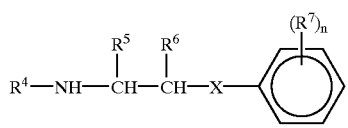 (V)

where, in the formulae (II), (III), (IV), and (V), the radicals $R^1$ to $R^7$ and X and also n are as defined for formula (I).

12. A herbicidal or plant growth-regulating composition, which comprises one or more compounds of the formula (I) or salts thereof as claimed in claim 1 and formulation auxiliaries, which are customary in crop protection.

13. A method of controlling weeds or of regulating the growth of plants, which comprises applying an effective amount of one or more compounds of the formula (I) or salts thereof as claimed in claim 1 to the plants, to plant seeds or to the area under cultivation.

* * * * *